(12) United States Patent
Lee et al.

(10) Patent No.: US 11,653,851 B2
(45) Date of Patent: May 23, 2023

(54) METHODS FOR FUNCTIONAL BRAIN CIRCUIT ANALYSIS

(71) Applicant: The Board of Trustees of the Leland Stanford Junior University, Stanford, CA (US)

(72) Inventors: Jin Hyung Lee, Palo Alto, CA (US); Hyun Joo Lee, Stanford, CA (US); Andrew J. Weitz, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 750 days.

(21) Appl. No.: 15/781,688

(22) PCT Filed: Nov. 30, 2016

(86) PCT No.: PCT/US2016/064250
§ 371 (c)(1),
(2) Date: Jun. 5, 2018

(87) PCT Pub. No.: WO2017/100058
PCT Pub. Date: Jun. 15, 2017

(65) Prior Publication Data
US 2018/0360343 A1    Dec. 20, 2018

Related U.S. Application Data

(60) Provisional application No. 62/265,291, filed on Dec. 9, 2015.

(51) Int. Cl.
*A61B 5/055* (2006.01)
*A61N 5/06* (2006.01)
(Continued)

(52) U.S. Cl.
CPC ............ *A61B 5/055* (2013.01); *A61B 5/0059* (2013.01); *A61B 5/369* (2021.01); *A61B 5/4064* (2013.01);
(Continued)

(58) Field of Classification Search
CPC ....... A61B 5/055; A61B 5/4064; A61B 5/369; A61B 5/377; A61B 2503/42; A61N 5/0622
See application file for complete search history.

(56) References Cited

U.S. PATENT DOCUMENTS

| 5,387,742 A | 2/1995 | Cordell |
| 6,649,811 B2 | 11/2003 | Pasinetti |

(Continued)

FOREIGN PATENT DOCUMENTS

| WO | WO 2009131837 | 10/2009 |
| WO | WO 2010056970 | 5/2010 |

(Continued)

OTHER PUBLICATIONS

Liang et al.; Mapping the functional network of medial prefrontal cortex by combining optogenetics and fMRI in awake rats; published online on May 20, 2015; NeuroImage; vol. 117, pp. 114-123 (Year: 2015).*

(Continued)

*Primary Examiner* — Chao Sheng
(74) *Attorney, Agent, or Firm* — Rudy J. Ng; Paula A. Borden; Bozicevic, Field & Francis LLP

(57) ABSTRACT

Provided herein are methods for analyzing in vivo a brain circuit. A method of the present disclosure may include using optogenetics to stimulate a first region of a brain of an individual, in conjunction with functional magnetic resonance imaging (fMRI) of different regions of the brain to determine a dynamic functional connection between indi- (Continued)

vidual neurons of the first region and a second region of the brain. The method may further include identifying a third region of the brain, the neurons of which region mediate the dynamic functional connection between the first and second regions.

22 Claims, 34 Drawing Sheets

Specification includes a Sequence Listing.

(51) Int. Cl.
*A61B 5/00* (2006.01)
*A61B 5/369* (2021.01)
*A61B 5/377* (2021.01)

(52) U.S. Cl.
CPC ............ *A61N 5/0622* (2013.01); *A61B 5/377* (2021.01); *A61B 2503/42* (2013.01)

(56) References Cited

U.S. PATENT DOCUMENTS

| | | | |
|---|---|---|---|
| 7,632,679 | B2 | 12/2009 | Jessell et al. |
| 8,834,546 | B2 | 9/2014 | Deisseroth et al. |
| 2009/0093403 | A1 | 4/2009 | Zhang et al. |
| 2010/0145418 | A1 | 6/2010 | Zhang et al. |
| 2013/0289386 | A1* | 10/2013 | Deisseroth ............ A61B 5/055 600/411 |
| 2014/0364721 | A1 | 12/2014 | Lee et al. |

FOREIGN PATENT DOCUMENTS

| | | | |
|---|---|---|---|
| WO | WO 2011116238 | 9/2011 | |
| WO | WO-2013036965 A2 * | 3/2013 | ........... A61B 5/0036 |
| WO | WO 2014121146 | 8/2014 | |
| WO | WO 2016121146 | 8/2016 | |

OTHER PUBLICATIONS

Pisanello et al.; The Three-Dimensional Signal Collection Field for Fiber Photometry in Brain Tissue; published on Feb. 26, 2019; Frontiers in Neuroscience; vol. 13, Article 82 (Year: 2019).*
Gradinaru et al. (eNpHR: a Natronomonas halorhodopsin enhanced foroptogenetic applications; published online on Aug. 2, 2008; Brain Cell Biology vol. 36, 129-139, 2008 (Year: 2008).*
Leong et al., (2015) "Frequency Specific Optogenetic Recruitment of Evoked Responses in the Somatosensory Thalamocortical Circuit", ISMRM 135.
Weitz et al., (2014) "Optogenetic fMRI Reveals Distinct, Frequency-Dependent Networks Recruited by Dorsal and Intermediate Hippocampus Stimulations", NeuroImage 107:229-241.
Berndt et al., (2011) "High-efficiency channelrhodopsins for fast neuronal stimulation at low light levels." *Proc Natl Acad Sci USA*, 108(18): 7595-7600.
Entcheva and Williams (2014) "Channelrhodopsin2 Current During the Action Potential: "Optical AP Clamp" and Approximation" *Scientific Reports*, 4(5838): 1-7.
Grossman et al., (2011) "Modeling Study of the Light Stimulation of a Neuron Cell With Channelrhodopsin-2 Mutants," *IEEE Transactions on Biomedical Engineering*, 58(6): 1742-1751.
Shmuel et al., (2002) "Sustained Negative BOLD, Blood Flow and Oxygen Consumption Response and Its Coupling to the Positive Response in the Human Brain," *Neuron*, 36(6): 1195-1210.

* cited by examiner

Figure 1C   Figure 1D

10 Hz Stimulation

40 Hz Stimulation

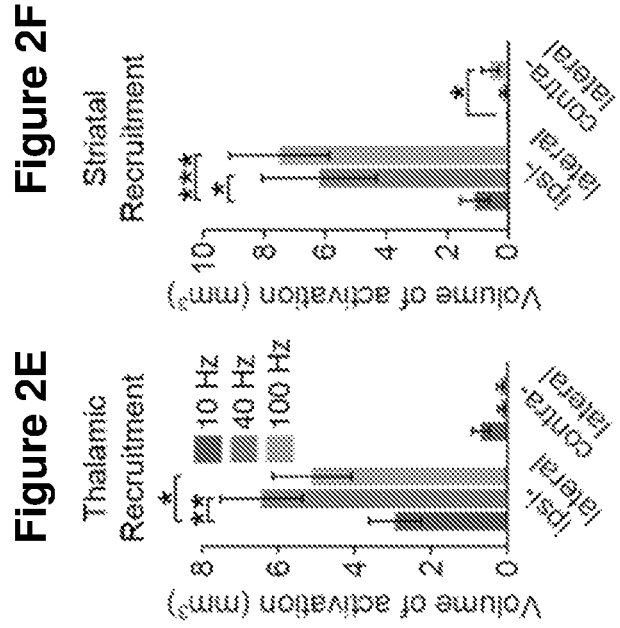
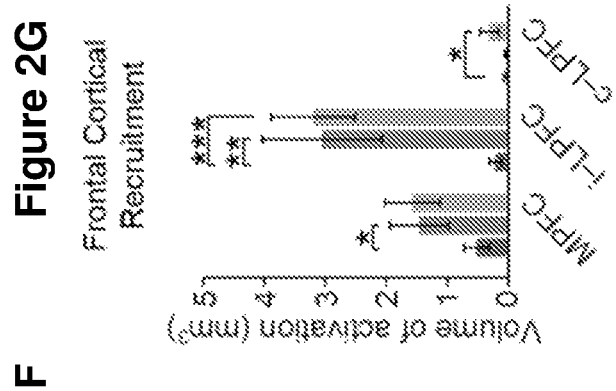
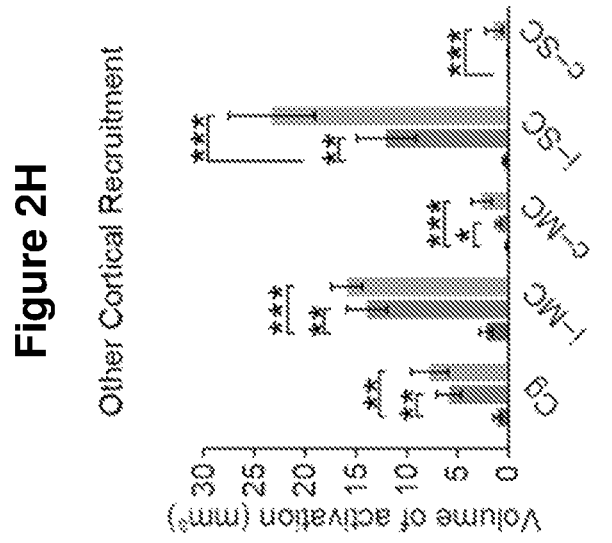
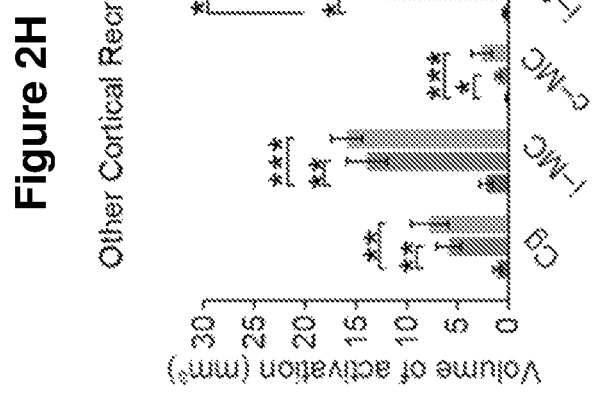

Figure 5D
Figure 5E
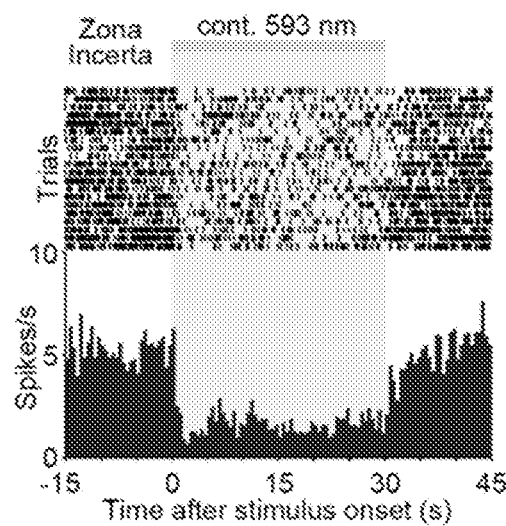
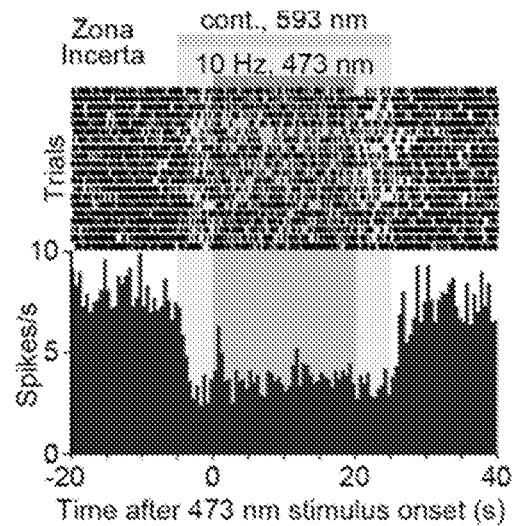
Figure 5F
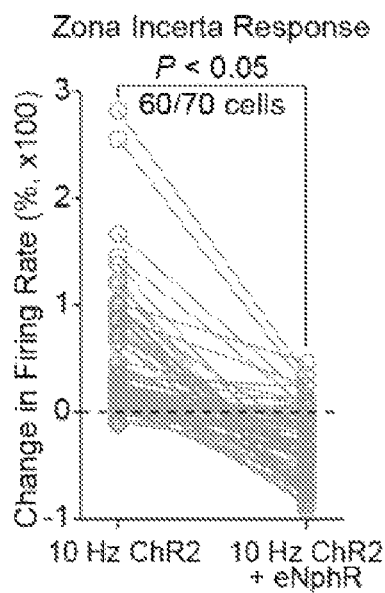

Figure 14

(Depolarizing opsins)
Amino acid sequence of ChR2 (SEQ ID NO:1)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP

Amino acid sequence of ChR2 with ER export and trafficking signal
sequences (SEQ ID NO:2)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP*AAA***KSRITSEGE
YIPLDQIDINV**FCYENEV amino acid sequence of a ChR2 SSFO (SEQ ID NO:3)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TSPVILIHLSNLTGLSNDYSRRTMGLLVSAIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP amino acid sequence of a ChR2 SSFO with ER export and trafficking signal
sequences (SEQ ID NO:4)

MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TSPVILIHLSNLTGLSNDYSRRTMGLLVSAIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP*AAA***KSRITSEGE
YIPLDQIDINV**FCYENEV

Figure 14 (Cont.)

Amino acid sequence of a VChR1 (SEQ ID NO:5)

Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed

Amino acid sequence of a VChR1 with ER export and trafficking signal sequences (SEQ ID NO:6)

Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed*AAA*KSRITSEGEYIPLDQIDINVFCY
ENEV amino acid sequence of C1V1 (SEQ ID NO:7)

MSRRPWLLALALAVALAAGSAGASTGSDATVPVATQDGPDYVFHRAHERMLFQTSYTLENN
GSVICIPNNGQCFCLAWLKSNGTNAEKLAANILQWITFALSALCLMFYGYQTWKSTCGWEEIY
VATIEMIKFIIEYFHEFDEPAVIYSSNGNKTVWLRYAEWLLTCPVLLIHLSNLTGLKDDYSKRT
MGLLVSDVGCIVWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLGNYLRVKIHEHI
LLYGDIRKKQKITIAGQEMEVETLVAEEED amino acid sequence of C1V1 with ER export and trafficking signal sequences (SEQ ID NO:8)

MSRRPWLLALALAVALAAGSAGASTGSDATVPVATQDGPDYVFHRAHERMLFQTSYTLENN
GSVICIPNNGQCFCLAWLKSNGTNAEKLAANILQWITFALSALCLMFYGYQTWKSTCGWEEIY
VATIEMIKFIIEYFHEFDEPAVIYSSNGNKTVWLRYAEWLLTCPVLLIHLSNLTGLKDDYSKRT
MGLLVSDVGCIVWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLGNYLRVKIHEHI
LLYGDIRKKQKITIAGQEMEVETLVAEEED*AAA*KSRITSEGEYIPLDQIDINVFCYENEV

Amino acid sequence of a C1C2 (SEQ ID NO:9)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAV

Figure 14 (Cont.)

Amino acid sequence of a C1C2 with ER export and trafficking signal sequences (SEQ ID NO:10)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAV*AA
A*__KSRITSEGEYIPLDQIDINV__FCYENEV

Amino acid sequence of ReaChR (red shifted ChR) (SEQ ID NO:11)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS

Amino acid sequence of ReaChR (red shifted ChR) with ER export and trafficking signal sequences (SEQ ID NO:12)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS
*AAA*__KSRITSEGEYIPLDQIDINV__FCYENEV

Amino acid sequence of SdChR (CheRiff) (SEQ ID NO:13)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv

Amino acid sequence of SdChR (CheRiff) with ER export and trafficking signal sequences (SEQ ID NO:14)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv*AAA*__KSRITSEGEYIPLDQIDINV__FCYENEV

Figure 14 (Cont.)

Amino acid sequence of CnChR1 (Chrimson) (SEQ ID NO:15)
Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirkttkmeiggeeveveefveeededtv

Amino acid sequence of CnChR1 (Chrimson) with ER export and trafficking signal sequences (SEQ ID NO:16)
Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirkttkmeiggeeveveefveeededtv*AAA*KSRITSEGEYIPLDQIDINVFCYENEV

Amino acid sequence of CsChrimson (SEQ ID NO:17)
Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirkttkmeiggeeveveefveeededtv

Amino acid sequence of CsChrimson with ER export and trafficking signal sequences (SEQ ID NO:18)
Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirkttkmeiggeeveveefveeededtv*AAA*KSRITSEGEYIPLDQIDINVFCYENEV

Amino acid sequence of ShChR1 (Chronos) (SEQ ID NO:19)
metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirkttinvag
enmeietfvdeeeeggv

Figure 14 (Cont.)

Amino acid sequence of ShChR1 (Chronos) with ER export and trafficking signal sequences (SEQ ID NO:20)

metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirkttinvag
enmeietfvdeeeeggv*AAA*KSRITSEGEYIPLDQIDINVFCYENEV

Figure 15

(hyperpolarizing opsins)
amino acid sequence of Archaerhodopsin-3 (SEQ ID NO:21)
MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD amino acid sequence of eArch3.0 (SEQ ID NO:22)
MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD*RPVVAAAA***KSRITSEGEYIPLD
QIDINV**FCYENEV Amino acid sequence of ArchT (SEQ ID NO:23)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP

Amino acid sequence of ArchT with ER export and trafficking signal
sequences (SEQ ID NO:24)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP*AAA*KSRITSEGEYIPLDQIDINVFCYENEV

Figure 15 (Cont.)

amino acid sequence of GtR3 (SEQ ID NO:25)
MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI amino acid sequence of GtR3 with ER export and trafficking signal
sequences (SEQ ID NO:26)
MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI*AAA*KSRITSEGEYIPLDQIDINVFCYENEV Amino acid sequence of rhodopsin type II proton pump (Oxy) (SEQ ID
NO:27)
MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA Amino acid sequence of rhodopsin type II proton pump with ER export
and trafficking signal sequences(SEQ ID NO:28)
MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA*AAA***KSRITSEGEYIPLDQ
IDINV**FCYENEV

Figure 15 (Cont.)

Amino acid sequence of L. maculans rhodopsin (Mac) (SEQ ID NO:29)
MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGA

Amino acid sequence of Mac 3.0 (SEQ ID NO:30)
MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGARPVVAVSKAAAKSRITSEGEYIPLDQIDINV_FCYENE_
_V_ amino acid sequence of NpHR (SEQ ID NO:31)

<u>MTETLPPVTESAVALQAE</u>VTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD amino acid sequence of NpHR3.0 (SEQ ID NO:32)

<u>MTETLPPVTESAVALQAE</u>VTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD<u>AAAKSRITSEGEYIPLDQIDINFCYENEV</u> amino acid sequence of NpHR3.1 (SEQ ID NO:33)

MVTQRELFEFVLNDPLLASSLYINIALAGLSILLFVFMTRGLDDPRAKLIAVSTILVPVVSIASYTG
LASGLTISVLEMPAGHFAEGSSVMLGGEEVDGVVTMWGRYLTWALSTPMILLALGLLAGSNAT
KLFTAITFDIAMCVTGLAAALTTSSHLMRWFWYAISCACFLVVLYILLVEWAQDAKAAGTADM
FNTLKLLTVVMWLGYPIVWALGVEGIAVLPVGVTSWGYSFLDIVAKYIFAFLLLNYLTSNESVVS
GSILDVPSASGTPADD<u>AAAKSRITSEGEYIPLDQIDINFCYENEV</u>

Figure 15 (Cont.)

**Amino acid sequence of *Dunaliella salina* channelrhodopsin** (SEQ ID NO:34)
Mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv

**Amino acid sequence of *Dunaliella salina* channelrhodopsin** with ER export and trafficking signal sequences (SEQ ID NO:35)
mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv*AAA***KSRITSEGEYIPLDQID
INV**FCYENEV

Amino acid sequence of a iC1C2 (SEQ ID NO:36)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

Amino acid sequence of a iC1C2 with ER export and trafficking signal sequences (SEQ ID NO:37)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV*AA
A*KSRITSEGEYIPLDQIDINVFCYENEV

Amino acid sequence of a SwiChR (iC1C2-C167A or T or S) (SEQ ID NO:38)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

Figure 15 (Cont.)

Amino acid sequence of a SwiChR (iC1C2-C167A or T or S) with ER export and trafficking signal sequences (SEQ ID NO:39)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV*AA
A*<u>KSRITSEGEYIPLDQIDINVFCYENEV</u>

Amino acid sequence of ibC1C2 (SEQ ID NO:40)
MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

Amino acid sequence of ibC1C2 with ER export and trafficking signal sequences (SEQ ID NO:41)
MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV*AAA*<u>KSRITSEGEYIPLDQIDINVFCYENEV</u>

Amino acid sequence of iChR2 (SEQ ID NO:42)
MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

Amino acid sequence of iChR2 with ER export and trafficking signal sequences (SEQ ID NO:43)
MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP*AAA*<u>KSRITSEGEYIPLDQIDINVFCYENEV</u>

Figure 15 (Cont.)

Amino acid sequence of iC1V1 (SEQ ID NO:44)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED

Amino acid sequence of iC1V1 with ER export and trafficking signal sequences
(SEQ ID NO:45)
MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED*AAA***KSR
ITSEGEYIPLDQIDINV**FCYENEV

Amino acid sequence of ibC1V1 (SEQ ID NO:46)
MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

Amino acid sequence of ibC1V1 with ER export and trafficking signal sequences
(SEQ ID NO:47)
MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED*AAA*KSRITSEGEYIPLDQIDINVFCYENEV

Amino acid sequence of iReaChR (SEQ ID NO:48)
MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS

Figure 15 (Cont.)

Amino acid sequence of iReaChR with ER export and trafficking signal sequences (SEQ ID NO:49)
MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS
*AAA*KSRITSEGEYIPLDQIDINVFCYENEV

Amino acid sequence of ibReaChR (SEQ ID NO:50)
MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

Amino acid sequence of ibReaChR with ER export and trafficking signal sequences (SEQ ID NO:51)
MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
    IRKKQKITIAGQEMEVETLVAEEEDKYESS*AAA*KSRITSEGEYIPLDQIDINVFCYENEV

SEQUENCE LISTING

<160> NUMBER OF SEQ ID NOS: 64

<210> SEQ ID NO 1
<211> LENGTH: 310
<212> TYPE: PRT
<213> ORGANISM: Chlamydomonas reinhardtii

<400> SEQUENCE: 1

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 2
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 2

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
            325                 330                 335

Glu Asn Glu Val
            340

<210> SEQ ID NO 3
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 3

Met Asp Tyr Gly Gly Ala Leu Ser Ala Val Gly Arg Glu Leu Leu Phe
1               5                   10                  15
```

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 4
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 4

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
            85                  90                  95

Glu Phe Phe Glu Phe Lys Asn Pro Ser Met Leu Tyr Leu Ala Thr
        100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
        340

<210> SEQ ID NO 5
<211> LENGTH: 300
<212> TYPE: PRT
<213> ORGANISM: Volvox carteri

<400> SEQUENCE: 5

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu

-continued

```
                    85                  90                  95
Phe Asp Ser Pro Ala Thr Leu Trp Leu Ser Ser Gly Asn Gly Val Val
                100                 105                 110
Trp Met Arg Tyr Gly Glu Trp Leu Leu Thr Cys Pro Val Leu Leu Ile
                115                 120                 125
His Leu Ser Asn Leu Thr Gly Leu Lys Asp Asp Tyr Ser Lys Arg Thr
            130                 135                 140
Met Gly Leu Leu Val Ser Asp Val Gly Cys Ile Val Trp Gly Ala Thr
145                 150                 155                 160
Ser Ala Met Cys Thr Gly Trp Thr Lys Ile Leu Phe Phe Leu Ile Ser
                165                 170                 175
Leu Ser Tyr Gly Met Tyr Thr Tyr Phe His Ala Ala Lys Val Tyr Ile
                180                 185                 190
Glu Ala Phe His Thr Val Pro Lys Gly Ile Cys Arg Glu Leu Val Arg
            195                 200                 205
Val Met Ala Trp Thr Phe Phe Val Ala Trp Gly Met Phe Pro Val Leu
210                 215                 220
Phe Leu Leu Gly Thr Glu Gly Phe Gly His Ile Ser Pro Tyr Gly Ser
225                 230                 235                 240
Ala Ile Gly His Ser Ile Leu Asp Leu Ile Ala Lys Asn Met Trp Gly
                245                 250                 255
Val Leu Gly Asn Tyr Leu Arg Val Lys Ile His Glu His Ile Leu Leu
                260                 265                 270
Tyr Gly Asp Ile Arg Lys Lys Gln Lys Ile Thr Ile Ala Gly Gln Glu
            275                 280                 285
Met Glu Val Glu Thr Leu Val Ala Glu Glu Asp
        290                 295                 300

<210> SEQ ID NO 6
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 6

Met Asp Tyr Pro Val Ala Arg Ser Leu Ile Val Arg Tyr Pro Thr Asp
1               5                   10                  15
Leu Gly Asn Gly Thr Val Cys Met Pro Arg Gly Gln Cys Tyr Cys Glu
                20                  25                  30
Gly Trp Leu Arg Ser Arg Gly Thr Ser Ile Glu Lys Thr Ile Ala Ile
            35                  40                  45
Thr Leu Gln Trp Val Val Phe Ala Leu Ser Val Ala Cys Leu Gly Trp
        50                  55                  60
Tyr Ala Tyr Gln Ala Trp Arg Ala Thr Cys Gly Trp Glu Glu Val Tyr
65                  70                  75                  80
Val Ala Leu Ile Glu Met Met Lys Ser Ile Ile Glu Ala Phe His Glu
                85                  90                  95
Phe Asp Ser Pro Ala Thr Leu Trp Leu Ser Ser Gly Asn Gly Val Val
                100                 105                 110
Trp Met Arg Tyr Gly Glu Trp Leu Leu Thr Cys Pro Val Leu Leu Ile
                115                 120                 125
His Leu Ser Asn Leu Thr Gly Leu Lys Asp Asp Tyr Ser Lys Arg Thr
            130                 135                 140
Met Gly Leu Leu Val Ser Asp Val Gly Cys Ile Val Trp Gly Ala Thr
```

```
                145                 150                 155                 160
        Ser Ala Met Cys Thr Gly Trp Thr Lys Ile Leu Phe Phe Leu Ile Ser
                        165                 170                 175
        Leu Ser Tyr Gly Met Tyr Thr Tyr Phe His Ala Ala Lys Val Tyr Ile
                        180                 185                 190
        Glu Ala Phe His Thr Val Pro Lys Gly Ile Cys Arg Glu Leu Val Arg
                        195                 200                 205
        Val Met Ala Trp Thr Phe Phe Val Ala Trp Gly Met Phe Pro Val Leu
                210                 215                 220
        Phe Leu Leu Gly Thr Glu Gly Phe Gly His Ile Ser Pro Tyr Gly Ser
        225                 230                 235                 240
        Ala Ile Gly His Ser Ile Leu Asp Leu Ile Ala Lys Asn Met Trp Gly
                        245                 250                 255
        Val Leu Gly Asn Tyr Leu Arg Val Lys Ile His Glu His Ile Leu Leu
                        260                 265                 270
        Tyr Gly Asp Ile Arg Lys Lys Gln Lys Ile Thr Ile Ala Gly Gln Glu
                        275                 280                 285
        Met Glu Val Glu Thr Leu Val Ala Glu Glu Asp Ala Ala Ala Lys
                290                 295                 300
        Ser Arg Ile Thr Ser Glu Gly Glu Tyr Ile Pro Leu Asp Gln Ile Asp
        305                 310                 315                 320
        Ile Asn Val Phe Cys Tyr Glu Asn Glu Val
                        325                 330

<210> SEQ ID NO 7
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 7

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
                20                  25                  30
Val Ala Thr Gln Asp Gly Pro Asp Tyr Val Phe His Arg Ala His Glu
                35                  40                  45
Arg Met Leu Phe Gln Thr Ser Tyr Thr Leu Glu Asn Asn Gly Ser Val
            50                  55                  60
Ile Cys Ile Pro Asn Asn Gly Gln Cys Phe Cys Leu Ala Trp Leu Lys
65                  70                  75                  80
Ser Asn Gly Thr Asn Ala Glu Lys Leu Ala Ala Asn Ile Leu Gln Trp
                85                  90                  95
Ile Thr Phe Ala Leu Ser Ala Leu Cys Leu Met Phe Tyr Gly Tyr Gln
                100                 105                 110
Thr Trp Lys Ser Thr Cys Gly Trp Glu Glu Ile Tyr Val Ala Thr Ile
            115                 120                 125
Glu Met Ile Lys Phe Ile Ile Glu Tyr Phe His Glu Phe Asp Glu Pro
        130                 135                 140
Ala Val Ile Tyr Ser Ser Asn Gly Asn Lys Thr Val Trp Leu Arg Tyr
145                 150                 155                 160
Ala Glu Trp Leu Leu Thr Cys Pro Val Leu Leu Ile His Leu Ser Asn
                165                 170                 175
Leu Thr Gly Leu Lys Asp Asp Tyr Ser Lys Arg Thr Met Gly Leu Leu
```

```
                180                 185                 190
Val Ser Asp Val Gly Cys Ile Val Trp Gly Ala Thr Ser Ala Met Cys
            195                 200                 205

Thr Gly Trp Thr Lys Ile Leu Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Asp
            340

<210> SEQ ID NO 8
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
            165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
```

```
                    195                 200                 205
Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp Ala Ala Ala Lys Ser Arg Ile Thr
            340                 345                 350

Ser Glu Gly Glu Tyr Ile Pro Leu Asp Gln Ile Asp Ile Asn Val Phe
        355                 360                 365

Cys Tyr Glu Asn Glu Val
    370

<210> SEQ ID NO 9
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
```

```
                180                 185                 190
Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Val Tyr Gly Ser Thr Val Gly His
        275                 280                 285

Thr Ile Ile Asp Leu Met Ser Lys Asn Cys Trp Gly Leu Leu Gly His
            290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345
```

<210> SEQ ID NO 10
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 10

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
```

```
            195                 200                 205
Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Val Tyr Gly Ser Thr Val Gly His
                275                 280                 285

Thr Ile Ile Asp Leu Met Ser Lys Asn Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ala Ala Ala Lys
                340                 345                 350

Ser Arg Ile Thr Ser Glu Gly Glu Tyr Ile Pro Leu Asp Gln Ile Asp
                355                 360                 365

Ile Asn Val Phe Cys Tyr Glu Asn Glu Val
    370                 375
```

<210> SEQ ID NO 11
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 11

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
                35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Thr Phe Ala Leu Ser Val Ala Cys Leu Gly Trp Tyr Ala Tyr
                100                 105                 110

Gln Ala Trp Arg Ala Thr Cys Gly Trp Glu Glu Val Tyr Val Ala Leu
                115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
```

```
                180             185             190
Leu Val Ser Asp Val Gly Cys Ile Val Trp Gly Ala Thr Ser Ala Met
            195                 200                 205

Cys Thr Gly Trp Thr Lys Ile Leu Phe Phe Leu Ile Ser Leu Ser Tyr
        210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
            245                 250                 255

Trp Leu Phe Phe Val Ser Trp Gly Met Phe Pro Val Leu Phe Leu Leu
        260                 265                 270

Gly Pro Glu Gly Phe Gly His Ile Ser Pro Tyr Gly Ser Ala Ile Gly
            275                 280                 285

His Ser Ile Leu Asp Leu Ile Ala Lys Asn Met Trp Gly Val Leu Gly
        290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
            325                 330                 335

Glu Thr Leu Val Ala Glu Glu Asp Lys Tyr Glu Ser Ser
        340                 345                 350

<210> SEQ ID NO 12
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 12

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
            85                  90                  95

Trp Val Thr Phe Ala Leu Ser Val Ala Cys Leu Gly Trp Tyr Ala Tyr
        100                 105                 110

Gln Ala Trp Arg Ala Thr Cys Gly Trp Glu Glu Val Tyr Val Ala Leu
    115                 120                 125

Ile Glu Met Met Lys Ser Ile Glu Ala Phe His Glu Phe Asp Ser
        130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
            165                 170                 175

Asn Leu Thr Gly Leu Lys Asp Asp Tyr Ser Lys Arg Thr Met Gly Leu
        180                 185                 190

Leu Val Ser Asp Val Gly Cys Ile Val Trp Gly Ala Thr Ser Ala Met
```

```
                195                 200                 205
Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Pro Tyr Gly Ser Ala Ile Gly
                275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
                340                 345                 350

Ala Lys Ser Arg Ile Thr Ser Glu Gly Glu Tyr Ile Pro Leu Asp Gln
                355                 360                 365

Ile Asp Ile Asn Val Phe Cys Tyr Glu Asn Glu Val
370                 375                 380

<210> SEQ ID NO 13
<211> LENGTH: 316
<212> TYPE: PRT
<213> ORGANISM: Scherffelia dubia

<400> SEQUENCE: 13

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
                20                  25                  30

Asn Pro Pro Tyr His Pro Val His Gly Tyr Glu Glu Gln Cys Ser Ser
                35                  40                  45

Ile Tyr Ile Tyr Tyr Gly Ala Leu Trp Glu Gln Glu Thr Ala Arg Gly
                50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
                100                 105                 110

Thr Ser Pro Ala Met Leu Phe Leu Tyr Gly Gly Asn Ile Thr Pro Trp
                115                 120                 125

Leu Arg Tyr Ala Glu Trp Leu Leu Thr Cys Pro Val Ile Leu Ile His
                130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
                180                 185                 190
```

Val Tyr Gly Thr Gln Thr Phe Tyr Asn Ala Gly Ile Ile Tyr Val Glu
            195                 200                 205

Ser Tyr Tyr Ile Met Pro Ala Gly Gly Cys Lys Lys Leu Val Leu Ala
210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
            245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
            275                 280                 285

Gly Asp Ile Arg Arg Pro Val Ser Ser Gln Phe Leu Gly Arg Lys Val
290                 295                 300

Asp Val Leu Ala Phe Val Thr Glu Glu Asp Lys Val
305                 310                 315

<210> SEQ ID NO 14
<211> LENGTH: 346
<212> TYPE: PRT
<213> ORGANISM: Artificial sequence
<220> FEATURE:
<223> OTHER INFORMATION: Synthetic polypeptide

<400> SEQUENCE: 14

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
            35                  40                  45

Ile Tyr Ile Tyr Tyr Gly Ala Leu Trp Glu Gln Glu Thr Ala Arg Gly
        50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
            195                 200                 205

Ser Tyr Tyr Ile Met Pro Ala Gly Gly Cys Lys Lys Leu Val Leu Ala
        210                 215                 220

Met Thr Ala Val Tyr Tyr Ser Ser Trp Leu Met Phe Pro Gly Leu Phe
225                 230                 235                 240

```
Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
290                 295                 300

Asp Val Leu Ala Phe Val Thr Glu Glu Asp Lys Val Ala Ala Ala Lys
305                 310                 315                 320

Ser Arg Ile Thr Ser Glu Gly Val Tyr Ile Pro Leu Asp Gln Ile Asp
                325                 330                 335

Ile Asn Val Phe Cys Tyr Glu Asn Glu Val
            340                 345

<210> SEQ ID NO 15
<211> LENGTH: 350
<212> TYPE: PRT
<213> ORGANISM: Chlamydomonas noctigama

<400> SEQUENCE: 15

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270
```

Ala Val Gly Pro Glu Gly Leu Leu Lys Leu Ser Pro Tyr Ala Asn Ser
                275                 280                 285

Ile Gly His Ser Ile Cys Asp Ile Ile Ala Lys Glu Phe Trp Thr Phe
            290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
                325                 330                 335

Glu Val Glu Glu Phe Val Glu Glu Asp Glu Asp Thr Val
            340                 345                 350

<210> SEQ ID NO 16
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 16

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

```
Ile Gly His Ser Ile Cys Asp Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
                325                 330                 335

Glu Val Glu Glu Phe Val Glu Glu Asp Glu Asp Thr Val Ala Ala
            340                 345                 350

Ala Lys Ser Arg Ile Thr Ser Glu Gly Glu Tyr Ile Pro Leu Asp Gln
        355                 360                 365

Ile Asp Ile Asn Val Phe Cys Tyr Glu Asn Glu Val
    370                 375                 380

<210> SEQ ID NO 17
<211> LENGTH: 345
<212> TYPE: PRT
<213> ORGANISM: Artificial sequence
<220> FEATURE:
<223> OTHER INFORMATION: Synthetic polypeptide

<400> SEQUENCE: 17

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270
```

```
Gly Leu Leu Lys Leu Ser Pro Tyr Ala Asn Ser Ile Gly His Ser Ile
            275                 280                 285

Cys Asp Ile Ile Ala Lys Glu Phe Trp Thr Phe Leu Ala His His Leu
        290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
                325                 330                 335

Val Glu Glu Glu Asp Glu Asp Thr Val
            340                 345

<210> SEQ ID NO 18
<211> LENGTH: 375
<212> TYPE: PRT
<213> ORGANISM: Artificial sequence
<220> FEATURE:
<223> OTHER INFORMATION: Synthetic polypeptide

<400> SEQUENCE: 18

Met Ser Arg Leu Val Ala Ala Ser Trp Leu Leu Ala Leu Leu Leu Cys
1               5                   10                  15

Gly Ile Thr Ser Thr Thr Ala Ser Ser Ala Pro Ala Ala Ser Ser
            20                  25                  30

Thr Asp Gly Thr Ala Ala Ala Val Ser His Tyr Ala Met Asn Gly
            35                  40                  45

Phe Asp Glu Leu Ala Lys Gly Ala Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285
```

```
Cys Asp Ile Ile Ala Lys Glu Phe Trp Thr Phe Leu Ala His His Leu
        290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
            325                 330                 335

Val Glu Glu Asp Glu Asp Thr Val Ala Ala Ala Lys Ser Arg Ile
        340                 345                 350

Thr Ser Glu Gly Glu Tyr Ile Pro Leu Asp Gln Ile Asp Ile Asn Val
        355                 360                 365

Phe Cys Tyr Glu Asn Glu Val
        370                 375

<210> SEQ ID NO 19
<211> LENGTH: 325
<212> TYPE: PRT
<213> ORGANISM: Stigeoclonium helveticum

<400> SEQUENCE: 19

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
                20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
        50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
        210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
```

```
                      275                 280                 285
His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325

<210> SEQ ID NO 20
<211> LENGTH: 355
<212> TYPE: PRT
<213> ORGANISM: Artificial sequence
<220> FEATURE:
<223> OTHER INFORMATION: Synthetic polypeptide

<400> SEQUENCE: 20

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
                20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
```

```
                    305                 310                 315                 320
Glu Glu Gly Gly Val Ala Ala Lys Ser Arg Ile Thr Ser Glu Gly
                325                 330                 335

Glu Tyr Ile Pro Leu Asp Gln Ile Asp Ile Asn Val Phe Cys Tyr Glu
            340                 345                 350

Asn Glu Val
        355

<210> SEQ ID NO 21
<211> LENGTH: 258
<212> TYPE: PRT
<213> ORGANISM: Halorubrum sodomense

<400> SEQUENCE: 21

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 22
<211> LENGTH: 293
<212> TYPE: PRT
<213> ORGANISM: Artificial sequence
<220> FEATURE:
<223> OTHER INFORMATION: Synthetic polypeptide

<400> SEQUENCE: 22
```

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Ala Ala Lys Ser Arg Ile Thr Ser
            260                 265                 270

Glu Gly Glu Tyr Ile Pro Leu Asp Gln Ile Asp Ile Asn Val Phe Cys
            275                 280                 285

Tyr Glu Asn Glu Val
            290

<210> SEQ ID NO 23
<211> LENGTH: 248
<212> TYPE: PRT
<213> ORGANISM: Halorubrum sp. TP009

<400> SEQUENCE: 23

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
            85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
            165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
            245

<210> SEQ ID NO 24
<211> LENGTH: 278
<212> TYPE: PRT
<213> ORGANISM: Artificial sequence
<220> FEATURE:
<223> OTHER INFORMATION: Synthetic polypeptide

<400> SEQUENCE: 24

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
            50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
            85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
            165                 170                 175

Val Ala Ser Thr Phe Asn Thr Leu Thr Ala Leu Val Leu Val Leu Trp
            180                 185                 190

```
Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ala Ala Lys Ser Arg Ile Thr
                245                 250                 255

Ser Glu Gly Glu Tyr Ile Pro Leu Asp Gln Ile Asp Ile Asn Val Phe
                260                 265                 270

Cys Tyr Glu Asn Glu Val
        275
```

<210> SEQ ID NO 25
<211> LENGTH: 242
<212> TYPE: PRT
<213> ORGANISM: Guillardia theta

<400> SEQUENCE: 25

```
Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
                20                  25                  30

Ile Val Phe Ala Cys Ile Thr Leu Leu Gly Ile Asn Ala Ala Lys
            35                  40                  45

Ser Lys Ala Ala Ser Arg Val Leu Phe Pro Ala Thr Phe Val Thr Gly
50                  55                  60

Ile Ala Ser Ile Ala Tyr Phe Ser Met Ala Ser Gly Gly Gly Trp Val
65                  70                  75                  80

Ile Ala Pro Asp Cys Arg Gln Leu Phe Val Ala Arg Tyr Leu Asp Trp
                85                  90                  95

Leu Ile Thr Thr Pro Leu Leu Leu Ile Asp Leu Gly Leu Val Ala Gly
                100                 105                 110

Val Ser Arg Trp Asp Ile Met Ala Leu Cys Leu Ser Asp Val Leu Met
            115                 120                 125

Ile Ala Thr Gly Ala Phe Gly Ser Leu Thr Val Gly Asn Val Lys Trp
130                 135                 140

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
                165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
        195                 200                 205

Val Thr Phe Glu Val Leu Ile Tyr Gly Val Leu Asp Val Ile Ser Lys
210                 215                 220

Ala Val Phe Gly Leu Ile Leu Met Ser Gly Ala Ala Thr Gly Tyr Glu
225                 230                 235                 240

Ser Ile
```

<210> SEQ ID NO 26
<211> LENGTH: 272
<212> TYPE: PRT
<213> ORGANISM: Artificial sequence
<220> FEATURE:
<223> OTHER INFORMATION: Synthetic polypeptide

<400> SEQUENCE: 26

Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
            20                  25                  30

Ile Val Phe Ala Cys Ile Thr Leu Leu Gly Ile Asn Ala Ala Lys
        35                  40                  45

Ser Lys Ala Ala Ser Arg Val Leu Phe Pro Ala Thr Phe Val Thr Gly
50                  55                  60

Ile Ala Ser Ile Ala Tyr Phe Ser Met Ala Ser Gly Gly Gly Trp Val
65                  70                  75                  80

Ile Ala Pro Asp Cys Arg Gln Leu Phe Val Ala Arg Tyr Leu Asp Trp
                85                  90                  95

Leu Ile Thr Thr Pro Leu Leu Leu Ile Asp Leu Gly Leu Val Ala Gly
            100                 105                 110

Val Ser Arg Trp Asp Ile Met Ala Leu Cys Leu Ser Asp Val Leu Met
        115                 120                 125

Ile Ala Thr Gly Ala Phe Gly Ser Leu Thr Val Gly Asn Val Lys Trp
130                 135                 140

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
                165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
        195                 200                 205

Val Thr Phe Glu Val Leu Ile Tyr Gly Val Leu Asp Val Ile Ser Lys
210                 215                 220

Ala Val Phe Gly Leu Ile Leu Met Ser Gly Ala Ala Thr Gly Tyr Glu
225                 230                 235                 240

Ser Ile Ala Ala Ala Lys Ser Arg Ile Thr Ser Glu Gly Glu Tyr Ile
                245                 250                 255

Pro Leu Asp Gln Ile Asp Ile Asn Val Phe Cys Tyr Glu Asn Glu Val
            260                 265                 270

<210> SEQ ID NO 27
<211> LENGTH: 262
<212> TYPE: PRT
<213> ORGANISM: Oxyrrhis marina

<400> SEQUENCE: 27

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Phe Asn Val Gly Leu Gly Val
65                  70                  75                  80

```
Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
130                 135                 140

Gly Glu Ile Gln Asp Asp Leu Ser Val Arg Trp Phe Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Ser Trp Leu Thr Tyr Pro Phe Val
        195                 200                 205

Tyr Ile Val Lys Asn Ile Gly Leu Ala Gly Ser Thr Ala Thr Met Tyr
    210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
            260

<210> SEQ ID NO 28
<211> LENGTH: 292
<212> TYPE: PRT
<213> ORGANISM: Artificial sequence
<220> FEATURE:
<223> OTHER INFORMATION: Synthetic polypeptide

<400> SEQUENCE: 28

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
130                 135                 140

Gly Glu Ile Gln Asp Asp Leu Ser Val Arg Trp Phe Trp Ala Cys
145                 150                 155                 160

Ala Met Val Pro Phe Val Tyr Val Val Gly Thr Leu Val Val Gly Leu
                165                 170                 175
```

```
Gly Ala Ala Thr Ala Lys Gln Pro Glu Val Val Asp Leu Val Ser
                180             185                 190

Ala Ala Arg Tyr Leu Thr Val Val Ser Trp Leu Thr Tyr Pro Phe Val
            195                 200                 205

Tyr Ile Val Lys Asn Ile Gly Leu Ala Gly Ser Thr Ala Thr Met Tyr
        210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala Ala Ala Lys Ser Arg Ile Thr Ser Glu
                260                 265                 270

Gly Glu Tyr Ile Pro Leu Asp Gln Ile Asp Ile Asn Val Phe Cys Tyr
            275                 280                 285

Glu Asn Glu Val
        290

<210> SEQ ID NO 29
<211> LENGTH: 313
<212> TYPE: PRT
<213> ORGANISM: Leptosphaeria maculans

<400> SEQUENCE: 29

Met Ile Val Asp Gln Phe Glu Glu Val Leu Met

```
Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 30
<211> LENGTH: 351
<212> TYPE: PRT
<213> ORGANISM: Artificial sequence
<220> FEATURE:
<223> OTHER INFORMATION: Synthetic polypeptide

<400> SEQUENCE: 30

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300
```

Ile Arg Ile Gly Glu Asp Asp Gly Ala Arg Pro Val Ala Val Ser
305                 310                 315                 320

Lys Ala Ala Ala Lys Ser Arg Ile Thr Ser Glu Gly Glu Tyr Ile Pro
            325                 330                 335

Leu Asp Gln Ile Asp Ile Asn Val Phe Cys Tyr Glu Asn Glu Val
        340                 345                 350

<210> SEQ ID NO 31
<211> LENGTH: 291
<212> TYPE: PRT
<213> ORGANISM: Natronomonas pharaonis

<400> SEQUENCE: 31

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290

<210> SEQ ID NO 32
<211> LENGTH: 320
<212> TYPE: PRT

<213> ORGANISM: Artificial sequence
<220> FEATURE:
<223> OTHER INFORMATION: Synthetic polypeptide

<400> SEQUENCE: 32

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Ala Leu Gly Leu Leu Ala Gly Ser
        130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Ala Ala Ala Lys Ser Arg Ile Thr Ser Glu Gly Glu Tyr
290                 295                 300

Ile Pro Leu Asp Gln Ile Asp Ile Asn Phe Cys Tyr Glu Asn Glu Val
305                 310                 315                 320

<210> SEQ ID NO 33
<211> LENGTH: 303
<212> TYPE: PRT
<213> ORGANISM: Artificial sequence
<220> FEATURE:
<223> OTHER INFORMATION: Synthetic polypeptide

<400> SEQUENCE: 33

Met Val Thr Gln Arg Glu Leu Phe Glu Phe Val Leu Asn Asp Pro Leu
1               5                   10                  15

```
Leu Ala Ser Ser Leu Tyr Ile Asn Ile Ala Leu Ala Gly Leu Ser Ile
                20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Val Ser Ile Ala Ser
        50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
        115                 120                 125

Ala Thr Lys Leu Phe Thr Ala Ile Thr Phe Asp Ile Ala Met Cys Val
        130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Thr Val Val Met Trp Leu Gly Tyr
                195                 200                 205

Pro Ile Val Trp Ala Leu Gly Val Glu Gly Ile Ala Val Leu Pro Val
210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
        275                 280                 285

Pro Leu Asp Gln Ile Asp Ile Asn Phe Cys Tyr Glu Asn Glu Val
        290                 295                 300

<210> SEQ ID NO 34
<211> LENGTH: 365
<212> TYPE: PRT
<213> ORGANISM: Dunaliella salina

<400> SEQUENCE: 34

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
                20                  25                  30

Glu Arg Arg Pro Pro Ser Glu Arg Asn Thr Pro Tyr Ala Asn Ile Lys
            35                  40                  45

Lys Val Pro Asn Ile Thr Glu Pro Asn Ala Asn Val Gln Leu Asp Gly
        50                  55                  60

Trp Ala Leu Tyr Gln Asp Phe Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95
```

Ser His Gly Thr Asp Arg Glu Gly Glu Ala Ala Val Val Trp Ala Tyr
              100                 105                 110

Ile Val Phe Ala Ile Cys Ile Val Gln Leu Val Tyr Phe Met Phe Ala
              115                 120                 125

Ala Trp Lys Ala Thr Val Gly Trp Glu Val Tyr Val Asn Ile Ile
130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
              165                 170                 175

Ser Ala Trp Leu Leu Ser Cys Pro Val Ile Leu Ile His Leu Ser Asn
              180                 185                 190

Leu Thr Gly Leu Lys Gly Asp Tyr Ser Lys Arg Thr Met Gly Leu Leu
              195                 200                 205

Val Ser Asp Ile Gly Thr Ile Val Phe Gly Thr Ser Ala Ala Leu Ala
              210                 215                 220

Pro Pro Asn His Val Lys Val Ile Leu Phe Thr Ile Gly Leu Leu Tyr
225                 230                 235                 240

Gly Leu Phe Thr Phe Thr Ala Ala Lys Val Tyr Ile Glu Ala Tyr
              245                 250                 255

His Thr Val Pro Lys Gly Gln Cys Arg Asn Leu Val Arg Ala Met Ala
              260                 265                 270

Trp Thr Tyr Phe Val Ser Trp Ala Met Phe Pro Ile Leu Phe Ile Leu
              275                 280                 285

Gly Arg Glu Gly Phe Gly His Ile Thr Tyr Phe Gly Ser Ser Ile Gly
              290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
              325                 330                 335

Leu Thr Lys Lys Asn Lys Ile Asn Ile Ala Gly Asp Asn Val Glu Val
              340                 345                 350

Glu Glu Tyr Val Asp Ser Asn Asp Lys Asp Ser Asp Val
              355                 360                 365

<210> SEQ ID NO 35
<211> LENGTH: 395
<212> TYPE: PRT
<213> ORGANISM: Artificial sequence
<220> FEATURE:
<223> OTHER INFORMATION: Synthetic polypeptide

<400> SEQUENCE: 35

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
              20                  25                  30

Glu Arg Arg Pro Pro Ser Glu Arg Asn Thr Pro Tyr Ala Asn Ile Lys
              35                  40                  45

Lys Val Pro Asn Ile Thr Glu Pro Asn Ala Asn Val Gln Leu Asp Gly
50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
              85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Val Tyr Val Asn Ile Ile
130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285

Gly Arg Glu Gly Phe Gly His Ile Thr Tyr Phe Gly Ser Ser Ile Gly
290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val Ala Ala Ala
        355                 360                 365

Lys Ser Arg Ile Thr Ser Glu Gly Tyr Ile Pro Leu Asp Gln Ile
370                 375                 380

Asp Ile Asn Val Phe Cys Tyr Glu Asn Glu Val
385                 390                 395

<210> SEQ ID NO 36
<211> LENGTH: 348
<212> TYPE: PRT
<213> ORGANISM: Artificial sequence
<220> FEATURE:
<223> OTHER INFORMATION: Synthetic polypeptide

<400> SEQUENCE: 36

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
            165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
            245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
            275                 280                 285

Thr Ile Ile Asp Leu Met Ser Lys Gln Cys Trp Gly Leu Leu Gly His
            290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
            325                 330                 335

Thr Leu Val Glu Asp Glu Ala Glu Ala Gly Ala Val
            340                 345

<210> SEQ ID NO 37
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 37

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Asn Ile Leu Gln Trp
            85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
            165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
    195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
            245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
            275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
            325                 330                 335

Thr Leu Val Glu Asp Glu Ala Glu Ala Gly Ala Val Ala Ala Ala Lys
            340                 345                 350

Ser Arg Ile Thr Ser Glu Gly Glu Tyr Ile Pro Leu Asp Gln Ile Asp
            355                 360                 365

Ile Asn Val Phe Cys Tyr Glu Asn Glu Val
    370                 375

<210> SEQ ID NO 38
<211> LENGTH: 348
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (167)..(167)
<223> OTHER INFORMATION: Xaa may be Thr or Ser.

<400> SEQUENCE: 38

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu

```
            35                  40                  45
Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Asn Ile Leu Gln Trp
                 85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 39
<211> LENGTH: 378
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (167)..(167)
<223> OTHER INFORMATION: Xaa may be Thr or Ser.

<400> SEQUENCE: 39

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                20                  25                  30
```

```
Val Ala Thr Gln Asp Gly Pro Asp Tyr Val Phe His Arg Ala His Glu
         35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
        210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val Ala Ala Ala Lys
            340                 345                 350

Ser Arg Ile Thr Ser Glu Gly Glu Tyr Ile Pro Leu Asp Gln Ile Asp
        355                 360                 365

Ile Asn Val Phe Cys Tyr Glu Asn Glu Val
370                 375

<210> SEQ ID NO 40
<211> LENGTH: 309
<212> TYPE: PRT
<213> ORGANISM: Artificial sequence
<220> FEATURE:
<223> OTHER INFORMATION: Synthetic polypeptide

<400> SEQUENCE: 40

Met Asp Tyr Gly Gly Ala Leu Ser Ala Val Gly Leu Phe Gln Thr Ser
 1               5                  10                  15
```

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
 50                  55                  60

Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Ile Leu Ile Arg Leu Ser Asn Leu Thr Gly Leu Ala Asn Asp
        130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val
305

<210> SEQ ID NO 41
<211> LENGTH: 339
<212> TYPE: PRT
<213> ORGANISM: Artificial sequence
<220> FEATURE:
<223> OTHER INFORMATION: Synthetic polypeptide

<400> SEQUENCE: 41

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Ile Ser Phe Ala Leu Ser Ala
 50                  55                  60

```
Leu Cys Leu Met Phe Tyr Gly Tyr Gln Thr Trp Lys Ser Thr Cys Gly
 65                  70                  75                  80

Trp Glu Glu Ile Tyr Val Ala Thr Ile Ser Met Ile Lys Phe Ile Ile
                 85                  90                  95

Glu Tyr Phe His Ser Phe Asp Glu Pro Ala Val Ile Tyr Ser Ser Asn
                100                 105                 110

Gly Asn Lys Thr Lys Trp Leu Arg Tyr Ala Ser Trp Leu Leu Thr Cys
            115                 120                 125

Pro Val Ile Leu Ile Arg Leu Ser Asn Leu Thr Gly Leu Ala Asn Asp
            130                 135                 140

Tyr Asn Lys Arg Thr Met Gly Leu Leu Val Ser Asp Ile Gly Thr Ile
145                 150                 155                 160

Val Trp Gly Thr Thr Ala Ala Leu Ser Lys Gly Tyr Val Arg Val Ile
                165                 170                 175

Phe Phe Leu Met Gly Leu Cys Tyr Gly Ile Tyr Thr Phe Phe Asn Ala
                180                 185                 190

Ala Lys Val Tyr Ile Glu Ala Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Ala Ala Lys Ser Arg Ile Thr Ser Glu Gly
305                 310                 315                 320

Glu Tyr Ile Pro Leu Asp Gln Ile Asp Ile Asn Val Phe Cys Tyr Glu
                325                 330                 335

Asn Glu Val

<210> SEQ ID NO 42
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 42

Met Asp Tyr Gly Gly Ala Leu Ser Ala Val Gly Arg Glu Leu Leu Phe
 1               5                  10                  15

Val Thr Asn Pro Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ser Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Ser Met Val Lys Val Ile Leu
```

```
                85                  90                  95
Glu Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
            115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 43
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 43

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
            115                 120                 125

Pro Val Ile Leu Ile Arg Leu Ser Asn Leu Thr Gly Leu Ser Asn Asp
```

```
                130                 135                 140
Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
                340

<210> SEQ ID NO 44
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 44

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
                35                  40                  45

Arg Met Leu Phe Gln Thr Ser Tyr Thr Leu Glu Asn Asn Gly Ser Val
                50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125

Ser Met Ile Lys Phe Ile Glu Tyr Phe His Ser Phe Asp Glu Pro
                130                 135                 140

Ala Val Ile Tyr Ser Ser Asn Gly Asn Lys Thr Lys Trp Leu Arg Tyr
```

```
145                 150                 155                 160
Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
                195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Lys Tyr Gly Ser Asn Ile Gly His
                275                 280                 285

Ser Ile Leu Asp Leu Ile Ala Lys Gln Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 45
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 45

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
            130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
```

```
                    165                 170                 175
Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
            275                 280                 285

Ser Ile Leu Asp Leu Ile Ala Lys Gln Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp Ala Ala Ala Lys Ser Arg Ile Thr
            340                 345                 350

Ser Glu Gly Glu Tyr Ile Pro Leu Asp Gln Ile Asp Ile Asn Val Phe
            355                 360                 365

Cys Tyr Glu Asn Glu Val
            370

<210> SEQ ID NO 46
<211> LENGTH: 305
<212> TYPE: PRT
<213> ORGANISM: Artificial sequence
<220> FEATURE:
<223> OTHER INFORMATION: Synthetic polypeptide

<400> SEQUENCE: 46

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
            50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
            85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
            115                 120                 125

Pro Val Leu Leu Ile Arg Leu Ser Asn Leu Thr Gly Leu Lys Asp Asp
            130                 135                 140

Tyr Ser Lys Arg Thr Met Gly Leu Leu Val Ser Asp Val Gly Cys Ile
```

```
                145                 150                 155                 160
Val Trp Gly Ala Thr Ser Ala Met Cys Thr Gly Trp Thr Lys Ile Leu
                    165                 170                 175

Phe Phe Leu Ile Ser Leu Ser Tyr Gly Met Tyr Thr Tyr Phe His Ala
                    180                 185                 190

Ala Lys Val Tyr Ile Glu Ala Phe His Thr Val Pro Lys Gly Ile Cys
                    195                 200                 205

Arg Glu Leu Val Arg Val Met Ala Trp Thr Phe Phe Val Ala Trp Gly
                    210                 215                 220

Met Phe Pro Val Leu Phe Leu Gly Thr Glu Gly Phe Gly His Ile
225                 230                 235                 240

Ser Lys Tyr Gly Ser Asn Ile Gly His Ser Ile Leu Asp Leu Ile Ala
                    245                 250                 255

Lys Gln Met Trp Gly Val Leu Gly Asn Tyr Leu Arg Val Lys Ile His
                    260                 265                 270

Glu His Ile Leu Leu Tyr Gly Asp Ile Arg Lys Gln Lys Ile Thr
                    275                 280                 285

Ile Ala Gly Gln Glu Met Glu Val Glu Thr Leu Val Ala Glu Glu Glu
                    290                 295                 300

Asp
305

<210> SEQ ID NO 47
<211> LENGTH: 335
<212> TYPE: PRT
<213> ORGANISM: Artificial sequence
<220> FEATURE:
<223> OTHER INFORMATION: Synthetic polypeptide

<400> SEQUENCE: 47

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                    20                  25                  30

Gln Cys Phe Cys Leu Ala Trp Leu Lys Ser Asn Gly Thr Asn Ala Glu
                    35                  40                  45

Lys Leu Ala Ala Asn Ile Leu Gln Trp Ile Ser Phe Ala Leu Ser Ala
    50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                    85                  90                  95

Glu Tyr Phe His Ser Phe Asp Glu Pro Ala Val Ile Tyr Ser Ser Asn
                    100                 105                 110

Gly Asn Lys Thr Lys Trp Leu Arg Tyr Ala Ser Trp Leu Leu Thr Cys
                    115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                    165                 170                 175

Phe Phe Leu Ile Ser Leu Ser Tyr Gly Met Tyr Thr Tyr Phe His Ala
                    180                 185                 190

Ala Lys Val Tyr Ile Glu Ala Phe His Thr Val Pro Lys Gly Ile Cys
```

```
            195                 200                 205
Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Gln Lys Ile Thr
            275                 280                 285

Ile Ala Gly Gln Glu Met Glu Val Glu Thr Leu Val Ala Glu Glu Glu
        290                 295                 300

Asp Ala Ala Lys Ser Arg Ile Thr Ser Glu Gly Glu Tyr Ile Pro
305                 310                 315                 320

Leu Asp Gln Ile Asp Ile Asn Val Phe Cys Tyr Glu Asn Glu Val
                325                 330                 335

<210> SEQ ID NO 48
<211> LENGTH: 350
<212> TYPE: PRT
<213> ORGANISM: Artificial sequence
<220> FEATURE:
<223> OTHER INFORMATION: Synthetic polypeptide

<400> SEQUENCE: 48

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
```

```
            225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
                260                 265                 270

Gly Pro Glu Gly Phe Gly His Ile Ser Lys Tyr Gly Ser Asn Ile Gly
                275                 280                 285

His Ser Ile Leu Asp Leu Ile Ala Lys Gln Met Trp Gly Val Leu Gly
                290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
                340                 345                 350

<210> SEQ ID NO 49
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 49

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
                35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Ser Phe Ala Leu Ser Val Ala Cys Leu Gly Trp Tyr Ala Tyr
                100                 105                 110

Gln Ala Trp Arg Ala Thr Cys Gly Trp Glu Glu Val Tyr Val Ala Leu
                115                 120                 125

Ile Ser Met Met Lys Ser Ile Ile Glu Ala Phe His Ser Phe Asp Ser
        130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
                195                 200                 205

Cys Thr Gly Trp Thr Lys Ile Leu Phe Phe Leu Ile Ser Leu Ser Tyr
        210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
```

```
            245                 250                 255
Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
            275                 280                 285

His Ser Ile Leu Asp Leu Ile Ala Lys Gln Met Trp Gly Val Leu Gly
            290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
                340                 345                 350

Ala Lys Ser Arg Ile Thr Ser Glu Gly Glu Tyr Ile Pro Leu Asp Gln
                355                 360                 365

Ile Asp Ile Asn Val Phe Cys Tyr Glu Asn Glu Val
                370                 375                 380

<210> SEQ ID NO 50
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 50

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Cys
            115                 120                 125

Pro Val Ile Leu Ile Arg Leu Ser Asn Leu Thr Gly Leu Lys Asp Asp
        130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
```

```
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
                275                 280                 285

Ile Ala Gly Gln Glu Met Glu Val Gly Thr Leu Val Ala Glu Glu Glu
            290                 295                 300

Asp Lys Tyr Glu Ser Ser
305             310

<210> SEQ ID NO 51
<211> LENGTH: 340
<212> TYPE: PRT
<213> ORGANISM: Artificial sequence
<220> FEATURE:
<223> OTHER INFORMATION: Synthetic polypeptide

<400> SEQUENCE: 51

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Ser Met Met Lys Ser Ile Ile
                85                  90                  95

Glu Ala Phe His Ser Phe Asp Ser Pro Ala Thr Leu Trp Leu Ser Ser
            100                 105                 110

Gly Asn Gly Val Lys Trp Met Arg Tyr Gly Ser Trp Leu Leu Thr Cys
        115                 120                 125

Pro Val Ile Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
```

```
              275                 280                 285
Ile Ala Gly Gln Glu Met Glu Val Glu Thr Leu Val Ala Glu Glu
            290                 295                 300

Asp Lys Tyr Glu Ser Ser Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340

<210> SEQ ID NO 52
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa may be any amino acid.
<220> FEATURE:
<221> NAME/KEY: MISC_FEATURE
<222> LOCATION: (3)..(3)
<223> OTHER INFORMATION: Xaa may be any amino acid.

<400> SEQUENCE: 52

Val Xaa Xaa Ser Leu
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 53

Val Lys Glu Ser Leu
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 54

Val Leu Gly Ser Leu
1               5

<210> SEQ ID NO 55
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 55

Asn Ala Asn Ser Phe Cys Tyr Glu Asn Glu Val Ala Leu Thr Ser Lys
1               5                   10                  15

<210> SEQ ID NO 56
<211> LENGTH: 20
<212> TYPE: PRT
<213> ORGANISM: Artificial sequence
```

```
<220> FEATURE:
<223> OTHER INFORMATION: Synthetic polypeptide

<400> SEQUENCE: 56

Lys Ser Arg Ile Thr Ser Glu Gly Glu Tyr Ile Pro Leu Asp Gln Ile
1               5                   10                  15

Asp Ile Asn Val
            20

<210> SEQ ID NO 57
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa may be any amino acid.

<400> SEQUENCE: 57

Phe Xaa Tyr Glu Asn Glu
1               5

<210> SEQ ID NO 58
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 58

Phe Cys Tyr Glu Asn Glu Val
1               5

<210> SEQ ID NO 59
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 59

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 60
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 60

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 61
<211> LENGTH: 18
<212> TYPE: PRT
<213> ORGANISM: Artificial sequence
<220> FEATURE:
```

```
<223> OTHER INFORMATION: Synthetic polypeptide

<400> SEQUENCE: 61

Met Arg Gly Thr Pro Leu Leu Leu Val Val Ser Leu Phe Ser Leu Leu
1               5                   10                  15

Gln Asp

<210> SEQ ID NO 62
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 62

Met Thr Glu Thr Leu Pro Pro Val Thr Glu Ser Ala Val Ala Leu Gln
1               5                   10                  15

Ala Glu

<210> SEQ ID NO 63
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 63

Met Asp Tyr Gly Gly Ala Leu Ser Ala Val Gly
1               5                   10

<210> SEQ ID NO 64
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 64

Met Gly Leu Arg Ala Leu Met Leu Trp Leu Leu Ala Ala Ala Gly Leu
1               5                   10                  15

Val Arg Glu Ser Leu Gln Gly
            20
```

METHODS FOR FUNCTIONAL BRAIN CIRCUIT ANALYSIS

CROSS-REFERENCE

This application claims the benefit of U.S. Provisional Patent Application No. 62/265,291, filed Dec. 9, 2015, which application is incorporated herein by reference in its entirety.

STATEMENT REGARDING FEDERALLY SPONSORED RESEARCH

This invention was made with government support under contract number NS087159 awarded by the National Institutes of Health. The government has certain rights in the invention.

INTRODUCTION

Functional studies of neuronal tissues involve stimulating one or more neurons with a defined stimulus and measuring the output response of the one or more neurons. Methods of stimulating neurons and measuring the output response include optogenetics, functional magnetic resonance imaging (fMRI), electrophysiology, electroencephalography (EEG) and behavioral monitoring.

Optogenetics uses light-activated polypeptides (channels and pumps) to modulate activity of neurons expressing the light-activated polypeptides in a light-dependent manner.

Blood oxygenation level-dependent (BOLD) fMRI is a widely used technology for non-invasive whole brain imaging. BOLD signals reflect complex changes in cerebral blood flow (CBF), cerebral blood volume (CBV), and cerebral metabolic rate of oxygen consumption ($CMRO_2$) following neuronal activity.

SUMMARY

Provided herein are methods for analyzing, in vivo, a brain circuit. A method of the present disclosure may include using optogenetics to stimulate a first region of a brain of an individual, in conjunction with functional magnetic resonance imaging (fMRI) of different regions of the brain to determine a dynamic functional connection between individual neurons of the first region and a second region of the brain. The method may further include identifying a third region of the brain, the neurons of which region mediate the dynamic functional connection between the first and second regions.

BRIEF DESCRIPTION OF THE DRAWINGS

FIGS. 1A-1G are a collection of images, graphs and diagrams showing that targeted stimulation of central thalamus evokes positive blood oxygenation level-dependent (BOLD) changes and increases in neuronal firing at the site of stimulation, according to embodiments of the present disclosure.

FIGS. 2A-2H are a collection of images and graphs showing the spatial characterization of evoked fMRI signals, according to embodiments of the present disclosure.

FIGS. 5A-5I are a collection of images, graphs and diagrams showing that cortical inhibition driven by 10 Hz central thalamus stimulation depends on normal incertal processing, according to embodiments of the present disclosure.

FIG. 14 shows the amino acid sequences of depolarizing light-activated polypeptides and derivatives thereof (SEQ ID NOs:1-20) that may find use in the present methods, according to embodiments of the present disclosure.

FIG. 15 shows the amino acid sequences of hyperpolarizing light-activated polypeptides and derivatives thereof (SEQ ID NOs:21-51) that may find use in the present methods, according to embodiments of the present disclosure.

DEFINITIONS

Figure 1A:
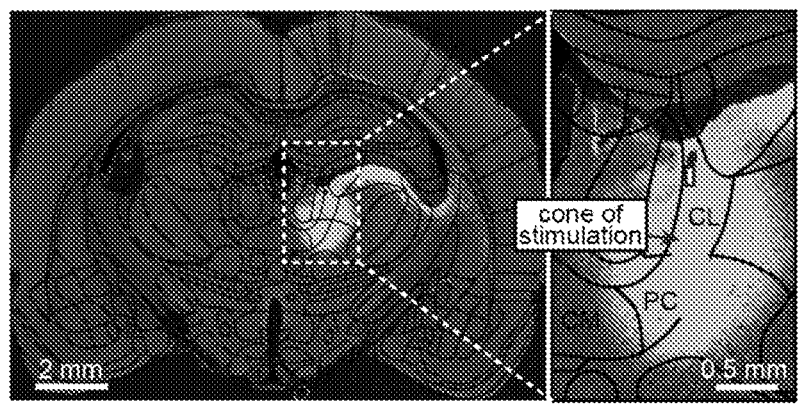

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Substantially" as used herein, may be applied to modify any quantitative representation that could permissibly vary without resulting in a change in the basic function to which it is related.

An "individual" as used herein, may be any suitable animal amenable to the methods and techniques described herein, where in some cases, the individual may be a vertebrate animal, including a mammal, bird, reptile, amphibian, etc. The individual may be any suitable mammal, e.g., human, mouse, rat, cat, dog, pig, horse, cow, monkey, non-human primate, etc.

A "set", as used herein, may include one or more elements.

"Functional", as used herein, may be used to describe a process that is physiologically relevant, i.e., relevant for carrying out a process that normally occurs in a living organism. The process may be a measured phenomenon that is representative of, or a direct or indirect read out of, an underlying, physiologically relevant process.

A "connection" as used herein, may refer to a structural and/or functional relationship between two distinct entities, e.g., cells (including neurons), regions of a tissue (such as regions of a brain), tissues, organs, etc. A functional connection between two regions of the brain may be achieved by direct and/or indirect structural connections (e.g., synaptic connections) between the two regions.

"Neural activity" as used herein, may refer to electrical activity of a neuron (e.g., changes in membrane potential of the neuron), as well as indirect measures of the electrical activity of one or more neurons. Thus, neural activity may refer to changes in field potential, changes in intracellular ion concentration (e.g., intracellular calcium concentration), and changes in magnetic resonance induced by electrical activity of neurons, as measured by, e.g., blood oxygenation level dependent (BOLD) signals in functional magnetic resonance imaging.

"Dynamic" as used herein, may be applied to describe a process that varies in the temporal dimension.

"Quantitative" as used herein, refers to a numerical property defined by or is related to magnitude, or to describe a system (e.g., brain circuit) whose output varies with different patterns of input.

"Qualitative" as used herein, may refer to a property that is not defined by the magnitude of a numerical quantity. For instance, a qualitative determination may include determinations in which a yes/no or on/off result is determined.

"Internal" as used herein, refers to any portion of a body that is not visually or optically accessible from outside the exterior surface of the body. In certain cases, the portion may be below the surface of the body at a depth of 0.1 mm or more.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a neuron" includes a plurality of such neurons and reference to "the light-activated polypeptide" includes reference to one or more light-activated polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of

DETAILED DESCRIPTION

Provided herein are methods for analyzing in vivo a brain circuit. A method of the present disclosure may include using optogenetics to stimulate a first region of a brain of an individual, in conjunction with functional magnetic resonance imaging (fMRI) scanning of different regions of the brain to determine a dynamic functional connection between individual neurons of the first region and a second region of the brain. The method may further include identifying a third region of the brain, the neurons of which region mediate the dynamic functional connection between the first and second regions, using optogenetic stimulation in combination with electrophysiological recording. The present methods can be applied to any suitable brain circuit to reveal functional connections between different regions of the brain at the cellular level, e.g., functional connections between specifically activated neurons of one region, neurons of a second region dynamically regulated by the activated neurons, and neurons of a third region that mediates the dynamic regulation.

Methods

Methods of the present disclosure may use any number of combinations of suitable neuronal stimulation and neuronal activity measurement protocols, as necessary, to determine the functional connections between different brain regions. Suitable protocols include electrophysiology; light-induced modulation of neural activity; electroencephalography (EEG) recordings; functional imaging and behavioral analysis. Electrophysiology may include single electrode, multi electrode, and/or field potential recordings. Light-induced modulation of neural activity may include any suitable optogenetic method, as described further herein. Functional imaging may include fMRI, and any functional imaging protocols using genetically encoded indicators (e.g., calcium indicators, voltage indicators, etc.). Behavioral analysis may include any suitable behavioral assays, such as behavioral assays for arousal, memory (such as a water maze assay), conditioning (such as fear conditioning), sensory responses (responses to e.g., visual, somatosensory, auditory, gustatory, and/or olfactory cues).

Some protocols, such as fMRI, provide a non-invasive, brain-wide measure representative of neural activity. Some protocols, such as electrophysiology, provide cellular resolution and rapid measures of neural activity as well as cellular resolution and rapid control of neural activity. Some protocols, such as optogenetics, provide spatially-targeted and temporally-defined control of action potential firing in defined groups of neurons. An appropriate combination of assays may be used to dissect a functional brain circuit. In some cases, the combination includes: optogenetics and fMRI; optogenetics and electrophysiology; optogenetics and EEG; optogenetics and behavioral analysis. Any other suitable combination, e.g., EEG and behavioral analysis; fMRI and electrophysiology; electrophysiology and behavioral analysis, etc., may also be used.

The methods disclosed herein are amenable to revealing causal links between different brain regions in a single living individual (e.g., a single mouse or rat, a single human, a single non-human mammal) by using one or more different combinations of neuronal stimulation and activity measurement protocols, as described above. Thus, in some embodiments, a brain functional circuit is assayed in a single animal using one or more combinations of optogenetics and fMRI; optogenetics and electrophysiology; optogenetics and EEG; and optogenetics and behavioral analysis. In some cases, a brain functional circuit is assayed in a single animal using all of optogenetics and fMRI; optogenetics and electrophysiology; optogenetics and EEG; and optogenetics and behavioral analysis. The order in which the different combinations of assays are performed on a single animal may be any suitable order. In some cases, the combinations of assays are performed in the order of: optogenetics and fMRI; optogenetics and EEG/optogenetics and behavioral analysis; and optogenetics and electrophysiology, where the pairs "optogenetics and EEG" and "optogenetics and behavioral" may be performed in any order. Other combinations of protocols may be performed at any suitable point before or after any of the combinations of protocols with optogenetics.

In general terms, an implementation of the present method may include using a combination of optogenetic stimulation of a defined set of neurons in a first region of the brain, and measuring the response at a whole-brain level by scanning the brain with fMRI, to determine a dynamic functional connection between the first region and a second region of the brain. Thus, the neurons in the first region may be modified to contain a light-activated polypeptide, e.g., a light-activated ion channel, where the light-activated polypeptide is configured to modulate the activity of, e.g., depolarize or hyperpolarize, the neuron upon stimulating the first region with a light stimulus of appropriate wavelength, illumination volume and intensity. In some cases, the neurons of the first region express the light-activated polypeptide. In some cases, the neurons of the first region are genetically modified, e.g., by viral infection of a DNA construct containing nucleotide sequences encoding the light-activated polypeptide and any other appropriate regulatory elements, to express the light-activated polypeptide. Any suitable light-activated polypeptide may be used, as described further herein.

The light stimulus used to activate the light-activated polypeptide may include light pulses characterized by, e.g., frequency, pulse width, duty cycle, wavelength, intensity, etc. In some cases, the light stimulus includes two or more different sets of light pulses, where each set of light pulses is characterized by different temporal patterns of light pulses. The temporal pattern may be characterized by any suitable parameter, including, but not limited to, frequency, period (i.e., total duration of the light stimulus), pulse width, duty cycle, etc.

The variation in the property of the light pulses of a set may be reflected in a difference in the activity of the illuminated neurons. In some cases, where the neuron is depolarized by activation of the light-activated polypeptide, an increase in the frequency of the light pulses may cause an increase in the frequency of action potential firing in the illuminated neurons. In some embodiments, the frequency of action potential firing in the illuminated neurons scales quantitatively with the increase in the frequency of the light pulses. In some cases, a linear increase in the frequency of the light pulses may induce a linear, or non-linear but monotonic, increase in the frequency of action potential firing in the illuminated neurons.

The responses to the stimulation by different sets of light pulses may be measured by fMRI for different regions of the brain, and a comparison of the responses in each region may indicate a functional connection between neurons stimulated by the light stimulus to the first region and one or more other regions of the brain. In some cases, where the light stimulus contains sets of light pulses that differ quantitatively by a temporal parameter (e.g., varies by frequency or pulse width), a response to the light stimulus in a second region of the brain, as measured by fMRI, that is not linear (e.g., an increase in the action potential firing frequency of excitatory neurons in the first region does not lead to a corresponding increase in the response in the second region) may indicate that there is a functional connection between neurons of the first region and neurons of the second region dependent on the temporal pattern of action potential firing of the neurons of the first region. The non-linear relationship between the variation in the light pulses and the variation in the fMRI response may be a non-monotonic or a qualitative relationship. In some cases, a quantitative change in the light pulse may cause a change in sign of the fMRI blood oxygenation level-dependent (BOLD) response (e.g., a positive or negative BOLD response is measured depending on the frequency of the light pulses).

For example, upon illuminating a first region of the brain with a first set of light pulses and a second set of light pulses that have a different temporal pattern, neurons in the first region may generate action potentials induced by the first set and second set of light pulses. fMRI can then be used to measure activity in a second region of the brain. In some cases, a first change in neural activity induced by the first set of light pulses in the second region can be measured by fMRI. In addition, a second change in neural activity induced by the second set of light pulses in the second region can also be measured by fMRI. In some instances, there may be a difference between the first measured change in neural activity and the second measured change in neural activity. Based on the difference between the first measured change in neural activity and the second measured change in neural activity, a dynamic functional connection between the neurons in the first region of the brain and the second region of the brain may be identified. For instance, the dynamic functional connection between the neurons in the first region of the brain and the second region of the brain may be identified by calculating a difference between the first measured change and the second measured change in neural activity. If the calculated difference between the first measured change and the second measured change in neural activity is qualitatively or quantitatively different, this may be an indication that there is a dynamic functional connection from the neurons in the first region of the brain to the neurons in the second region of the brain.

In some cases, the light stimulus contains two sets of light pulses, where the two sets are characterized by having different parameter values, such as different frequencies of light pulses. Where the two sets of light pulses have different frequencies, the duty cycle may be the same, or may be different. In some cases, the two sets of light pulses with different frequencies have the same pulse width. In other instances, the two sets of light pulses with different frequencies have different pulse widths.

The light pulses of a set may have any suitable frequency. In some cases, the set of light pulses contains a single pulse of light that is sustained throughout the duration of the light stimulus. In some cases, the light pulses of a set have a frequency of 0.1 Hz or more, e.g., 0.5 Hz or more, 1 Hz or more, 5 Hz or more, 10 Hz or more, 20 Hz or more, 30 Hz or more, 40 H or more, including 50 Hz or more, or 60 Hz or more, or 70 Hz or more, or 80 Hz or more, or 90 Hz or more, or 100 Hz or more, and have a frequency of 100,000 Hz or less, e.g., 10,000 Hz or less, 1,000 Hz or less, 500 Hz or less, 400 Hz or less, 300 Hz or less, 200 Hz or less, including 100 Hz or less. In some cases, the light pulses of a set have a frequency in the range of 0.1 to 100,000 Hz, e.g., 1 to 10,000 Hz, 1 to 1,000 Hz, including 5 to 500 Hz, or 10 to 100 Hz.

In some cases, the two sets of light pulses are characterized by having different parameter values, such as different pulse widths. Where the two sets of light pulses have different pulse widths, the duty cycles of the two sets of light pulses may be the same, or may be different. In some cases, the two sets of light pulses with different pulse widths have the same frequency. In other instances, the two sets of light pulses with different pulse widths have different frequencies.

The light pulses may have any suitable pulse width. In some cases, the pulse width is 0.1 ms or longer, e.g., 0.5 ms or longer, 1 ms or longer, 3 ms or longer, 5 ms or longer, 7.5 ms or longer, 10 ms or longer, including 15 ms or longer, or 20 ms or longer, or 25 ms or longer, or 30 ms or longer, or 35 ms or longer, or 40 ms or longer, or 45 ms or longer, or 50 ms or longer, and is 500 ms or shorter, e.g., 100 ms or shorter, 90 ms or shorter, 80 ms or shorter, 70 ms or shorter, 60 ms or shorter, 50 ms or shorter, 45 ms or shorter, 40 ms or shorter, 35 ms or shorter, 30 ms or shorter, 25 ms or shorter, including 20 ms or shorter. In some embodiments, the pulse width is in the range of 0.1 to 500 ms, e.g., 0.5 to 100 ms, 1 to 80 ms, including 1 to 60 ms, or 1 to 50 ms, or 1 to 30 ms.

In some cases, the two sets of light pulses are characterized by having different parameter values, such as different duty cycles. The duty cycle is a percentage (or ratio) related to the "on time" for a pulsed signal and can be calculated as follows:

$$\text{duty cycle} = (\text{pulse width})/\text{frequency}.$$

Where the two sets of light pulses have different duty cycles, the pulse width and/or the frequency of the two sets of light pulses may be the same, or may be different. In some cases, the two sets of light pulses with different duty cycles have different pulse widths and different frequencies. In other instances, the two sets of light pulses with different duty cycles have different pulse widths and the same frequency. In other instances, the two sets of light pulses with different duty cycles have the same pulse width and different frequencies.

In some cases, the two sets of light pulses are characterized by having the same duty cycle. Where the two sets of light pulses have the same duty cycle, the pulse width and/or the frequency of the two sets of light pulses may be different. In some cases, the two sets of light pulses with the same duty cycle have different pulse widths and different frequencies.

The duty cycle of the pulses may be any suitable duty cycle. In some cases, the duty cycle is 1% or more, e.g., 5% or more, 10% or more, 15% or more, 20% or more including 25% or more, or 30% or more, or 35% or more, or 40% or more, or 45% or more, or 50% or more, and may be 80% or less, e.g., 75% or less, 70% or less, 65% or less, 60% or less, 65% or less, 50% or less, 45% or less, including 40% or less, or 35% or less, or 30% or less. In certain embodiments, the duty cycle is in the range of 1 to 80%, e.g., 5 to 70%, 5 to 60%, including 10 to 50%, or 10 to 40%.

The average power of the light pulse, measured at the tip of an optical fiber delivering the light pulse to regions of the brain, may be any suitable power. In some cases, the power is 0.1 mW or more, e.g., 0.5 mW or more, 1 mW or more, 1.5 mW or more, including 2 mW or more, or 2.5 mW or more, or 3 mW or more, or 3.5 mW or more, or 4 mW or more, or 4.5 mW or more, or 5 mW or more, and may be 1,000 mW or less, e.g., 500 mW or less, 250 mW or less, 100 mW or less, 50 mW or less, 40 mW or less, 30 mW or less, 20 mW or less, 15 mW or less, including 10 mW or less, or 5 mW or less. In some embodiments, the power is in the range of 0.1 to 1,000 mW, e.g., 0.5 to 100 mW, 0.5 to 50 mW, 1 to 20 mW, including 1 to 10 mW, or 1 to 5 mW.

The wavelength and intensity of the light pulses may vary and may depend on the activation wavelength of the light-activated polypeptide, optical transparency of the region of the brain, the desired volume of the brain to be illuminated, etc.

The volume of a brain region illuminated by the light pulses may be any suitable volume. In some cases, the illuminated volume is 0.001 mm$^3$ or more, e.g., 0.005 mm$^3$ or more, 0.001 mm$^3$ or more, 0.005 mm$^3$ or more, 0.01 mm$^3$ or more, 0.05 mm$^3$ or more, including 0.1 mm$^3$ or more, and is 100 mm$^3$ or less, e.g., 50 mm$^3$ or less, 20 mm$^3$ or less, 10 mm$^3$ or less, 5 mm$^3$ or less, 1 mm$^3$ or less, including 0.1 mm$^3$ or less. In certain cases, the illuminated volume is in the range of 0.001 to 100 mm$^3$, e.g., 0.005 to 20 mm$^3$, 0.01 to 10 mm$^3$, 0.01 to 5 mm$^3$, including 0.05 to 1 mm$^3$.

Another aspect of the present methods includes identifying neurons in a third region of the brain that may mediate the dynamic functional connection between the first and second regions, as described above. Thus, the neurons of the third region may be said to represent a node, e.g., a modulatory node, of the dynamic functional connection between the first and second regions, where the neurons of the third region have functional connections to both the first and second regions. In some cases, identifying a modulatory node of the dynamic functional connection may include using one or more of electrophysiology; light-induced modulation of neural activity; EEG; functional imaging (e.g., fMRI) and behavioral analysis, as described above.

In some embodiments, neurons in a third region of the brain that may mediate the dynamic functional connection between the first and second regions may be identified by measuring the effect of disrupting the normal activity of the neurons of the third region on the dynamic properties of the functional connection between neurons of the first and second regions. If normal activity of the neurons of the third region is required for the dynamic functional connection, then the neurons of the third region may represent a modulatory node for the dynamic functional connection.

The normal activity of the neurons of the third region may be disrupted using any suitable method. In some cases, the activity is disrupted by activating a light-activated polypeptide, e.g., a light-activated ion pump for a normally activated neuron, in the neurons of the third region, via illumination of the third region with an appropriate light stimulus for activating the light-activated polypeptide. By comparing the change in response of neurons in the second region to a first set of light pulses that activates light-activated polypeptides in neurons of the first region, in the presence or absence of a third set of light pulses illuminating the third region, the role of the neurons of the third region in the dynamic functional connection between the first and second regions may be determined. Thus, if illumination of the third region to disrupt the normal activity of neurons of the third region reduces, abolishes or otherwise alters the response of the neurons in the second region to the first set of light pulses, the neurons of the third region may mediate the dynamic functional connection. In some cases, the response of the neurons in the second region to the first set of light pulses may be reduced by 20% or more, e.g., 30% or more, 40% or more, 50% or more, 60% or more, 70% or more, 80% or more, 90% or more, and up to 100%. In some cases, the response of the neurons in the second region to the first set of light pulses may include a change in sign (e.g., a reduction in firing rate with normal activity of neurons of the third region is switched to an increase in firing rate with disruption of normal activity of neurons of the third region).

For example, the presence or absence of a modulatory node in the third region of the brain may be determined by illuminating the first region of the brain (which has a dynamic functional connection to the second region of the brain) with and without illumination of the third region of the brain with a set of light pulses. Upon illuminating the first region of the brain with a first set of light pulses, neurons in the first region may generate action potentials induced by the first set of light pulses. In addition, the third region of the brain may be concurrently illuminated with a third set of light pulses. Upon illumination of the third region, the activity of neurons in the third region may be disrupted, for example if neurons in the third region express a light-activated polypeptide as described herein. Neural activity may then be measured (e.g., fMRI) in the second region of the brain, which has a dynamic functional connection to the first region of the brain. For instance, fMRI can be used to measure a third change in neural activity induced by the first set of light pulses in the second region of the brain without illumination of the third region of the brain. In some cases, the third measured change in neural activity induced by the first set of light pulses in the second region of the brain without illumination of the third region of the brain provides a baseline measurement of the dynamic functional connection between the first region and the second region of the brain. In addition, a fourth change in neural activity induced by the first set of light pulses in the second region can also be measured while the third region of the brain is being illuminated by a third set of light pulses. In some instances, there may be a difference between the third measured change in neural activity and the fourth measured change in neural activity. Based on the difference between the third measured change in neural activity and the fourth measured change in neural activity, a modulatory node in the third region of the brain may be identified. The presence of a modulatory node in the third region of the brain may be an indication of a functional connection between the third region of the brain and the first region of the brain and/or a functional connection between the third region of the brain and the second region of the brain. For instance, the modulatory node in the third region of the brain may be identified by calculating a difference between the third measured change and the fourth measured change in neural activity. If the calculated difference between the third measured change and the fourth measured change in neural activity is qualitatively or quantitatively different, this may be an indication that there is a modulatory node in the third region of the brain. For example, if the calculated difference between the third measured change and the fourth measured change in neural activity is qualitatively or quantitatively different, this may be an indication that there is a functional connection between the third region of the brain and the first region of the brain and/or a functional connection between the third region of the brain and the second region of the brain.

Optogenetic stimulation may be performed using any suitable method. Suitable methods are described in, e.g., U.S. Pat. No. 8,834,546, which is incorporated herein by reference. Neurons of a suitable region of the brain whose activity is to be modulated by light can be modified using a convenient method to express the light-activated polypeptide. In some cases, neurons of a brain region are genetically modified to express a light-activated polypeptide. In some cases, the neurons may be genetically modified using a viral vector, e.g., an adeno-associated viral vector, containing a nucleic acid having a nucleotide sequence that encodes the light-activated polypeptide. The viral vector may include any suitable control elements (e.g., promoters, enhancers, recombination sites, etc.) to control expression of the light-activated polypeptide according to cell type, timing, presence of an inducer, etc.

Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) *Cell* 51:7-19; and Llewellyn et al. (2010) *Nat. Med.* 16:1161); a serotonin receptor promoter (see, e.g., GenBank S62283); a tyrosine hydroxylase promoter (TH) (see, e.g., *Nucl. Acids. Res.* 15:2363-2384 (1987) and *Neuron* 6:583-594 (1991)); a GnRH promoter (see, e.g., Radovick et al., *Proc. Natl. Acad. Sci. USA* 88:3402-3406 (1991)); an L7 promoter (see, e.g., Oberdick et al., *Science* 248:223-226 (1990)); a DNMT promoter (see, e.g., Bartge et al., *Proc. Natl. Acad. Sci. USA* 85:3648-3652 (1988)); an enkephalin promoter (see, e.g., Comb et al., *EMBO J.* 17:3793-3805 (1988)); a myelin basic protein (MBP) promoter; a CMV enhancer/platelet-derived growth factor-β promoter (see, e.g., Liu et al. (2004) *Gene Therapy* 11:52-60); a motor neuron-specific gene Hb9 promoter (see, e.g., U.S. Pat. No. 7,632,679; and Lee et al. (2004) *Development* 131:3295-3306); and an alpha subunit of $Ca^{2+}$-calmodulin-dependent protein kinase II (CaMKIIα) promoter (see, e.g., Mayford et al. (1996) *Proc. Natl. Acad. Sci. USA* 93:13250). Other suitable promoters include elongation factor (EF) 1α and dopamine transporter (DAT) promoters.

In some cases, cell type-specific expression of the light-activated polypeptide may be achieved by using recombination systems, e.g., Cre-Lox recombination, Flp-FRT recombination, etc. Cell type-specific expression of genes using recombination has been described in, e.g., Fenno et al., *Nat Methods.* 2014 July; 11(7):763; and Gompf et al., *Front Behav Neurosci.* 2015 Jul. 2; 9:152, which are incorporated by reference herein.

In some cases the regions of the brain with neurons containing a light-activated peptide, is illuminated using one or more optical fibers. The optical fiber may be configured in any suitable manner to direct a light emitted from suitable source of light, e.g., a laser or light-emitting diode (LED) light source, to the region of the brain. The optical fiber may be any suitable optical fiber. In some cases, the optical fiber is a multimode optical fiber. The optical fiber may include a core defining a core diameter, where light from the light source passes through the core. The optical fiber may have any suitable core diameter. In some cases, the core diameter of the optical fiber is 10 µm or more, e.g., 20 µm or more, 30 µm or more, 40 µm or more, 50 µm or more, 60 µm or more, including 80 µm or more, and is 1,000 µm or less, e.g., 500 µm or less, 200 µm or less, 100 µm or less, including 70 µm or less. In some embodiments, the core diameter of the optical fiber is in the range of 10 to 1,000 µm, e.g., 20 to 500 µm, 30 to 200 µm, including 40 to 100 µm.

In certain embodiments, a cladding surrounds at least a portion of the core of the optical fiber. For instance, the cladding may surround substantially the entire outer circumferential surface of the optical fiber. In some cases, the cladding is not present on the ends of the optical fiber, such as at the end of the optical fiber that receives light from the light source, and the opposite end of the optical fiber that transmits light to the neurons in the target region of the brain. The cladding may be any suitable type of cladding. In some cases, the cladding has a lower refractive index than the core of the optical fiber. Suitable materials for the cladding include, but are not limited to, plastic, resin, and the like, and combinations thereof.

In some cases, the optical fiber includes an outer coating. The outer coating may be disposed on the surface of the cladding. The coating may surround substantially the entire outer circumferential surface of the optical fiber. In some cases, the coating is not present on the ends of the optical fiber, such as at the end of the optical fiber that receives light from the light source, and the opposite end of the optical fiber that transmits light to the neurons in the target region of the brain. The coating may be a biologically compatible coating. A biologically compatible coating includes coatings that do not significantly react with tissues, fluids, or other substances present in the subject into which the optical fiber is inserted. In some cases, a biologically compatible coating is composed of a material that is inert (i.e., substantially non-reactive) with respect to the surrounding environment in which the optical fiber is used.

The optical fiber end that is implanted into the target region of the brain may have any suitable configuration suitable for illuminating a region of the brain with a light stimulus delivered through the optical fiber. In some cases, the optical fiber includes an attachment device at or near the distal end of the optical fiber, where the distal end of the optical fiber corresponds to the end inserted into the subject. In some cases, the attachment device is configured to connect to the optical fiber and facilitate attachment of the optical fiber to the subject, such as to the skull of the subject. Any suitable attachment device may be used. In some cases, the attachment device includes a ferrule, e.g., a metal, ceramic or plastic ferrule. The ferrule may have any suitable dimensions for holding and attaching the optical fiber. In some cases, the ferrule has a diameter in the range of 0.5 to 3 mm, e.g., 0.75 to 2.5 mm, or 1 to 2 mm.

In certain embodiments, methods of the present disclosure may be performed using any suitable electronic components to control and/or coordinate the various optical components used to illuminate the regions of the brain. The optical components (e.g., light source, optical fiber, lens, objective, mirror, and the like) may be controlled by a controller, e.g., to coordinate the light source illuminating the regions of the brain with light pulses. The controller may include a driver for the light source that controls one or more parameters associated with the light pulses, such as, but not limited to the frequency, pulse width, duty cycle, wavelength, intensity, etc. of the light pulses. The controllers may be in communication with components of the light source (e.g., collimators, shutters, filter wheels, moveable mirrors, lenses, etc.).

A computational unit (e.g., a computer) may be used in the methods of the present disclosure to control and/or coordinate the light stimulus through the one or more controllers, and to analyze data from fMRI scanning of the regions of the brain. A computational unit may include any suitable components to analyze the measured fMRI images. Thus, the computational unit may include one or more of the following: a processor; a non-transient, computer-readable memory, such as a computer-readable medium; an input device, such as a keyboard, mouse, touchscreen, etc.; an output device, such as a monitor, screen, speaker, etc.; a network interface, such as a wired or wireless network interface; and the like.

fMRI may be performed using any suitable method. Suitable methods are described in, e.g., U.S. Pat. No. 8,834,546, which is incorporated herein by reference.

The brain regions of interest in the present methods (for optogenetically stimulating and/or measuring neural activity) may vary and may be any suitable region. In certain embodiments, the brain regions are anatomically and/or functionally defined regions of the brain. For example, the first region of the brain and the second region of the brain illuminated by light pulses as described herein may be anatomically distinct regions of the brain. Similarly, in some instances, the third region of the brain, which modulates the dynamic functional connection between the first and second regions, may be anatomically distinct from the first region and the second region of the brain. In some cases, where the brain is a mammalian brain, the brain region of interest is selected from at least a portion of the thalamus (including the central thalamus), sensory cortex (including the somatosensory cortex), zona incerta (ZI), ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyms, entorhinal cortex, olfactory cortex, primary motor cortex, and cerebellum. In some cases, different brain regions (e.g., the first and second brain regions) are separated at minimum by one or more, e.g., 2 or more, 3 or more, 4 or more, 5 or more, including 7 or more synaptic connections, and are separated at minimum by 15 or fewer, e.g., 12 or fewer, 10 or fewer, 8 or fewer, including 6 or fewer synaptic connections. In some embodiments, the different brain regions are separated at minimum by 1 to 15 synaptic connections, e.g., 1 to 12 synaptic connections, 1 to 10 synaptic connections, 2 to 8 synaptic connections, including 3 to 6 synaptic connections.

Neurons of interest and that are present in the brain regions may be any suitable types of neurons. In some cases, the neurons are inhibitory neurons, or excitatory neurons. In some cases, the neurons are sensory neurons, interneurons, or motor neurons. In some cases, the neurons are, without limitation, dopaminergic, cholinergic, GABAergic, glutamatergic, or peptidergic neurons.

Light-Activated Polypeptides

As summarized above, aspects of the present disclosure include various brain regions containing neurons with, e.g., expressing, a light-activated polypeptide. The light-activated polypeptide may be a light-activated ion channel or a light-activated ion pump. The light-activated ion channel polypeptides are adapted to allow one or more ions to pass through the plasma membrane of a neuron when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-activated polypeptide depolarizes the neuron when activated by light of an activating wavelength. Suitable depolarizing light-activated polypeptides, without limitation, are shown in FIG. 14. In some embodiments, the light-activated polypeptide hyperpolarizes the neuron when activated by light of an activating wavelength. Suitable hyperpolarizing light-activated polypeptides, without limitation, are shown in FIG. 15.

In some embodiments, the light-activated polypeptides are activated by blue light. In some embodiments, the light-activated polypeptides are activated by green light. In some embodiments, the light-activated polypeptides are activated by yellow light. In some embodiments, the light-activated polypeptides are activated by orange light. In some embodiments, the light-activated polypeptides are activated by red light.

In some embodiments, the light-activated polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-activated protein transport to the plasma membranes of mammalian cells can be fused to the N-terminus, the C-terminus, or to both the N- and C-terminal ends of the light-activated polypeptide. In some cases, the one or more amino acid sequence motifs which enhance light-activated polypeptide transport to the plasma membranes of mammalian cells is fused internally within a light-activated polypeptide. Optionally, the light-activated polypeptide and the one or more amino acid sequence motifs may be separated by a linker.

In some embodiments, the light-activated polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

ER export sequences that are suitable for use with a light-activated polypeptide include, e.g., VXXSL (where X is any amino acid; SEQ ID NO:52) (e.g., VKESL (SEQ ID NO:53); VLGSL (SEQ ID NO:54); etc.); NANSFCY-ENEVALTSK (SEQ ID NO:55); FXYENE (SEQ ID NO:57) (where X is any amino acid), e.g., FCYENEV (SEQ ID NO:58); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

Signal sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such as one of the following: 1) the signal peptide of hChR2 (e.g., MDYGGALSAVGRELLFVTNPVVVNGS (SEQ ID NO:59)); 2) the β2 subunit signal peptide of the neuronal nicotinic acetylcholine receptor (e.g., MAGHSNSMALF-SFSLLWLCSGVLGTEF (SEQ ID NO:60)); 3) a nicotinic acetylcholine receptor signal sequence (e.g., MGL-RALMLWLLAAAGLVRESLQG (SEQ ID NO:64)); and 4) a nicotinic acetylcholine receptor signal sequence (e.g., MRGTPLLLVVSLFSLLQD (SEQ ID NO:61)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

In some embodiments, the signal peptide sequence in the protein can be deleted or substituted with a signal peptide sequence from a different protein.

Examples of light-activated polypeptides are described in, e.g., PCT App. No. PCT/US2011/028893, which is incorporated herein by reference. Representative light-activated polypeptides that find use in the present disclosure are further described below.

Depolarizing Light-Activated Polypeptides
ChR

In some aspects, a depolarizing light-activated polypeptide is derived from Chlamydomonas reinhardtii, wherein the polypeptide is capable of transporting cations across a cell membrane when the cell is illuminated with light. In another embodiment, the light-activated polypeptide comprises an amino acid sequence at least 75%, 85%, 90%, 91%, 92%, 93%, 94%, 95%, 96%, 97%, 98%, 99%, or 100% identical to the sequence shown in SEQ ID NO:1. The light used to activate the light-activated cation channel protein derived from Chlamydomonas reinhardtii can have a wavelength between about 460 and about 495 nm or can have a wavelength of about 480 nm. Additionally, light pulses having a temporal frequency of about 100 Hz can be used to activate the light-activated protein. In some embodiments, activation of the light-activated cation channel derived from Chlamydomonas reinhardtii with light pulses having a temporal frequency of about 100 Hz can cause depolarization of the neurons expressing the light-activated cation channel. The light-activated cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-activated cation channel protein to regulate the polarization state of the plasma membrane of the cell. Additionally, the light-activated cation channel protein can comprise one or more conservative amino acid substitutions and/or one or more non-conservative amino acid substitutions. The light-activated proton pump protein containing substitutions, deletions, and/or insertions introduced into the native amino acid sequence suitably retains the ability to transport cations across a cell membrane.

In some embodiments, the light-activated cation channel includes a T159C substitution of the amino acid sequence set forth in SEQ ID NO:1. In some embodiments, the light-activated cation channel includes a L132C substitution of the amino acid sequence set forth in SEQ ID NO:1. In some embodiments, the light-activated cation channel includes an E123T substitution of the amino acid sequence set forth in SEQ ID NO:1. In some embodiments, the light-activated cation channel includes an E123A substitution of the amino acid sequence set forth in SEQ ID NO:1. In some embodiments, the light-activated cation channel includes a T159C substitution and an E123T substitution of the amino acid sequence set forth in SEQ ID NO:1. In some embodiments, the light-activated cation channel includes a T159C substitution and an E123A substitution of the amino acid sequence set forth in SEQ ID NO:1. In some embodiments, the light-activated cation channel includes a T159C substitution, an L132C substitution, and an E123T substitution of the amino acid sequence set forth in SEQ ID NO:1. In some embodiments, the light-activated cation channel includes a T159C substitution, an L132C substitution, and an E123A substitution of the amino acid sequence set forth in SEQ ID NO:1. In some embodiments, the light-activated cation channel includes an L132C substitution and an E123T substitution of the amino acid sequence set forth in SEQ ID NO:1. In some embodiments, the light-activated cation channel includes an L132C substitution and an E123A substitution of the amino acid sequence set forth in SEQ ID NO:1.

In some embodiments, a ChR2 protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the ChR2 protein comprises an N-terminal signal peptide and a C-terminal ER export signal. In some embodiments, the ChR2 protein comprises an N-terminal signal peptide and a C-terminal trafficking signal. In some embodiments, the ChR2 protein comprises an N-terminal signal peptide, a C-terminal ER export signal, and a C-terminal trafficking signal. In some embodiments, the ChR2 protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the ChR2 protein can have an amino acid sequence that is at least 75%, 85%, 90%, 91%, 92%, 93%, 94%, 95%, 96%, 97%, 98%, 99%, or 100% identical to the sequence shown in SEQ ID NO:2.

In other embodiments, the light-activated polypeptide is a step function opsin (SFO) protein or a stabilized step function opsin (SSFO) protein that can have specific amino acid substitutions at key positions in the retinal binding pocket of the protein. In some embodiments, the SFO protein can have a mutation at amino acid residue C128 of SEQ ID NO:1. In other embodiments, the SFO protein has a C128A mutation in SEQ ID NO:1. In other embodiments, the SFO protein has a C128S mutation in SEQ ID NO:1. In another embodiment, the SFO protein has a C128T mutation in SEQ ID NO:1.

In some embodiments, the SSFO protein can have a mutation at amino acid residue D156 of SEQ ID NO:1. In other embodiments, the SSFO protein can have a mutation at both amino acid residues C128 and D156 of SEQ ID NO:1. In one embodiment, the SSFO protein has an C128S and a D156A mutation in SEQ ID NO:1. In another embodiment, the SSFO protein can comprise an amino acid sequence at least 75%, 85%, 90%, 91%, 92%, 93%, 94%, 95%, 96%, 97%, 98%, 99%, or 100% identical to the sequence shown in SEQ ID NO:1; and includes an alanine, serine, or threonine at amino acid 128; and includes a alanine at amino acid 156. In another embodiment, the SSFO protein can comprise a C128T mutation in SEQ ID NO:1. In some embodiments, the SSFO protein includes C128T and D156A mutations in SEQ ID NO:1.

In some embodiments the SFO or SSFO proteins provided herein can be capable of mediating a depolarizing current in the cell when the cell is illuminated with blue light. In other embodiments, the light can have a wavelength of about 445 nm. Additionally, in some embodiments the light can be delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970, the disclosure of which is hereby incorporated by reference in its entirety.

In some cases, the ChR2-based SFO or SSFO comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the SSFO protein comprises an amino acid sequence that is at least 75%, 85%, 90%, 91%, 92%, 93%, 94%, 95%, 96%, 97%, 98%, 99%, or 100% identical to the sequence shown in SEQ ID NO:4.

*Volvox Carteri* Light-Activated Polypeptide

In some embodiments, a suitable light-activated polypeptide is a cation channel derived from *Volvox carteri* (VChR1) and is activated by illumination with light of a wavelength of from about 500 nm to about 600 nm, e.g., from about 525 nm to about 550 nm, e.g., 545 nm. In some embodiments, the light-activated ion channel protein comprises an amino acid sequence at least 75%, 85%, 90%, 91%, 92%, 93%, 94%, 95%, 96%, 97%, 98%, 99%, or 100% identical to the sequence shown in SEQ ID NO:5. The light-activated ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-activated ion channel protein to regulate the polarization state of the plasma membrane of the cell. Additionally, the light-activated ion channel protein can comprise one or more conservative amino acid substitutions and/or one or more non-conservative amino acid substitutions. The light-activated ion channel protein containing substitutions, deletions, and/or insertions introduced into the native amino acid sequence suitably retains the ability to transport ions across the plasma membrane of a neuronal cell in response to light.

In some cases, a VChR1 light-activated cation channel protein comprises a core amino acid sequence at least 75%, 85%, 90%, 91%, 92%, 93%, 94%, 95%, 96%, 97%, 98%, 99%, or 100% identical to the sequence shown in SEQ ID NO:5 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-activated proton ion channel comprises an N-terminal signal peptide and a C-terminal ER export signal. In some embodiments, the light-activated ion channel protein comprises an N-terminal signal peptide and a C-terminal trafficking signal. In some embodiments, the light-activated ion channel protein comprises an N-terminal signal peptide, a C-terminal ER Export signal, and a C-terminal trafficking signal. In some embodiments, the light-activated ion channel protein comprises a C-terminal ER Export signal and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the VChR1 protein comprises an amino acid sequence that is at least 75%, 85%, 90%, 91%, 92%, 93%, 94%, 95%, 96%, 97%, 98%, 99%, or 100% identical to the sequence shown in SEQ ID NO:6.

Step Function Opsins and Stabilized Step Function Opsins Based on VChR1

In other embodiments, the light-activated polypeptide is a SFO or an SSFO based on VChR1. In some embodiments, the SFO protein can have a mutation at amino acid residue C123 of SEQ ID NO:5. In other embodiments, the SFO protein has a C123A mutation in SEQ ID NO:5. In other embodiments, the SFO protein has a C123S mutation in SEQ ID NO:5. In another embodiment, the SFO protein has a C123T mutation in SEQ ID NO:5.

In some embodiments, the SFO protein can have a mutation at amino acid residue D151 of SEQ ID NO:5. In other embodiments, the SFO protein can have a mutation at both amino acid residues C123 and D151 of SEQ ID NO:5. In one embodiment, the SFO protein has an C123S and a D151A mutation in SEQ ID NO:5.

In some embodiments an SFO or SSFO protein is capable of mediating a depolarizing current in the cell when the cell is illuminated with blue light. In some embodiments, the light has a wavelength of about 560 nm. Additionally, in some embodiments the light is delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

In some cases, the VChR1-based SFO or SSFO comprises a membrane trafficking signal and/or an ER export signal. In some embodiments, the trafficking signal can be derived from the amino acid sequence of the human inward rectifier potassium channel Kir2.1. Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

C1V1 Chimeric Cation Channels

In other embodiments, the light-activated cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein comprises an amino acid sequence at least 75%, 85%, 90%, 91%, 92%, 93%, 94%, 95%, 96%, 97%, 98%, 99%, or 100% identical to the sequence shown in SEQ ID NO:7.

In some embodiments, the C1V1 protein mediates a depolarizing current in the cell when the cell is illuminated with green light. In some embodiments, the light has a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some cases, the C1V1 polypeptide comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the C1V1 protein comprises an amino acid sequence that is at least 75%, 85%, 90%, 91%, 92%, 93%, 94%, 95%, 96%, 97%, 98%, 99%, or 100% identical to the sequence shown in SEQ ID NO:8.

C1V1 Variants

In some aspects, a suitable light-activated polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-activated C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-activated cation channels, and/or strong expression in animal cells.

Accordingly, suitable light-activated proteins include C1V1 chimeric light-activated proteins that can have specific amino acid substitutions at key positions throughout the retinal binding pocket of the VChR1 portion of the chimeric polypeptide. In some embodiments, the C1V1 protein comprises an amino acid substitution at amino acid residue E122 of SEQ ID NO:7. In some embodiments, the C1V1 protein comprises a substitution at amino acid residue E162 of SEQ ID NO:7. In other embodiments, the C1V1 protein comprises a substitution at both amino acid residues E162 and E122 of SEQ ID NO:7.

In some aspects, the C1V1-E122 mutant chimeric protein is capable of mediating a depolarizing current in the cell when the cell is illuminated with light. In some embodiments the light is green light. In other embodiments, the light has a wavelength of between about 540 nm to about 560 nm. In some embodiments, the light has a wavelength of about 546 nm. In other embodiments, the C1V1-E122 mutant chimeric protein mediates a depolarizing current in the cell when the cell is illuminated with red light. In some embodiments, the red light has a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E122 mutant chimeric protein. In some embodiments, activation of the C1V1-E122 mutant chimeric protein with light pulses having a frequency of 100 Hz can cause depolarization of the neurons expressing the C1V1-E122 mutant chimeric protein.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E162 mutant chimeric protein. In some embodiments, activation of the C1V1-E162 mutant chimeric protein with light pulses having a frequency of 100 Hz can cause depolarization-induced synaptic depletion of the neurons expressing the C1V1-E162 mutant chimeric protein.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-activated cation channel proteins. Additionally, in some embodiments, light pulses having a temporal frequency of about 100 Hz can be used to activate the C1V1-E122/E162 mutant chimeric protein. In some embodiments, activation of the C1V1-E122/E162 mutant chimeric protein with light pulses having a frequency of 100 Hz can cause depolarization-induced synaptic depletion of the neurons expressing the C1V1-E122/E162 mutant chimeric protein.

In some cases, the C1V1 variant polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

C1C2 Chimeric Cation Channels

In other embodiments, the light-activated cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. In another embodiment, the light-activated polypeptide comprises an amino acid sequence at least 75%, 85%, 90%, 91%, 92%, 93%, 94%, 95%, 96%, 97%, 98%, 99%, or 100% identical to the sequence shown in SEQ ID NO:9. The light-activated cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-activated cation channel protein to regulate the polarization state of the plasma membrane of the cell. Additionally, the light-activated cation channel protein comprises one or more conservative amino acid substitutions and/or one or more non-conservative amino acid substitutions. The light-activated proton pump protein containing substitutions, deletions, and/or insertions introduced into the native amino acid sequence suitably retains the ability to transport cations across a cell membrane.

In some embodiments, a C1C2 protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the C1C2 protein comprises an N-terminal signal peptide and a C-terminal ER export signal. In some embodiments, the C1C2 protein comprises an N-terminal signal peptide and a C-terminal trafficking signal. In some embodiments, the C1C2 protein comprises an N-terminal signal peptide, a C-terminal ER export signal, and a C-terminal trafficking signal. In some embodiments, the C1C2 protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the C1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO:10.

ReaChR

In some aspects, a depolarizing light-activated polypeptide is a red shifted variant of a depolarizing light-activated polypeptide derived from *Chlamydomonas reinhardtii*; such light-activated polypeptides are referred to herein as a "ReaChR polypeptide" or "ReaChR protein" or "ReaChR." In another embodiment, the light-activated polypeptide comprises an amino acid sequence at least 75%, 85%, 90%, 91%, 92%, 93%, 94%, 95%, 96%, 97%, 98%, 99%, or 100% identical to the sequence shown in SEQ ID NO:11. The light used to activate the ReaChR polypeptide can have a wavelength between about 590 and about 630 nm or can have a wavelength of about 610 nm. The ReaChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-activated cation channel protein to regulate the polarization state of the plasma membrane of the cell. Additionally, the ReaChR protein can comprise one or more conservative amino acid substitutions and/or one or more non-conservative amino acid substitutions. The ReaChR containing substitutions, deletions, and/or insertions introduced into the native amino acid sequence suitably retains the ability to transport cations across a cell membrane.

In some embodiments, a ReaChR protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the ReaChR protein comprises an N-terminal signal peptide and a C-terminal ER export signal. In some embodiments, the ReaChR protein comprises an N-terminal signal peptide and a C-terminal trafficking signal. In some embodiments, the ReaChR protein comprises an N-terminal signal peptide, a C-terminal ER export signal, and a C-terminal trafficking signal. In some embodiments, the ReaChR protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the ReaChR protein comprises an amino acid sequence that is at least 75%, 85%, 90%, 91%, 92%, 93%, 94%, 95%, 96%, 97%, 98%, 99%, or 100% identical to the sequence shown in SEQ ID NO:12.

SdChR

In some aspects, a depolarizing light-activated polypeptide is a SdChR polypeptide derived from *Scherffelia dubia*, wherein the SdChR polypeptide is capable of transporting cations across a cell membrane when the cell is illuminated with light. In some cases, the SdChR polypeptide comprises an amino acid sequence at least 75%, 85%, 90%, 91%, 92%, 93%, 94%, 95%, 96%, 97%, 98%, 99%, or 100% identical to the sequence shown in SEQ ID NO:13. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane.

In some embodiments, a SdChR protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the SdChR protein comprises an N-terminal signal peptide and a C-terminal ER export signal. In some embodiments, the SdChR protein comprises an N-terminal signal peptide and a C-terminal trafficking signal. In some embodiments, the SdChR protein comprises an N-terminal signal peptide, a C-terminal ER export signal, and a C-terminal trafficking signal. In some embodiments, the SdChR protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the SdChR protein comprises an amino acid sequence that is at least 75%, 85%, 90%, 91%, 92%, 93%, 94%, 95%, 96%, 97%, 98%, 99%, or 100% identical to the sequence shown in SEQ ID NO:14.

CnChR1

In some aspects, a depolarizing light-activated polypeptide can be, e.g. CnChR1, derived from *Chlamydomonas noctigama*, wherein the CnChR1 polypeptide is capable of transporting cations across a cell membrane when the cell is illuminated with light. In some cases, the CnChR1 polypeptide comprises an amino acid sequence at least 75%, 85%, 90%, 91%, 92%, 93%, 94%, 95%, 96%, 97%, 98%, 99%, or 100% identical to the sequence shown in SEQ ID NO:15. The light used to activate the CnChR1 polypeptide can have a wavelength between about 560 and about 630 nm or can have a wavelength of about 600 nm. The CnChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR1 protein to regulate the polarization state of the plasma membrane of the cell. In some cases, the CnChR1 protein comprises one or more conservative amino acid substitutions and/or one or more non-conservative amino acid substitutions. The CnChR1 protein containing substitutions, deletions, and/or insertions introduced into the native amino acid sequence suitably retains the ability to transport cations across a cell membrane.

In some embodiments, a CnChR1protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the CnChR1protein includes an N-terminal signal peptide and a C-terminal ER export signal. In some embodiments, the CnChR1protein includes an N-terminal signal peptide and a C-terminal trafficking signal. In some embodiments, the CnChR1protein comprises an N-terminal signal peptide, a C-terminal ER export signal, and a C-terminal trafficking signal. In some embodiments, the CnChR1protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the CnChR1protein comprises an amino acid sequence that is at least 75%, 85%, 90%, 91%, 92%, 93%, 94%, 95%, 96%, 97%, 98%, 99%, or 100% identical to the sequence shown in SEQ ID NO:16.

CsChrimson

In other embodiments, the light-activated cation channel protein is a CsChrimson chimeric protein derived from a CsChR protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. In another embodiment, the CsChrimson polypeptide comprises an amino acid sequence at least 75%, 85%, 90%, 91%, 92%, 93%, 94%, 95%, 96%, 97%, 98%, 99%, or 100% identical to the sequence shown in SEQ ID NO:17. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell.

Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane.

In some embodiments, a CsChrimson protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the CsChrimson protein comprises an N-terminal signal peptide and a C-terminal ER export signal. In some embodiments, the CsChrimson protein comprises an N-terminal signal peptide and a C-terminal trafficking signal. In some embodiments, the CsChrimson protein comprises an N-terminal signal peptide, a C-terminal ER export signal, and a C-terminal trafficking signal. In some embodiments, the CsChrimson protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the CsChrimson protein comprises an amino acid sequence that is at least 75%, 85%, 90%, 91%, 92%, 93%, 94%, 95%, 96%, 97%, 98%, 99%, or 100% identical to the sequence shown in SEQ ID NO:18.

ShChR1

In some aspects, a depolarizing light-activated polypeptide can be, e.g. ShChR1, derived from *Stigeoclonium helveticum*, wherein the ShChR1 polypeptide is capable of transporting cations across a cell membrane when the cell is illuminated with light. In some cases, the ShChR1 polypeptide comprises an amino acid sequence at least 75%, 85%, 90%, 91%, 92%, 93%, 94%, 95%, 96%, 97%, 98%, 99%, or 100% identical to the sequence shown in SEQ ID NO:19. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane.

In some embodiments, a ShChR1 protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the ShChR1 protein comprises an N-terminal signal peptide and a C-terminal ER export signal. In some embodiments, the ShChR1 protein comprises an N-terminal signal peptide and a C-terminal trafficking signal. In some embodiments, the ShChR1 protein comprises an N-terminal signal peptide, a C-terminal ER export signal, and a C-terminal trafficking signal. In some embodiments, the ShChR1protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the ShChR1 protein comprises an amino acid sequence that is at least 75%, 85%, 90%, 91%, 92%, 93%, 94%, 95%, 96%, 97%, 98%, 99%, or 100% identical to the sequence shown in SEQ ID NO:20.

Other suitable depolarizing light-activated polypeptides are described in, e.g., Klapoetke et al. Nat Methods 2014 11:338.

Hyperpolarizing Light-Activated Polypeptides

Arch

In some embodiments, a suitable light-activated polypeptide is an Archaerhodopsin (Arch) proton pump (e.g., a proton pump derived from *Halorubrum sodomense*) that can transport one or more protons across the plasma membrane of a cell when the cell is illuminated with light. The light can have a wavelength between about 530 and about 595 nm or can have a wavelength of about 560 nm. In some embodiments, the Arch protein comprises an amino acid sequence that is at least 75%, 85%, 90%, 91%, 92%, 93%, 94%, 95%, 96%, 97%, 98%, 99%, or 100% identical to the sequence shown in SEQ ID NO:21. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a neuron. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a neuron in response to light.

In some embodiments, the Arch protein comprises at least one (such as one, two, three, or more) amino acid sequence motifs selected from a signal peptide, an ER export signal, and a membrane trafficking signal, that enhance transport to the plasma membranes of neurons. In some embodiments, the Arch protein comprises an N-terminal signal peptide and a C-terminal ER export signal. In some embodiments, the Arch protein comprises an N-terminal signal peptide and a C-terminal trafficking signal. In some embodiments, the Arch protein comprises an N-terminal signal peptide, a C-terminal ER export signal, and a C-terminal trafficking signal. In some embodiments, the Arch protein includes a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The linker may further include a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal can include the amino acid sequence KSRIT-SEGEYIPLDQIDINV (SEQ ID NO:56). Trafficking sequences that are suitable for use can include an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCY-ENEV (SEQ ID NO:58); and the like.

In certain embodiments, the Arch protein comprises an amino acid sequence that is at least 75%, 85%, 90%, 91%, 92%, 93%, 94%, 95%, 96%, 97%, 98%, 99%, or 100% identical to the sequence shown in SEQ ID NO:22.

ArchT

In some embodiments, a suitable light-activated protein is an Archaerhodopsin (ArchT) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. In some embodiments, the ArchT protein comprises an amino acid sequence that is at least 75%, 85%, 90%, 91%, 92%, 93%, 94%, 95%, 96%, 97%, 98%, 99%, or 100% identical to the sequence shown in SEQ ID NO:23 (ArchT). The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a neuron. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a neuron in response to light.

In some cases, the ArchT polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRIT-SEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCY-ENEV (SEQ ID NO:58); and the like.

In certain embodiments, the ArchT protein comprises an amino acid sequence that is at least 75%, 85%, 90%, 91%, 92%, 93%, 94%, 95%, 96%, 97%, 98%, 99%, or 100% identical to the sequence shown in SEQ ID NO:24.

GtR3

In some embodiments, the light-activated polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The light can have a wavelength between about 450 and about 495 nm or can have a wavelength of about 490 nm. In some embodiment, a GtR3 protein comprises an amino acid sequence at least 85%, 90%, 91%, 92%, 93%, 94%, 95%, 96%, 97%, 98%, 99%, or 100% identical to the sequence shown in SEQ ID NO:25 (GtR3). The GtR3 protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of a neuronal cell in response to light.

In some cases, a GtR3 protein comprises a core amino acid sequence at least 75%, 85%, 90%, 91%, 92%, 93%, 94%, 95%, 96%, 97%, 98%, 99%, or 100% identical to the sequence shown in SEQ ID NO:25 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, GtR3 protein comprises an N-terminal signal peptide and a C-terminal ER export signal. In some embodiments, the GtR3 protein comprises an N-terminal signal peptide and a C-terminal trafficking signal. In some embodiments, the light-activated proton pump protein comprises an N-terminal signal peptide, a C-terminal ER Export signal, and a C-terminal trafficking signal. In some embodiments, the GtR3 protein comprises a C-terminal ER Export signal and a C-terminal trafficking signal. In some embodiments, the signal peptide comprises the amino acid sequence MDYGGALSAVGRELLFVTNPVVVNGS (SEQ ID NO:59). In some embodiments, the first 19 amino acids are replaced with MDYGGALSAVGRELLFVTNPVVVNGS (SEQ ID NO:59). In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The GtR3 protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, a GtR3 protein comprises an amino acid sequence that is at least 75%, 85%, 90%, 91%, 92%, 93%, 94%, 95%, 96%, 97%, 98%, 99%, or 100% identical to the sequence shown in SEQ ID NO:26.

Oxy

In some embodiments, a light-activated protein is an *Oxyrrhis marina* (Oxy) proton pump that can transport one or more protons across the plasma membrane of a cell when the cell is illuminated with light. The light can have a wavelength between about 500 and about 560 nm or can have a wavelength of about 530 nm. In some embodiments, the Oxy protein comprises an amino acid sequence that is at least 75%, 85%, 90%, 91%, 92%, 93%, 94%, 95%, 96%, 97%, 98%, 99%, or 100% identical to the sequence shown in SEQ ID NO:27. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a neuron. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a neuron in response to light.

In some embodiments, an Oxy protein comprises at least one (such as one, two, three, or more) amino acid sequence motifs that enhance transport to the plasma membranes of neurons selected from the group consisting of a signal peptide, an ER export signal, and a membrane trafficking signal. In some embodiments, the Oxy protein comprises an N-terminal signal peptide and a C-terminal ER export signal. In some embodiments, the Oxy protein includes an N-terminal signal peptide and a C-terminal trafficking signal. In some embodiments, the Oxy protein comprises an N-terminal signal peptide, a C-terminal ER export signal, and a C-terminal trafficking signal. In some embodiments, the Oxy protein comprises a C-terminal ER export signal and a C-terminal trafficking signal. In some embodiments, the C-terminal ER export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The Oxy protein may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some cases, the Oxy polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the Oxy protein comprises an amino acid sequence that is at least 75%, 85%, 90%, 91%, 92%, 93%, 94%, 95%, 96%, 97%, 98%, 99%, or 100% identical to the sequence shown in SEQ ID NO:28.

Mac

In some embodiments, the light-activated proton pump protein (referred to herein as "Mac protein") is responsive to light and is derived from *Leptosphaeria maculans*, wherein the Mac proton pump protein is capable of pumping protons across the membrane of a cell when the cell is illuminated with 520 nm to 560 nm light. The light can have a wavelength between about 520 nm to about 560 nm. In some cases, a Mac protein comprises an amino acid sequence at least 75%, 85%, 90%, 91%, 92%, 93%, 94%, 95%, 96%, 97%, 98%, 99%, or 100% identical to the sequence shown in SEQ ID NO:29 or SEQ ID NO:30 (Mac; Mac 3.0). The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of a neuronal cell in response to light.

In other aspects, a Mac protein comprises a core amino acid sequence at least 75%, 85%, 90%, 91%, 92%, 93%, 94%, 95%, 96%, 97%, 98%, 99%, or 100% identical to the sequence shown in SEQ ID NO:29 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the Mac protein comprises an N-terminal signal peptide and a C-terminal ER export signal. In some embodiments, the Mac protein comprises an N-terminal signal peptide and a C-terminal trafficking signal. In some embodiments, the Mac protein comprises an N-terminal signal peptide, a C-terminal ER Export signal, and a C-terminal trafficking signal. In some embodiments, the Mac protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The Mac protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some cases, the Mac polypeptide includes a membrane trafficking signal and/or an ER export signal. In some embodiments, the trafficking signal can be derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

Further disclosure related to light-activated proton pump proteins can be found in International Patent Application No. PCT/US2011/028893, the disclosure of which is hereby incorporated by reference in its entirety.

NpHR

In some cases, a suitable light-activated chloride pump protein is derived from *Natronomonas pharaonis*; such a protein is referred to herein as an "NpHR protein" or an "NpHR polypeptide." In some embodiments, the NpHR protein can be responsive to amber light as well as red light and can mediate a hyperpolarizing current in the neuron when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. In some embodiments, the NpHR protein comprises an amino acid sequence at least about 75%, 85%, 90%, 91%, 92%, 93%, 94%, 95%, 96%, 97%, 98%, 99%, or 100% identical to the sequence shown in SEQ ID NO:31. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. A NpHR protein containing substitutions, deletions, and/or insertions introduced into the native amino acid sequence suitably retains the ability to hyperpolarize the plasma membrane of a neuronal cell in response to light.

In some cases, an NpHR protein comprises a core amino acid sequence at least about 75%, 85%, 90%, 91%, 92%, 93%, 94%, 95%, 96%, 97%, 98%, 99%, or 100% identical to the sequence shown in SEQ ID NO:31; and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can be any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO:57), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:58).

Endoplasmic reticulum (ER) export sequences that are suitable for use include, e.g., VXXSL (where X is any amino acid; SEQ ID NO:52)) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, an NpHR protein comprises core amino acid sequence at least 75%, 85%, 90%, 91%, 92%, 93%, 94%, 95%, 96%, 97%, 98%, 99%, or 100% identical to the sequence shown in SEQ ID NO:31 and a trafficking signal (e.g., which can enhance transport of the NpHR protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker, which can be any of about 5, 10, 20, 30, 40, 50, 75, 100, 125, 150, 175, 200, 225, 250, 275, 300, 400, or 500 amino acids in length. The NpHR protein may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:56).

In some aspects, an NpHR protein comprises a core amino acid sequence at least 75%, 85%, 90%, 91%, 92%, 93%, 94%, 95%, 96%, 97%, 98%, 99%, or 100% identical to the sequence shown in SEQ ID NO:31; and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the NpHR protein includes an N-terminal signal peptide, a C-terminal ER Export signal, and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The NpHR protein can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide includes the amino acid sequence MTETLPPVTESAVALQAE (SEQ ID NO:62). In another embodiment, the NpHR protein includes an amino acid sequence at least 95% identical to SEQ ID NO:31. In another embodiment, the NpHR protein includes an amino acid sequence at least 95% identical to SEQ ID NO:31.

Moreover, in other aspects, an NpHR protein comprises a core amino acid sequence at least 75%, 85%, 90%, 91%, 92%, 93%, 94%, 95%, 96%, 97%, 98%, 99%, or 100% identical to the sequence shown in SEQ ID NO:31, wherein the N-terminal signal peptide of SEQ ID NO:31 is deleted or substituted. In some embodiments, other signal peptides (such as signal peptides from other opsins) can be used. The light-activated protein can further comprise an ER transport signal and/or a membrane trafficking signal described herein.

In some embodiments, the light-activated protein is an NpHR protein that comprises an amino acid sequence at least 75%, at least 85%, at least 90%, at least 95%, at least 96%, at least 97%, at least 98%, at least 99% or 100% identical to the sequence shown in SEQ ID NO:31. In some embodiments, the NpHR protein further comprises an endoplasmic reticulum (ER) export signal and/or a membrane trafficking signal. For example, the NpHR protein comprises an amino acid sequence at least 95% identical to the sequence shown in SEQ ID NO:31 and an endoplasmic reticulum (ER) export signal. In some embodiments, the amino acid sequence at least 95% identical to the sequence shown in SEQ ID NO:31 is linked to the ER export signal through a linker. In some embodiments, the ER export signal comprises the amino acid sequence FXYENE (SEQ ID NO:57), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:58). In some embodiments, the NpHR protein comprises an amino acid sequence at least 95% identical to the sequence shown in SEQ ID NO:31, an ER export signal, and a membrane trafficking signal. In other embodiments, the NpHR protein comprises, from the N-terminus to the C-terminus, the amino acid sequence at least 95% identical to the sequence shown in SEQ ID NO:31, the ER export signal, and the membrane trafficking signal. In other embodiments, the NpHR protein comprises, from the N-terminus to the C-terminus, the amino acid sequence at least 95% identical to the sequence shown in SEQ ID NO:31, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence KSRITSEGEYIPLDQIDINV (SEQ ID NO:56). In some embodiments, the membrane trafficking signal is linked to the amino acid sequence at least 95% identical to the sequence shown in SEQ ID NO:31 by a linker. In some embodiments, the membrane trafficking signal is linked to the ER export signal through a linker. The linker may be any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-activated protein further comprises an N-terminal signal peptide.

Further disclosure related to light-activated chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

Dunaliella Salina Light-Activated Polypeptide

In some embodiments, a suitable light-activated ion channel protein is, e.g., a DsChR protein derived from Dunaliella salina, wherein the ion channel protein is capable of mediating a hyperpolarizing current in the cell when the cell is illuminated with light. The light can have a wavelength between about 470 nm and about 510 nm or can have a wavelength of about 490 nm. In some embodiments, a DsChR protein comprises an amino acid sequence at least 75%, 85%, 90%, 91%, 92%, 93%, 94%, 95%, 96%, 97%, 98%, 99%, or 100% identical to the sequence shown in SEQ ID NO:34. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of a neuronal cell in response to light.

In some case, a DsChR protein comprises a core amino acid sequence at least 75%, 85%, 90%, 91%, 92%, 93%, 94%, 95%, 96%, 97%, 98%, 99%, or 100% identical to the sequence shown in SEQ ID NO:34; and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the DsChR protein comprises an N-terminal signal peptide and a C-terminal ER export signal. In some embodiments, the DsChR protein comprises an N-terminal signal peptide and a C-terminal trafficking signal. In some embodiments, the DsChR protein comprises an N-terminal signal peptide, a C-terminal ER Export signal, and a C-terminal trafficking signal. In some embodiments, the DsChR protein comprises a C-terminal ER Export signal and a C-terminal trafficking signal. In some embodiments, the C-terminal ER Export signal and the C-terminal trafficking signal are linked by a linker. The linker can be any of about 5, 10, 20, 30, 40, 50, 75, 100, 125, 150, 175, 200, 225, 250, 275, 300, 400, or 500 amino acids in length. The DsChR protein may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some cases, the DsChR polypeptide comprises a membrane trafficking signal and/or an ER export signal. In some embodiments, the trafficking signal is derived from the amino acid sequence of the human inward rectifier potassium channel Kir2.1. In other embodiments, the trafficking signal comprises the amino acid sequence KSRITSEGEYIPLDQIDINV (SEQ ID NO:56). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:56)). In some cases, the ER export signal is, e.g., VXXSL (where X is any amino acid; SEQ ID NO:52) (e.g., VKESL (SEQ ID NO:53), VLGSL (SEQ ID NO:54); etc.); NANSFCYENEVALTSK (SEQ ID NO:55); FXYENE (SEQ ID NO:57) (where X is any amino acid), e.g., FCYENEV (SEQ ID NO:58); and the like.

In certain embodiments, the DsChR protein comprises an amino acid sequence that is at least 75%, 85%, 90%, 91%, 92%, 93%, 94%, 95%, 96%, 97%, 98%, 99%, or 100% identical to the sequence shown in SEQ ID NO:35.

Anion Channel Polypeptides Based on C1C2

In some embodiments, a light-activated anion channel polypeptide is a C1C2 protein. In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36. In some embodiments, the amino acid sequence of the C1C2 protein is modified by introducing one or more of the following mutations into the amino acid sequence: T98S, E129S, E1405, E162S, V156K, H173R, T285N, V281K and/or N297Q. In some embodiments, a C1C2 protein comprises the amino acid sequence of the protein C1C2 with all 9 of the above-listed amino acid substitutions, such that the amino acid sequence of the C1C2 polypeptide is that set forth in SEQ ID NO:36.

In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and includes 1, 2, 3, 4, 5, 6, 7, 8, or 9 amino acid substitutions selected from T98S, E129S, E1405, E162S, V156K, H173R, T285N, V281K and/or N297Q, relative to the amino acid sequence of C1C2 (SEQ ID NO:36). In some embodiments, a C1C2 polypeptide includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and includes T98S, E129S, E1405, E162S, and T285N substitutions relative to the amino acid sequence of C1C2. In some embodiments, a C1C2 polypeptide includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and includes V156K, H173R, V281K, and N297Q substitutions relative to the amino acid sequence of C1C2.

In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and includes 1, 2, 3, 4, 5, 6, 7, 8, or 9 of: S98, S129, S140, S162, K156, R173, N285, K281, and Q297, where the amino acid numbering is as set forth in SEQ ID NO:36. In some embodiments, a C1C2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:36; and includes S98, S129, S140, S162, K156, R173, N285, K281, and Q297, where the amino acid numbering is as set forth in SEQ ID NO:36. In any one of these embodiments, a C1C2 polypeptide can comprise a membrane trafficking signal (e.g., KSRITSEGEYIPLDQIDINV (SEQ ID NO:56)). In any one of these embodiments, a C1C2 polypeptide can comprise an ER export signal (e.g., FCYENEV (SEQ ID NO:58)). In any one of these embodiments, a C1C2 polypeptide comprises both a membrane trafficking signal (e.g., KSRITSEGEYIPLDQIDINV (SEQ ID NO:56)) and an ER export signal (e.g., FCYENEV (SEQ ID NO:58)). Thus, in certain embodiments, the C1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO:36.

In some embodiments, a C1C2 polypeptide is based on the amino acid sequence of the protein C1C2 (SEQ ID NO:36), wherein the amino acid sequence has been modified by replacing the first 50 N-terminal amino acids of C1C2 with amino acids 1-11 from the protein ChR2 (MDYGGAL-SAVG) (SEQ ID NO:63). In some embodiments, a suitable light-activated anion channel polypeptide is referred to as "ibC1C2" and comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:40; and includes 1, 2, 3, 4, 5, 6, 7, 8, or 9 of: S59, S90, S101, S123, K117, R134, N246, K242, and Q258, where the amino acid numbering is as set forth in SEQ ID NO:40. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:40; and includes S59, S90, S101, S123, K117, R134, N246, K242, and Q258, where the amino acid numbering is as set forth in SEQ ID NO:40. In some embodiments, a suitable light-activated anion channel polypeptide comprises the amino acid sequence set forth in SEQ ID NO:40. In any one of these embodiments, a suitable anion channel polypeptide comprises a membrane trafficking signal (e.g., KSRITSEGEYIPLDQIDINV (SEQ ID NO:56)). In any one of these embodiments, a suitable anion channel polypeptide comprises an ER export signal (e.g., FCYENEV (SEQ ID NO:58)). In any one of these embodiments, a suitable anion channel polypeptide comprises both a membrane trafficking signal (e.g., KSRITSEGEYIPLDQIDINV (SEQ ID NO:56)) and an ER export signal (e.g., FCYENEV (SEQ ID NO:58)). Thus, in certain embodiments, the ibC1C2 protein comprises an amino acid sequence that is at least 75%, 85%, 90%, 91%, 92%, 93%, 94%, 95%, 96%, 97%, 98%, 99%, or 100% identical to the sequence shown in SEQ ID NO:40.

In some embodiments, a suitable light-activated anion channel polypeptide is based on the amino acid sequence of the protein C1C2 (SEQ ID NO:36), wherein the cysteine amino acid residue at position 167 has been replaced by a threonine residue. In some embodiments, a suitable light-activated anion channel polypeptide, e.g., SwiChR$_{cT}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:38; and comprises 1, 2, 3, 4, 5, 6, 7, 8, or 9 of: S98, S129, S140, S162, K156, R173, N285, K281, and Q297; and includes T167. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes S98, S129, S140, S162, K156, R173, N285, K281, and Q297; and includes T167, where the amino acid numbering is as set forth in SEQ ID NO:38. In some embodiments, a light-activated anion channel polypeptide comprises the amino acid sequence provided in SEQ ID NO:38. In some of these embodiments, the light-activated polypeptide exhibits prolonged stability of photocurrents. In some embodiments, the first 50 amino acids are replaced with MDYGGALSAVG (SEQ ID NO:63). In any one of these embodiments, a suitable anion channel polypeptide comprises a membrane trafficking signal (e.g., KSRITSEGEYIPLDQIDINV (SEQ ID NO:56)). In any one of these embodiments, a suitable anion channel polypeptide comprises an ER export signal (e.g., FCYENEV (SEQ ID NO:58)). In any one of these embodiments, a suitable anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a suitable light-activated anion channel polypeptide is based on the amino acid sequence of the protein C1C2, wherein the cysteine amino acid residue at position 167 has been replaced by an alanine residue. In some embodiments, a suitable light-activated anion channel polypeptide, SwiChR$_{cA}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes 1, 2, 3, 4, 5, 6, 7, 8, or 9 of: S98, S129, S140, S162, K156, R173, N285, K281, and Q297; and includes A167, where the amino acid numbering is as set forth in SEQ ID NO:38. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes S98, S129, S140, S162, K156, R173, N285, K281, and Q297; and includes A167, where the amino acid numbering is as set forth in SEQ ID NO:38. In some embodiments, the first 50 amino acids are replaced with MDYGGALSAVG (SEQ ID NO:63). In any one of these embodiments, a suitable anion channel polypeptide comprises a membrane trafficking signal (e.g., KSRITSEGEYIPLDQIDINV (SEQ ID NO:56)). In any one of these embodiments, a subject anion channel polypeptide includes an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a suitable light-activated anion channel polypeptide is based on the amino acid sequence of the protein C1C2, wherein the cysteine amino acid residue at position 167 has been replaced by a serine residue. In some embodiments, a suitable light-activated anion channel polypeptide, SwiChR$_{cS}$, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes 1, 2, 3, 4, 5, 6, 7, 8, or 9 of: S98, S129, S140, S162, K156, R173, N285, K281, and Q297; and includes S167, where the amino acid numbering is as set forth in SEQ ID NO:38. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes S98, S129, S140, S162, K156, R173, N285, K281, and Q297; and includes S167, where the amino acid numbering is as set forth in SEQ ID NO:38. In some embodiments, the first 50 amino acids are replaced with MDYGGALSAVG (SEQ ID NO:63). In any one of these embodiments, a suitable anion channel polypeptide comprises a membrane trafficking signal (e.g., KSRITSEGEYIPLDQIDINV (SEQ ID NO:56)). In any one of these embodiments, a subject anion channel polypeptide includes an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In certain embodiments, the SwiChR protein comprises an amino acid sequence that is at least 75%, 85%, 90%, 91%, 92%, 93%, 94%, 95%, 96%, 97%, 98%, 99%, or 100% identical to the sequence shown in SEQ ID NO:39.

In some embodiments, a suitable light-activated anion channel polypeptide, SwiChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes 1, 2, 3, 4, 5, 6, 7, 8, or 9 of: S98, S129, S140, S162, K156, R173, N285, K281, and Q297; includes N195, or A195; and includes A167, where the amino acid numbering is as set forth in SEQ ID NO:38. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:38; and includes S98, S129, S140, S162, K156, R173, N285, K281, and Q297; includes A167; and includes N195, or A195, where the amino acid numbering is as set forth in SEQ ID NO:38. In some embodiments, the first 50 amino acids are replaced with MDYGGALSAVG (SEQ ID NO:63). In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a suitable light-activated anion channel polypeptide is based on the amino acid sequence of the protein C1C2 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:36) is replaced by an alanine residue.

In some embodiments, a suitable hyperpolarizing light-activated polypeptide is based on the amino acid sequence of the protein C1C2 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1C2 amino acid sequence set forth in SEQ ID NO:36) is replaced by an asparagine residue.

In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:40; and includes 1, 2, 3, 4, 5, 6, 7, 8, or 9 of: S59, S90, S101, S123, K117, R134, N246, K242, and Q258; and includes A128, T128 or S128, where the amino acid numbering is as set forth in SEQ ID NO:40. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:40; and includes S59, S90, S101, S123, K117, R134, N246, K242, and Q258; and includes A128, T128 or S128, where the amino acid numbering is as set forth in SEQ ID NO:40. In any one of these embodiments, a subject anion channel polypeptide comprises a membrane trafficking signal (e.g., KSRITSEGEYIPLDQIDINV (SEQ ID NO:56)). In any one of these embodiments, a suitable anion channel polypeptide comprises an ER export signal (e.g., FCYENEV (SEQ ID NO:58)). In any one of these embodiments, a suitable anion channel polypeptide includes both a membrane trafficking signal (e.g., KSRITSEGEYIPLDQIDINV (SEQ ID NO:56)) and an ER export signal (e.g., FCYENEV (SEQ ID NO:58)).

Anion Channel Proteins Based on ChR2

In some embodiments, a suitable hyperpolarizing light-activated polypeptide is based on the amino acid sequence of the protein ChR2. The amino acid sequence of ChR2 is set forth in SEQ ID NO:42. In some embodiments, the amino acid sequence of the ChR2 protein has been modified by introducing one or more of the following mutations into the amino acid sequence: A59S, E905, E101S, E123S, Q117K, H134R, V242K, T246N and/or N258Q. In some embodiments, a suitable hyperpolarizing light-activated polypeptide comprises the amino acid sequence of the protein ChR2 with all 9 of the above-listed amino acid substitutions, such that the amino acid sequence of the polypeptide is provided in SEQ ID NO:42 (iChR2).

In some embodiments, a suitable light-activated anion channel polypeptide iChR2 comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:42; and includes 1, 2, 3, 4, 5, 6, 7, 8, or 9 amino acid substitutions selected from A59S, E905, E101S, E123S, Q117K, H134R, V242K, T246N and/or N258Q, relative to the amino acid sequence of ChR2 (SEQ ID NO:1).

In some embodiments, a suitable light-activated polypeptide ("iChR2") comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:42; and includes 1, 2, 3, 4, 5, 6, 7, 8, or 9 of: S59, S90, S101, S123, K117, R134, K242, N246 and Q258, where the amino acid numbering is as set forth in SEQ ID NO:42. In some embodiments, an iChR2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:42; and includes 1, 2, 3, 4, 5, 6, 7, 8, 9, 10 or 11 of: S59, S90, S101, S123, K117, R134, K242, Q258, and either N156 or A156, and either T128, A128, or S128, where the amino acid numbering is as set forth in SEQ ID NO:42. In some embodiments, an iChR2 polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:42; and includes S59, S90, S101, S123, K117, R134, K242, N246 and Q258, where the amino acid numbering is as set forth in SEQ ID NO:42. In any one of these embodiments, an iChR2 polypeptide can comprise a membrane trafficking signal (e.g., KSRITSEGEYIPLDQIDINV (SEQ ID NO:56)). In any one of these embodiments, an iChR2 polypeptide can comprise an ER export signal (e.g., FCYENEV (SEQ ID NO:58)). In any one of these embodiments, an iChR2 polypeptide can comprise both a membrane trafficking signal (e.g., KSRITSEGEYIPLDQIDINV (SEQ ID NO:56)) and an ER export signal (e.g., FCYENEV (SEQ ID NO:58)). Thus in certain embodiments, the iChR2 protein comprises an amino acid sequence that is at least 75%, 85%, 90%, 91%, 92%, 93%, 94%, 95%, 96%, 97%, 98%, 99%, or 100% identical to the sequence shown in SEQ ID NO:43.

Anion Channel Polypeptides Based on C1V1

In some embodiments, a suitable hyperpolarizing light-activated polypeptide is based on the amino acid sequence of the protein C1V1. The amino acid sequence of C1V1 is set forth in SEQ ID NO:44. In some embodiments, the amino acid sequence of the C1V1 protein has been modified by introducing one or more of the following mutations into the amino acid sequence: T98S, E129S, E140S, E162S, V156K, H173R, A285N, P281K and/or N297Q. In some embodiments, a hyperpolarizing light-activated polypeptide comprises the amino acid sequence of the protein C1V1 with all 9 of the above-listed amino acid substitutions, such that the amino acid sequence of the polypeptide is provided in SEQ ID NO:44.

In some embodiments, a suitable light-activated anion channel polypeptide, iC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:44; and includes 1, 2, 3, 4, 5, 6, 7, 8, or 9 amino acid substitutions selected from T98S, E129S, E140S, E162S, V156K, H173R, A285N, P281K and/or N297Q, relative to the amino acid sequence of C1V1 (SEQ ID NO:7).

In some embodiments, a suitable light-activated anion channel polypeptide, iC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:44; and includes 1, 2, 3, 4, 5, 6, 7, 8, or 9 of: S98, S129, S140, S162, K156, R173, N285, K281, and Q297, where the amino acid numbering is as set forth in SEQ ID NO:44. In some embodiments, a suitable light-activated anion channel polypeptide (referred to as "iC1V1"), comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:44; and includes 1, 2, 3, 4, 5, 6, 7, 8, or 9 of: S98, S129, S140, S162, K156, R173, N285, K281, and Q297, and includes N195, where the amino acid numbering is as set forth in SEQ ID NO:44. In some embodiments, a suitable light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:44; and includes S98, S129, S140, S162, K156, R173, N285, K281, and Q297, where the amino acid numbering is as set forth in SEQ ID NO:44. In any one of these embodiments, a suitable anion channel polypeptide includes a membrane trafficking signal (e.g., KSRITSEGEYIPLDQIDINV (SEQ ID NO:56)). In any one of these embodiments, a subject anion channel polypeptide includes an ER export signal (e.g., FCYENEV (SEQ ID NO:58)). In any one of these embodiments, a suitable anion channel polypeptide comprises both a membrane trafficking signal (e.g., KSRITSEGEYIPLDQIDINV (SEQ ID NO:56)) and an ER export signal (e.g., FCYENEV (SEQ ID NO:58)). Thus in certain embodiments, the iC1V1protein can have an amino acid sequence that is at least 75%, 85%, 90%, 91%, 92%, 93%, 94%, 95%, 96%, 97%, 98%, 99%, or 100% identical to the sequence shown in SEQ ID NO:45.

In some embodiments, a suitable hyperpolarizing light-activated polypeptide is based on the amino acid sequence of the protein C1V1 (SEQ ID NO:7), wherein the amino acid sequence has been modified by replacing the first 50 N-terminal amino acids of C1V1 with amino acids 1-11 from the protein ChR2 (MDYGGALSAVG) (SEQ ID NO:63). In some embodiments, a suitable hyperpolarizing light-activated polypeptide, ibC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes 1, 2, 3, 4, 5, 6, 7, 8, or 9 of: S59, S90, S101, S123, K117, R134, N246, K242, and Q258, where the amino acid numbering is as set forth in SEQ ID NO:46. In some embodiments, a suitable hyperpolarizing light-activated polypeptide (referred to as "ibC1V1"), comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes 1, 2, 3, 4, 5, 6, 7, 8, or 9 of: S59, S90, S101, S123, K117, R134, N246, K242, and Q258, and includes N156, where the amino acid numbering is as set forth in SEQ ID NO:46. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes S59, S90, S101, S123, K117, R134, N246, K242, and Q258, where the amino acid numbering is as set forth in SEQ ID NO:46. In some embodiments, a suitable light-activated anion channel polypeptide comprises the amino acid sequence set forth in SEQ ID NO:46. In any one of these embodiments, a suitable anion channel polypeptide comprises a membrane trafficking signal (e.g., KSRITSEGEYIPLDQIDINV (SEQ ID NO:56)). In any one of these embodiments, a suitable anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)). Thus in certain embodiments, an ibC1V1 protein comprises an amino acid sequence that is at least 75%, 85%, 90%, 91%, 92%, 93%, 94%, 95%, 96%, 97%, 98%, 99%, or 100% identical to the sequence shown in SEQ ID NO:47.

In some embodiments, a suitable hyperpolarizing light-activated polypeptide is based on the amino acid sequence of the protein C1V1 (SEQ ID NO:7), wherein the cysteine amino acid residue at position 167 has been replaced by a threonine residue. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:7; and includes 1, 2, 3, 4, 5, 6, 7, 8, or 9 of: S98, S129, S140, S162, K156, R173, N285, K281, and Q297; and includes T167. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:44; and includes S98, S129, S140, S162, K156, R173, N285, K281, and Q297; and includes T167, S167 or A167, where the amino acid numbering is as set forth in SEQ ID NO:44. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:46; and includes S98, S129, S140, S162, K156, R173, N285, K281, and Q297; includes T167, S167 or A167; and includes A195 or N195, where the amino acid numbering is as set forth in SEQ ID NO:46. In some embodiments, the first 50 amino acids are replaced with MDYGGALSAVG (SEQ ID NO:63). In any one of these embodiments, a suitable hyperpolarizing light-activated polypeptide comprises a membrane trafficking signal (e.g., KSRITSEGEYIPLDQIDINV (SEQ ID NO:56)). In any one of these embodiments, a suitable hyperpolarizing light-activated polypeptidecomprises an ER export signal (e.g., FCYENEV (SEQ ID NO:58)). In any one of these embodiments, a suitable hyperpolarizing light-activated polypeptide includes both a membrane trafficking signal (e.g., KSRITSEGEYIPLDQIDINV (SEQ ID NO:56)) and an ER export signal (e.g., FCYENEV (SEQ ID NO:58)).

In some embodiments, a suitable hyperpolarizing light-activated polypeptide is based on the amino acid sequence of the protein C1V1 with one or more of the modifications described above, wherein the aspartate amino acid residue at original position 195 has been replaced by an alanine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:7) is replaced by an alanine residue.

In some embodiments, a suitable hyperpolarizing light-activated polypeptide is based on the amino acid sequence of the protein C1V1 with one or more of the modifications described above, wherein the aspartate amino acid residue at original position 195 has been replaced by an asparagine residue. In certain embodiments wherein the first 50 N-terminal amino acids of the protein are replaced by amino acids 1-11 from the protein ChR2, the aspartate amino acid residue at position 156 (which corresponds to original position 195 of the C1V1 amino acid sequence set forth in SEQ ID NO:7) is replaced by an asparagine residue.

In some embodiments, a suitable hyperpolarizing light-activated polypeptide, ibC1V1, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes 1, 2, 3, 4, 5, 6, 7, 8, or 9 of: S59, S90, S101, S123, K117, R134, N246, K242, and Q258; and includes T128, A128, or S128, where the amino acid numbering is as set forth in SEQ ID NO:46. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes S59, S90, S101, S123, K117, R134, N246, K242, and Q258; and includes T128, A128, or S128, where the amino acid numbering is as set forth in SEQ ID NO:46. In any one of these embodiments, a suitable anion channel polypeptide comprises a membrane trafficking signal (e.g., KSRITSEGEYIPLDQIDINV (SEQ ID NO:56)). In any one of these embodiments, a suitable anion channel polypeptide comprises an ER export signal (e.g., FCYENEV (SEQ ID NO:58)). In any one of these embodiments, a suitable anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes 1, 2, 3, 4, 5, 6, 7, 8, or 9 of: S59, S90, S101, S123, K117, R134, N246, K242, and Q258; and includes T128, A128, or S128; and includes A156 or N156, where the amino acid numbering is as set forth in SEQ ID NO:46. In some embodiments, a suitable hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:46; and includes S59, S90, S101, S123, K117, R134, N246, K242, and Q258; and includes T128, A128, or S128; and includes A156 or N156, where the amino acid numbering is as set forth in SEQ ID NO:46. In any one of these embodiments, a suitable hyperpolarizing light-activated polypeptide comprises a membrane trafficking signal (e.g., KSRITSEGEYIPLDQIDINV (SEQ ID NO:56)). In any one of these embodiments, a suitable hyperpolarizing light-activated polypeptide comprises an ER export signal (e.g., FCYENEV (SEQ ID NO:58)). In any one of these embodiments, a subject anion channel polypeptide includes both a membrane trafficking signal (e.g., KSRITSEGEYIPLDQIDINV (SEQ ID NO:56)) and an ER export signal (e.g., FCYENEV (SEQ ID NO:58)).

Anion Channel Polypeptides Based on ReaChR

In some embodiments, a subject hyperpolarizing light-activated polypeptide is based on the amino acid sequence of the protein ReaChR. The amino acid sequence of ReaChR is set forth in SEQ ID NO:11. In some embodiments, the amino acid sequence of the ReaChR protein has been modified by introducing one or more of the following mutations into the amino acid sequence: T99S, E130S, E141S, E163S, V157K, H174R, A286N, P282K and/or N298Q. In some embodiments, a subject hyperpolarizing light-activated polypeptide comprises the amino acid sequence of the protein ReaChR with all 9 of the above-listed amino acid substitutions, such that the amino acid sequence of the polypeptide is provided in SEQ ID NO:48.

In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and includes 1, 2, 3, 4, 5, 6, 7, 8, or 9 amino acid substitutions selected from T99S, E130S, E141S, E163S, V157K, H174R, A286N, P282K and/or N298Q, relative to the amino acid sequence of ReaChR (SEQ ID NO:11).

In some embodiments, a subject light-activated anion channel polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and includes 1, 2, 3, 4, 5, 6, 7, 8, or 9 of: S99, S130, S141, S163, K157, R174, N286, K281, and Q298, where the amino acid numbering is as set forth in SEQ ID NO:48. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and includes S99, S130, S141, S163, K157, R174, N286, K281, and Q298, where the amino acid numbering is as set forth in SEQ ID NO:48. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide includes both a membrane trafficking signal (e.g., KSRITSEGEYIPLDQIDINV (SEQ ID NO:56)) and an ER export signal (e.g., FCYENEV (SEQ ID NO:58)). Thus in certain embodiments, the iReaChR protein comprises an amino acid sequence that is at least 75%, 85%, 90%, 91%, 92%, 93%, 94%, 95%, 96%, 97%, 98%, 99%, or 100% identical to the sequence shown in SEQ ID NO:49.

In some embodiments, a subject light-activated anion channel polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and includes 1, 2, 3, 4, 5, 6, 7, 8, or 9 of: S99, S130, S141, S163, K157, R174, N286, K281, and Q298, and includes N196, where the amino acid numbering is as set forth in SEQ ID NO:48. In some embodiments, a subject light-activated anion channel polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:48; and includes S99, S130, S141, S163, K157, R174, N286, K281, and Q298, and includes N196, where the amino acid numbering is as set forth in SEQ ID NO:48. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a subject hyperpolarizing light-activated polypeptide is based on the amino acid sequence of the protein ReaChR (SEQ ID NO:11), wherein the amino acid sequence has been modified by replacing the first 51 N-terminal amino acids of ReaChR with amino acids 1-11 from the protein ChR2 (MDYGGALSAVG) (SEQ ID NO:63). In some embodiments, a subject hyperpolarizing light-activated polypeptide, ibReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes 1, 2, 3, 4, 5, 6, 7, 8, or 9 of: S59, S90, S101, S123, K117, R134, N246, K242, and Q258, where the amino acid numbering is as set forth in SEQ ID NO:50. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes S59, S90, S101, S123, K117, R134, N246, K242, and Q258, where the amino acid numbering is as set forth in SEQ ID NO:50. In some embodiments, a subject light-activated anion channel polypeptide comprises the amino acid sequence set forth in SEQ ID NO:50. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)). Thus in certain embodiments, the ibReaChR protein can have an amino acid sequence that is at least 75%, 85%, 90%, 91%, 92%, 93%, 94%, 95%, 96%, 97%, 98%, 99%, or 100% identical to the sequence shown in SEQ ID NO:51.

In some embodiments, a subject hyperpolarizing light-activated polypeptide is based on the amino acid sequence of the protein ReaChR (SEQ ID NO:11), wherein the amino acid sequence has been modified by replacing the first 51 N-terminal amino acids of ReaChR with amino acids 1-11 from the protein ChR2 (MDYGGALSAVG) (SEQ ID NO:63). In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:11; and includes 1, 2, 3, 4, 5, 6, 7, 8, or 9 of: S59, S90, S101, S123, K117, R134, N246, K242, and Q258, and includes N156, where the amino acid numbering is as set forth in SEQ ID NO:11. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:11; and includes S59, S90, S101, S123, K117, R134, N246, K242, and Q258, and includes N156, where the amino acid numbering is as set forth in SEQ ID NO:11. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a subject hyperpolarizing light-activated polypeptide is based on the amino acid sequence of the protein ReaChR (SEQ ID NO:11), wherein the cysteine amino acid residue at position 168 has been replaced by a threonine residue. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:11; and includes 1, 2, 3, 4, 5, 6, 7, 8, or 9 of: S99, S130, S141, S163, K157, R174, N286, K281, and Q298; and includes T168, S168 or A168. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:11; and includes S99, S130, S141, S163, K157, R174, N286, K281, and Q298; and includes T168, S168 or A168, where the amino acid numbering is as set forth in SEQ ID NO:11. In some embodiments, the first 51 amino acids are replaced with MDYGGALSAVG (SEQ ID NO:63). In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a subject hyperpolarizing light-activated polypeptide, iReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:48; and includes 1, 2, 3, 4, 5, 6, 7, 8, or 9 of: S99, S130, S141, S163, K157, R174, N286, K281, and Q298; includes A196 or N196; and includes T168, S168, or A168, where the amino acid numbering is as set forth in SEQ ID NO:48. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth SEQ ID NO:48; and includes S99, S130, S141, S163, K157, R174, N286, K281, and Q298; includes A196 or N196; and includes T168, S168, or A168, where the amino acid numbering is as set forth in SEQ ID NO:48. In some embodiments, the first 51 amino acids are replaced with MDYGGALSAVG (SEQ ID NO:63). In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide includes both a membrane trafficking signal (e.g., KSRITSEGEYIPLDQIDINV (SEQ ID NO:56)) and an ER export signal (e.g., FCYENEV (SEQ ID NO:58)).

In some embodiments, a subject hyperpolarizing light-activated polypeptide is based on the amino acid sequence of the protein ReaChR with one or more of the modifications described above, wherein the aspartate amino acid residue at original position 196 has been replaced by an alanine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:11) is replaced by an alanine residue.

In some embodiments, a subject hyperpolarizing light-activated polypeptide is based on the amino acid sequence of the protein ReaChR with one or more of the modifications described above, wherein the aspartate amino acid residue at original position 196 has been replaced by an asparagine residue. In certain embodiments wherein the first 51 N-terminal amino acids of the protein are replaced by amino acids 1-11 from the protein ChR2, the aspartate amino acid residue at position 156 (which corresponds to original position 196 of the ReaChR amino acid sequence set forth in SEQ ID NO:11) is replaced by an asparagine residue.

In some embodiments, a subject hyperpolarizing light-activated polypeptide, ibReaChR, comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes 1, 2, 3, 4, 5, 6, 7, 8, or 9 of: S59, S90, S101, S123, K117, R134, N246, K242, and Q258; and includes T128, S128 or A128, where the amino acid numbering is as set forth in SEQ ID NO:50. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes S59, S90, S101, S123, K117, R134, N246, K242, and Q258; and includes T128, where the amino acid numbering is as set forth in SEQ ID NO:50. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide comprises an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

In some embodiments, a subject hyperpolarizing light-activated polypeptide, ibReaChR, includes an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes 1, 2, 3, 4, 5, 6, 7, 8, or 9 of: S59, S90, S101, S123, K117, R134, N246, K242, and Q258; includes T128, S128 or A128; and includes A156 or N156, where the amino acid numbering is as set forth in SEQ ID NO:50. In some embodiments, a subject hyperpolarizing light-activated polypeptide comprises an amino acid sequence having at least 58%, at least 60%, at least 65%, at least 70%, at least 75%, at least 80%, at least 85%, at least 90%, at least 95%, at least 98%, at least 99%, or 100%, amino acid sequence identity to the amino acid sequence set forth in SEQ ID NO:50; and includes S59, S90, S101, S123, K117, R134, N246, K242, and Q258; includes T128, S128 or A128; and includes A156 or N156, where the amino acid numbering is as set forth in SEQ ID NO:50. In any one of these embodiments, a subject anion channel polypeptide comprises a membrane trafficking signal (e.g., KSRITSEGEYIPLDQIDINV (SEQ ID NO:56)). In any one of these embodiments, a subject anion channel polypeptide includes an ER export signal (e.g., FCYENEV (SEQ ID NO:58)). In any one of these embodiments, a subject anion channel polypeptide comprises both a membrane trafficking signal (e.g., KSRITSEGEYIPLDQIDINV (SEQ ID NO:56)) and an ER export signal (e.g., FCYENEV (SEQ ID NO:58)).

Utility

The methods of the present disclosure find a variety of uses. As described above, the methods of the present disclosure find use in dissecting and analyzing functional brain circuits. In some cases, the present method may provide a way to identify new roles for anatomically and/or functionally defined neurons in functional circuits. In some cases, the anatomical or structural connections between regions of the brain may not be sufficient to provide insight into the functional role of the connections, and a method of the present disclosure may reveal the functional connection.

In some cases, the present methods may provide a way to establish a causative link at a cellular level for functional connections between regions of the brain for which only correlative data is available. Thus, in some cases, the present methods can demonstrate the presence or absence of a causative relationship underlying a correlative observation in a brain circuit.

In certain embodiments, the present methods provide for selectively activating a specific population of neurons, via a combination of selective expression of light-activated polypeptides and selective illumination of brain regions, at different temporal frequencies, wherein the number of neurons activated at each frequency remains substantially the same. Thus, an effect of increased frequency of light pulses activating a first region on the response at a functionally connected second region of the brain may be attributed mainly to the change in frequency, and not on other factors, e.g., recruitment of more neurons in a frequency-dependent manner.

The present methods also find use in probing the effect of deep brain stimulation (DBS) of brain regions, e.g., the central thalamus, insula, cingulate, subthalamic nucleus (STN), globus pallidus interna (GPI), zona incerta (ZI), etc., that may find use in the treatment of various neurological disorders, such as pain, depression, addiction, Alzheimer's disease, attention deficit disorder, autism, anorgasmia, cerebral palsy, bipolar depression, unipolar depression, epilepsy, generalized anxiety disorder, acute head trauma, hedonism, obesity, obsessive-compulsive disorder (OCD), acute pain, chronic pain, Parkinson's disease, persistent vegetative state, phobia, post-traumatic stress disorder, rehabilitation/regenesis for post-stroke, post-head trauma, social anxiety disorder, Tourette's Syndrome, hemorrhagic stroke, and ischemic stroke. The present methods, in some cases, may provide a way to probe the effect of a single parameter of stimulation, such as light pulse frequency or pulse width, of a defined population of neurons, on global brain dynamics, as well as cellular level functional circuits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Materials and Methods

Animals. Female Sprague-Dawley rats (>11 weeks old, 250-350 g) were used as subjects for all thalamic injections. Animals were individually housed under a 12 hour light-dark cycle and provided with food and water ad libitum. Animal husbandry and experimental manipulation were in strict accordance with National Institute of Health, University of California, Los Angeles (UCLA) Institutional Animal Care and Use Committee (IACUC), and Stanford University IACUC guidelines.

Figure 1B:
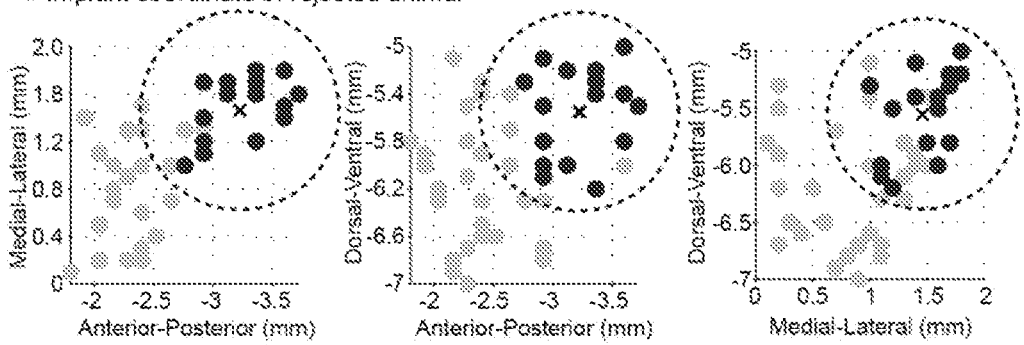
Figure 1B:
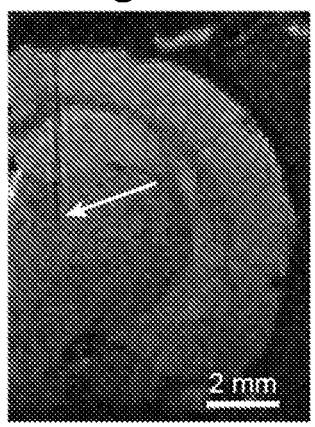
Figure 1B:
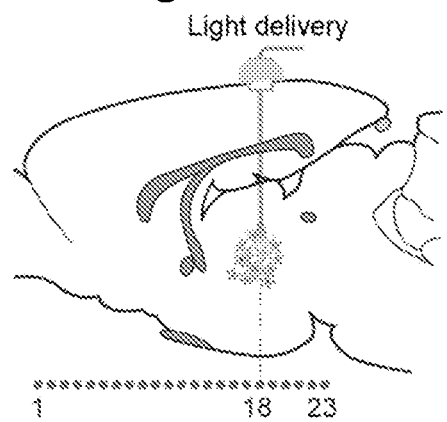

Viral injections and fiber placement. pAAV5-CaMKIIa-hChR2(H134R)-EYFP-WPRE plasmid was obtained from the Deisseroth lab at Stanford University. Concentrated virus was produced at the vector core of the University of North Carolina at Chapel Hill. Rats were anesthetized with isoflurane (induction 5%, maintenance 2-3%; Sigma-Aldrich, St. Louis, Mo., USA) and secured in a stereotactic frame. Standard procedures for sterile surgery were followed. Buprenorphine was administered to minimize pain. Artificial tears were applied to the eyes. The head was shaved, and 70% ethanol and betadine were applied to the bare scalp following a midline incision. A small craniotomy was performed with a dental drill above the targeted coordinate. Two microliters of virus were injected through a 34 gauge needle (World Precision Instruments Inc., Sarasota, Fla.) at 150 nl/min with a micro-syringe pump controller at the desired coordinates in central thalamus or other subcortical targets for control experiments: I) CL and PC nuclei of central thalamus (−3.2 mm AP, +1.5 mm ML, −5.6 mm DV; n=47 animals for imaging); II) ventral posteromedial nucleus (−2.5 mm AP, +2.6 mm ML, −6.0 mm DV); III) anterior thalamic nuclei (−3.1 mm AP, +1.8 mm ML, −5.3 mm DV); IV) posterior thalamic nuclei (−4.6 mm AP, +1.8 mm ML, −5.0 mm DV); V) intermediate hippocampus (−5.8 mm AP, +5.2 mm ML, −3.4 mm DV, n=8 animals). All injections were made in the right hemisphere. The syringe needle was left in place for an additional 10 minutes before being slowly withdrawn. Custom-designed guide cannulas (Plastics One) or fiber-optic cannulas (Doric Lenses Inc.) were mounted on the skull and secured using metabond (Parkell). Incisions were sutured, and animals were kept on a heating pad until recovery from anesthesia. Buprenorphine was injected subcutaneously twice daily for 48 hours postoperatively to minimize discomfort. The original cohort of 47 central thalamus animals was further refined to a group of 18 after screening for implant locations less than 0.85 mm away from the target coordinate (estimated with T2 magnetic resonance imaging (MRI) scans; FIG. 1B). Two additional animals were excluded due to lack of thalamic activation, leaving 16 animals for analysis.

In a second cohort of rats, concentrated AAVS-hSyn-eNpHR3.0-mCherry virus produced at the University of North Carolina at Chapel Hill vector core was injected into the right zona incerta (−3.96 mm AP, +2.8 mm ML, +7.4 mm DV, n=4 animals) after completion of the ChR2 injection into the central thalamus as described above. Both injections were performed during the same surgery. 0.5 microliters of eNpHR virus were injected through a 34 gauge needle at 100 nl/min. Following the injection, the syringe needle was left in place for approximately 10 minutes before being slowly withdrawn. Recovery details were the same as described above.

Optogenetic functional MRI (ofMRI) data acquisition. Functional MRI (fMRI) scanning was performed using a 7T Bruker Biospec small animal MRI system at UCLA. Animals were initially anesthetized with 5% isoflurane and intubated before placement onto custom-made MRI-compatible cradles with ear and tooth securement. A 39 mm outer diameter, 25 mm inner diameter custom-designed transmit/receive single-loop surface coil was centered over the region of interest on the skull to maximize signal-to-noise ratio. An optical fiber of 62.5 μm core diameter was connected to a 473 nm laser source (Laserglow Technologies, Toronto, Canada) and coupled with the implanted fiber-optic cannula. A single ofMRI scan consisted of a block design with six 20 s pulse trains of light (10, 40, or 100 Hz in randomized order) delivered once per minute over 6 minutes. Five to six consecutive scans were collected during each session. For all experiments, the optical fiber output power was calibrated to 2.5 mW. A duty cycle of 30% was used across frequencies to maintain the total amount of light delivery, resulting in unique pulse widths of 30, 7.5, and 3 ms for 10, 40, and 100 Hz, respectively. In a series of control experiments using a second cohort of animals with validated probe locations (n=3), the duty cycle was varied while the pulse width was held constant at 3 ms (FIG. 10).

During fMRI scanning, animals were placed into the iso-center of the magnet while artificially ventilated (45~60 strokes/min) under light anesthesia using a ventilator and calibrated vaporizer with a mixture of $O_2$ (35%), $N_2O$ (63.5%), and isoflurane (1.3-1.5%). To ensure stable (blood oxygenation level dependent) BOLD signals, expiratory $CO_2$ was kept at 3-4% and body temperature was maintained at 36.5-37.5° C. using heated airflow. T2-weighted high-resolution anatomical images were acquired with a fast spin echo sequence prior to fMRI scanning to check for brain damage and validate the optical fiber's location (137 μm resolution in-plane resolution with 35×35 mm² field of view (FOV), 0.5 mm slice thickness, 32 coronal slices). Gradient recalled echo (GRE) BOLD methods were used to acquire fMRI images during photostimulation. The fMRI image acquisition was designed to have 35×35 mm² in-plane field of view (FOV) and 0.5×0.5×0.5 mm³ spatial resolution with a sliding window reconstruction to update the image every repetition time (TR). The two-dimensional, multi-slice gradient-echo sequence used a four-interleave spiral readout (96, 97), 30° flip angle, 750 ms TR, and 12 ms echo time, resulting in 23 coronal slices (128×128 matrix size). The spiral k-space samples were reconstructed through a 2-dimensional gridding reconstruction method. Finally, real-time motion correction was performed using a previously described graphical processing unit (GPU)-based system. Scans with significant motion, identified by careful visual inspection for spiral artifacts and activations at the boundary of the brain, which indicates large motion, were excluded from analysis. This condition for exclusion was established prior to data collection.

fMRI data analysis. All fMRI data processing was performed using the Matlab® software environment (Math-Works, Inc., Natick, Mass.) and mrVista (Stanford Vision and Imaging Science and Technology Laboratory, Stanford, Calif.; web(dot)stanford(dot)edu/group/vista/cgi-bin/wiki/index(dot)php/MrVista). Motion-corrected images belonging to consecutive scans of the same stimulation paradigm and scanning session were first averaged together. The average four-dimensional (4D) images were then aligned to a common coordinate frame, using a six degree-of-freedom rigid body transformation. If multiple scanning sessions were performed on the same animal at the same frequency (typically 1, at most 4), the resulting images from each session were first averaged together before any inter-subject analysis to achieve maximum signal-to-noise ratio (SNR) while weighting the images from all animal subjects equally.

Time series were calculated for each voxel in these individual-animal images as the percent modulation of the BOLD signal relative to a 30 s baseline period collected prior to stimulation. Boxcar detrending with a window size of 1 minute was also performed to correct for possible scanner drift. Next, a coherence value was calculated for each voxel's time series as the magnitude of its Fourier transform at the frequency of repeated stimulation blocks (i.e. 1/60 Hz) divided by the sum-of-squares of all frequency components. Voxels with a coherence value greater than 0.35 were considered to be significantly synchronized to stimulation. Assuming Gaussian noise and ~470 degrees of freedom (computed using the statistical parametric mapping (SPM) software environment), the Bonferroni-corrected P value for this threshold can be estimated to be less than $10^{-9}$. Activation volume (FIG. 2) was defined as the number of significant voxels that exhibited a positive response within a predefined region of interest, multiplied by the volume per voxel. Positive responses were identified as having a phase in the interval $[0, \pi/2] \cup [3\pi/2, 2\pi]$. Phase represents the temporal shift of the response when it is modeled as a sinusoid, and was calculated as the argument of each voxel's Fourier transform at the frequency of repeated stimulation blocks (i.e. 1/60 Hz).

Hemodynamic response functions (HRFs) were calculated as the average 60 s response of a voxel's six-cycle, 6-minute time series. Time series and HRFs displayed for figures were generated by averaging the mean time series or mean HRF of voxels with a coherence value greater than 0.35 in the corresponding ROI across animals. In some cases, the first data point's value was subtracted from each voxel's HRF to define its relative percent modulation from the onset of stimulation.

To generate average activation maps (FIG. 2), the 4D fMRI images from experiments at the same stimulation location and frequency were normalized and averaged together across animals. The averaged images were then processed according to the above Fourier domain analyses. Coherence values were overlaid onto all voxels having a coherence above the 0.35 threshold. Warm and cool colormaps generated using MatlabCY s 'hot' and 'winter' functions were used for positive and negative responses, respectively, to illustrate the localization of negative BOLD to the somatosensory cortex. These activation maps were overlaid onto corresponding T2-weighted anatomical images with a digital standard rat brain atlas. The same atlas was used to segment ROIs. An identical analysis pipeline was used for activation maps in FIG. 10 with a representative animal.

Electroencephalogram (EEG) electrode implantation. EEG electrodes were implanted upon completion of ofMRI experiments in a subset of animals. Surgical preparation and recovery details were the same as those used for virus injection. Stainless steel screws (0-80, 1.5 mm diameter, Plastics One) attached to 2 cm of insulated wire (30 gauge, R30Y0100, Wire Wrapping Wire, O.K. Industries) were used as EEG electrodes and secured on the skull using dental cement. The recording electrode was placed approximately 2 mm anterior of bregma and 2 mm to the right of midline. The reference electrode was located approximately 5 mm anterior of bregma and 3 mm to the left of midline.

Video-EEG acquisition and analysis. Prior to video-EEG recording, animals were anesthetized under 5% isoflurane for approximately 5 min for optical fiber coupling and EEG wire connection. Animals were then transferred to a light- and sound-controlled experimental chamber where they were allowed to move freely. Behavioral experiments began after animals recovered from anesthesia and subsequently fell asleep for 15 min (as indicated by lack of motion and real-time EEG output readings). For each experiment, the animal was video-recorded during 5 min of sleep, followed by 20 s of optical stimulation (10, 40, or 100 Hz, 473 nm laser, 2.5 mW laser power, 30% duty cycle), and then an additional 5 min post-stimulation period. EEG data was acquired throughout the experiment at 1 kHz with an MP150 data acquisition unit and EEG100C amplifier (Biopac Systems Inc., Santa Barbara, Calif.), using EL254S Ag—AgCl electrodes and Gel102 conductive EEG paste. A digital camera was used to video-record the experiment. All behavioral experiments were performed during the animals' light cycle.

EEG recordings were classified using the Biopac Acqknowledge® software by an experienced electroencephalographer blind to treatment into a single best category: normal, low-voltage fast, spikes, spike-waves, or evolving electrographic seizure. Video clips paired to each EEG recording were classified into one of the following categories to further assess the animal's brain state: sleep (i.e. no change), awakening (animal is alert and exploring), absence seizure (animal is immobile and appears frozen for the duration of stimulation, but returns to a sleeping state once stimulation ends), or convulsive seizure. All observed behavioral responses could be classified into one of these categories. Band power in FIG. 13 was quantified using Matlab®'s 'bandpower' function and normalized by the signal's total power from 0 Hz to one half the sampling rate (500 Hz).

In vivo electrophysiology. Upon completion of ofMRI and EEG behavioral experiments, in vivo electrophysiology experiments were performed in a subset of animals. Animals were anesthetized with 5% isoflurane for induction and maintained at 2-3% until any craniotomies were complete. Isoflurane was kept at 0.8-1.2% during the recording session, and artificial tears were applied to the eyes. Recordings in FIGS. 4 and 5 were performed under ventilation conditions identical to fMRI experiments. After securing the animal within a stereotactic frame, small craniotomies were performed using a dental drill above the region of interest. For stimulation, the cannula implanted at central thalamus was connected to a 473 nm laser source (Laserglow Technologies) with an output power level of 2.5 mW via an optical fiber. The cannula implanted at zona incerta was connected to a 593 nm laser source (Laserglow Technologies) calibrated to 2.5-3.0 mW. An acute 16-channel microelectrode array was targeted to the recording site using stereotactic instruments (NeuroNexus Technologies; A1×16 standard model linear electrode array for local and cortical recordings; V1-16-Poly2 polytrode array for ZI recordings; 0.35±0.5 MOhm impedance). A stainless steel reference screw was placed above the cerebellum. Continuous field potential and single unit spiking events were recorded using the Plexon omniplex system with plexcontrol software (Plexon Inc., Tex., USA). When only ChR2 was activated, recordings were performed for 20 seconds without stimulation, followed by repeated stimulation cycles (20 s on, 40 s off) at 10, 40, or 100 Hz with 30% duty cycle. When ChR2 and eNpHR were activated together, the same stimulation paradigm was followed, except that a 30 s period of continuous 593 nm light delivery began 5 s before the onset of ChR2 excitation. When only eNpHR was activated (FIG. 5D), a 20 or 30 s period of continuous 593 nm light delivery was used, with 40 or 30 s periods of no light delivery between repeated cycles, respectively. For single unit responses, the Plexon multichannel acquisition processor was used to amplify and band-pass filter the neuronal signals (150 Hz-8 kHz). Signals were digitized at 40 kHz and processed to extract action potentials in real-time. To separate the field potential, a low-pass filter (200 Hz cutoff frequency, 4-pole Bessel filter) was used and signals were downsampled to 1 kHz. Simultaneous EEG data was collected at 1 kHz during zona incerta recordings in FIG. 4 using the MP150 data acquisition unit and EEG100C amplifier (Biopac).

Zona incerta electrophysiology analysis. For the analysis in FIG. 4, field potential recordings were high pass filtered with a cutoff frequency of 2 Hz to eliminate respiratory artifacts. Spindle-like oscillations (SLOs) occurring during the stimulus were then quantified on a per trial basis using a post-hoc custom algorithm. Briefly, an SLO was identified when the recording's magnitude reached at least 6 standard deviations above its mean absolute value. If the recording did not exceed this value for the preceding 500 ms, and was above this value for at least 2% of samples over the next 500 ms, an SLO was counted. This method of quantification accurately captured the large-amplitude oscillations that could be visually discerned (see FIG. 4D).

Fluorescence imaging and immunohistochemistry. Upon completion of in vivo ofMRI, behavioral, and electrophysiology experiments, rats were deeply anesthetized with isoflurane in a knockdown box and transcardially perfused with 0.1M phosphate buffered saline (PBS) and ice-cold 4% paraformaldehyde (PFA) in PBS. Brains were extracted and fixed in 4% PFA overnight at 4° C. The brains were equilibrated in 10%, 20%, and then 30% sucrose in PBS at 4° C. Coronal sections (50 µm) were prepared on a freezing microtome (HM 430 Sliding Microtome, Thermo Scientific Inc.). Consecutive sections (500 µm apart) were mounted and examined with a fluorescence microscope (Leica EL6000). For quantitative immunohistochemistry (FIG. 7), free-floating sections were processed with 5% normal donkey serum, and 0.4% Triton X-100 for 60 min. Sections were then exposed at 4° C. for 48 hr to primary antibodies against mouse monoclonal CaMKIIα (CaMKIIα, 1:500, 05-532, Millipore®, Billerica, Mass.). After washing with PBS, sections incubated for 2 hr at room temperature with Alexa Fluor® 647-conjugated AffiniPure donkey anti-mouse IgG (1:250, Jackson Laboratories, West Grove, Pa.). Slices were then washed and mounted (DAPI-Fluoromount G, SouthernBiotech, Birmingham, Ala.). Immuno-fluorescence was assessed with a laser confocal microscope (Leica CTR 6500).

For high-resolution, whole-brain fluorescence imaging (FIGS. 1A, 4H, and FIG. 8), frozen brains were embedded using stainless steel Tissue-Tek® base molds and Neg-50 embedding medium (Richard-Allan Scientific (Thermo); n=2 animals) (103). Post-freezing, the Neg-50 embedded brain was sectioned on a Microm™ HM550 cryostat using the tape-transfer method with all sections mounted directly onto slides. Alternating sections, cut at 20 µm, were separated to form two distinct series per brain. One slide series of the sectioned material was processed for Nissl cell body staining, using a thionin-based protocol and coverslipped with DPX mounting medium. The alternate series was dehydrated and directly coverslipped with DPX for fluorescence imaging. Whole-slide digital imaging was performed using a Hamamatsu NanoZoomer® 2.0-HT system at 0.46 µm/pixel, with fluorescence scans at 12-bit depth using a tri-pass filter cube. Following data conversion to lossless jp2 (JPEG2000), individual brain sections were aligned and registered using rigid two-dimensional (2-D) image transformation.

Figure 4E:
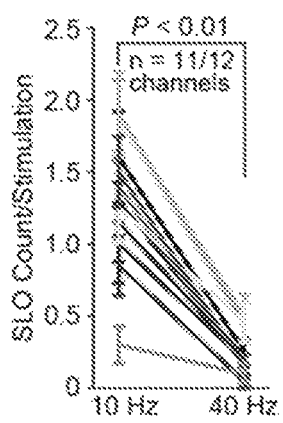
Figure 5A:
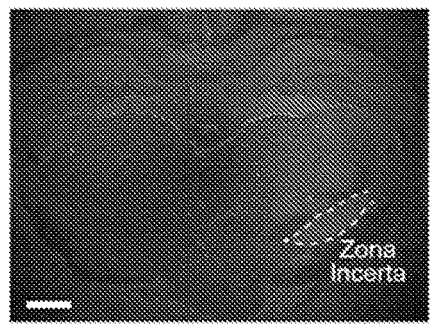
Figure 5B:
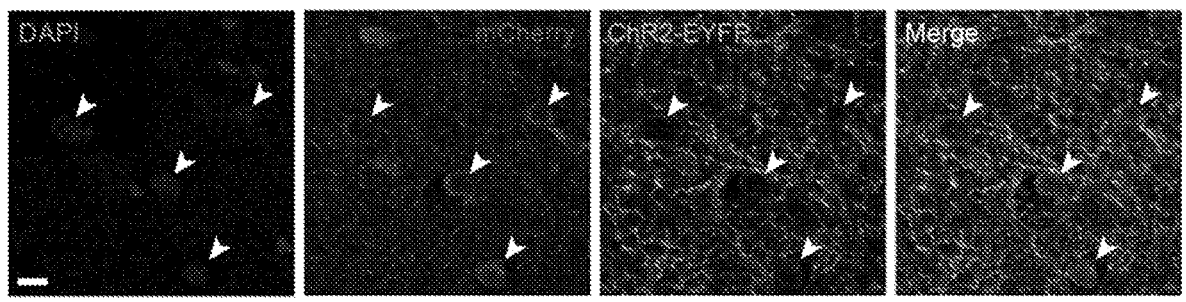
Figure 5C:
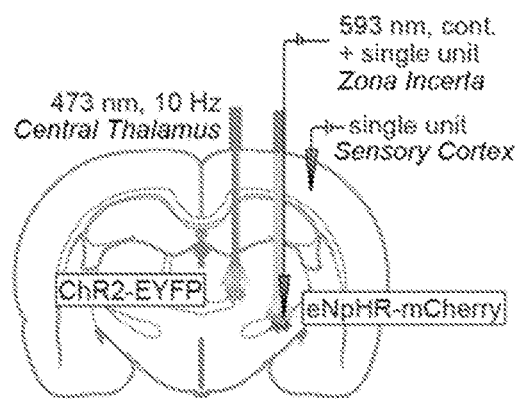
Figure 5G:
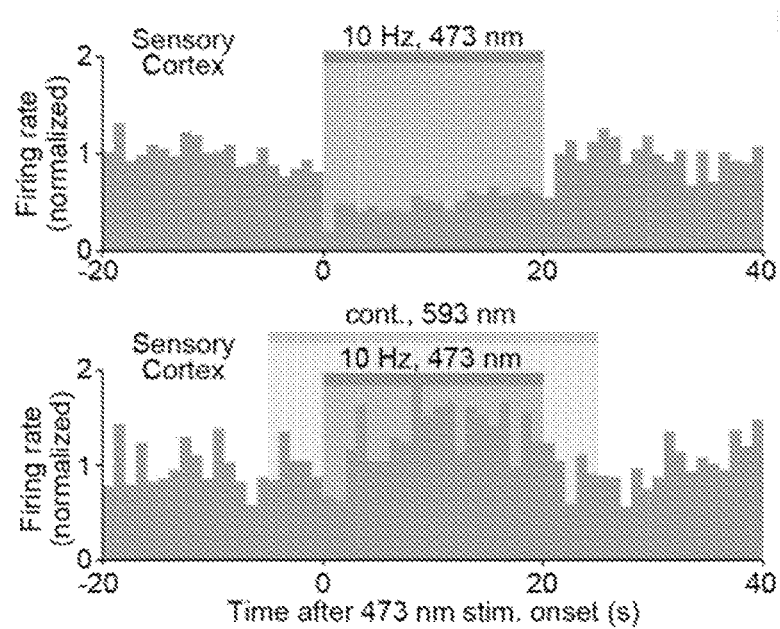
Figure 5H:
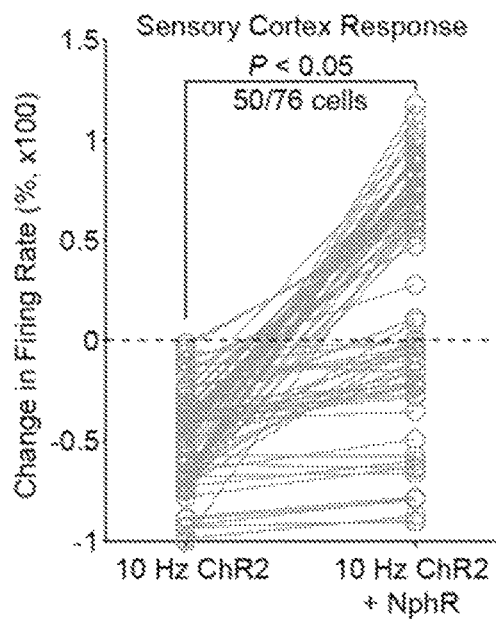
Figure 5I:
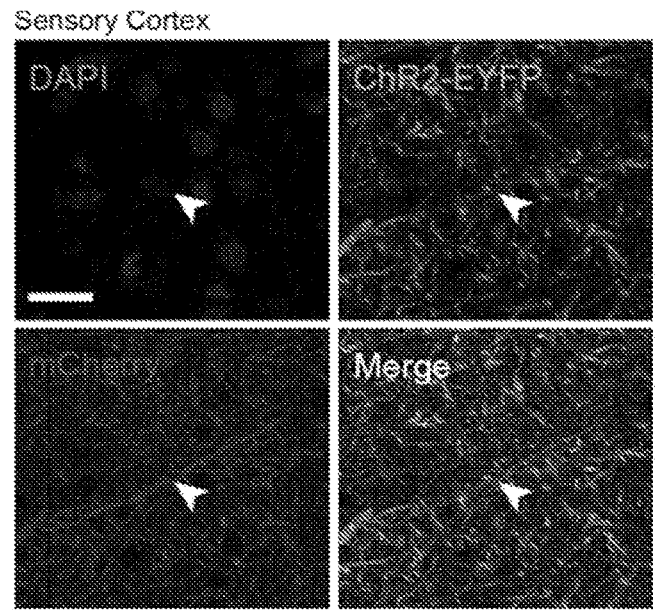

Statistics. All statistical tests were performed in Matlab®. Non-parametric tests were used throughout the analysis. For in vivo electrophysiology measurements at thalamus and zona incerta, one-tailed Wilcoxon signed-rank tests were used to evaluate changes in firing rate between the pre-stimulation and stimulation periods. For measurements at sensory cortex in FIG. 3G, a two-tailed version of the test was used to evaluate either increases or decreases in firing rate. For results in Table 1, the average pre-stimulus firing rate (20 s bin) was compared to the average firing rate of four 5 s bins over the 20 s period of stimulation using a one-tailed Wilcoxon signed rank test, uncorrected for multiple comparisons. One-sided Wilcoxon rank sum tests were used to evaluate differences in SLO occurrence (FIG. 4E), as well as changes in cortical or incertal firing when eNpHR activation was coupled with central thalamus stimulation (FIGS. 5F and 5H). For electrophysiology results, independence was assumed between repeated trials. All other assumptions for these tests were satisfied. For volumetric comparisons in FIG. 2E-G, one-sided Wilcoxon signed-rank tests were used to identify increases in the volume of BOLD activation between 10 and 40 Hz and 10 and 100 Hz (corrected for multiple comparisons). Note that variance was generally similar across groups being compared. Significance was determined at the $\alpha=0.05$ cutoff level. No statistical methods were used to estimate sample size. All statistical tests used to compare changes with frequency (FIGS. 2E-2G, and FIG. 9B) were performed pairwise, with an equal number of animals used for each frequency.

Figure 7:
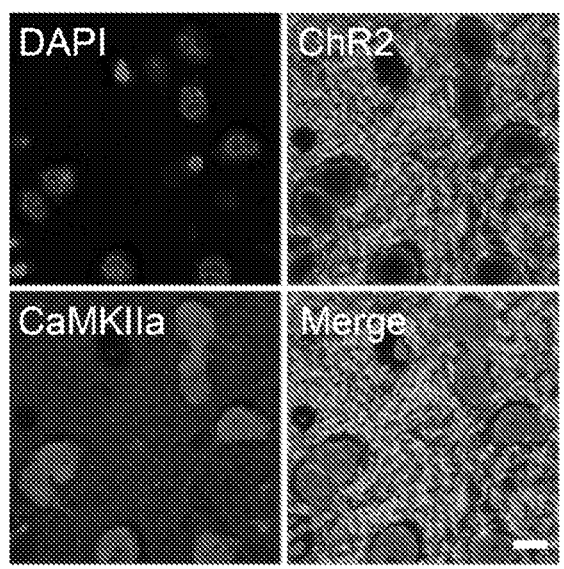
FIG. 7 is a collection of images showing specificity of ChR2 targeting for CaMKIIa-positive cells.

Example 2: High-Frequency Stimulation of Central Thalamus Relay Neurons Drives Widespread Forebrain Activation In Vivo To investigate the specific role of central thalamus, optogenetic techniques were applied to control relay cells in a spatially and temporally precise manner. A stereotactic injection in the right CL and PC intralaminar nuclei of central thalamus was performed with adeno-associated virus carrying channelrhodopsin-2 (ChR2) and the fluorescent reporter protein EYFP under control of the CaMKIIa promoter. This promoter is expressed primarily in excitatory neurons, the vast majority of which in thalamus are relay cells. 35% of cells identified within the bulk injection area were EYFP-positive, and 97% of EYFP-positive cells co-expressed CaMKIIa, indicating high sensitivity for stimulation of excitatory neurons (n=2 rats, 831 cells; FIG. 7). While ChR2-EYFP expression extended beyond these two nuclei (FIG. 1A), targeted stimulation of the intralaminar nuclei was achieved by (a) stereotactic placement of the implanted optical fiber, as confirmed with high-resolution T2-weighted structural MR images (FIG. 1B,C), and (b) spatially restricted illumination (FIG. 1A,B). 47 rats were initially injected and cannulated using the central thalamus as the stereotactic target (−3.2 mm AP, +1.5 mm ML, −5.5 mm DV). However, the intralaminar nuclei are relatively small and difficult to accurately target. Therefore only a subset of these animals were used based on the empirically observed distribution of optical fiber tip locations using T2-weighted MRI scans (FIG. 1B; <0.85 mm distance from target coordinate). Of the 18 rats that had an accurately localized implant location, two exhibited a general absence of fMRI activity—most notably at the site of stimulation—and were excluded, leaving 16 animals for further analysis.

FIG. 1. Targeted stimulation of central thalamus evokes positive BOLD changes and increases in neuronal firing at the site of stimulation. (FIG. 1A) Representative wide-field fluorescence image shows robust ChR2-EYFP expression throughout central thalamus, overlaid with the estimated cone of excited tissue shown to scale. (FIG. 1B) Empirically observed locations of fiber optic implants in initial cohort of 47 rats, estimated using high-resolution structural MRI scans. 18 of these animals had implant locations that were accurately localized to the central thalamus (<0.85 mm from target site, shown as dashed circle and cross). Two were excluded based on lack of thalamic activation, leaving n=16 rats for further analysis. Black dots indicate implant coordinates of 16 animals used for analysis. Gray dots indicate implant coordinates of 31 rejected animals. (FIG. 1C) Representative T2-weighted anatomical MRI scan used to estimate implant location, marked with arrow. (FIG. 1D) Schematic of 23 coronal slices acquired during ofMRI experiments. Slice numbers correspond to activation maps in FIG. 2. (FIG. 1E) Average time series of significantly modulated voxels within the ipsilateral thalamus ROI (see FIG. 2D) exhibit robust positive BOLD responses during repeated 20 s periods of stimulation at 10, 40, and 100 Hz, indicated by blue bars. Values are mean±s.e.m. across animals (n=16, 10, and 16 for each frequency, respectively). (FIG. 1F) Diagram of local in vivo optrode recordings during optical stimulation of central thalamus. Inset shows spike waveforms of recorded neurons. (FIG. 1G) Representative peri-event time histogram of a recorded neuron showing the increase in firing rate within central thalamus during optical stimulation at each of the three frequencies tested. See also FIG. 7.

FIG. 7. Specificity of ChR2 targeting for CaMKIIa-positive cells.

Immunohistochemistry confirms the specific targeting of ChR2-EYFP to CaMKIIa-positive neurons in central thalamus. 35% of cells identified within the bulk injection area were EYFP-positive, and 97% of EYFP-positive cells co-expressed CaMKIIa (n=2 rats, 831 cells). Scale bar, 10 μm.

In order to achieve a small volume of directly excited tissue limited to the intralaminar nuclei, a 62.5 μm diameter optical fiber was used. Assuming that an intensity of 1 $mW/mm^2$ is required for ChR2 activation, the specific power exiting from the fiber optic's tip in these experiments (2.5 mW) corresponds to a penetration depth of 1.08 mm and a volume of 0.08 $mm^3$ over which ChR2+ neurons can be excited. FIG. 1A illustrates this penetration depth and activation cone (11.7° half-angle of divergence) to scale with the targeted nuclei, showing that stimulation is well restricted to the central thalamus. These two factors (MR-validated stereotactic fiber placement and a small volume of excited tissue) suggest that the effects reported here primarily derive from stimulation of excitatory relay neurons within the central thalamus.

Figure 8:
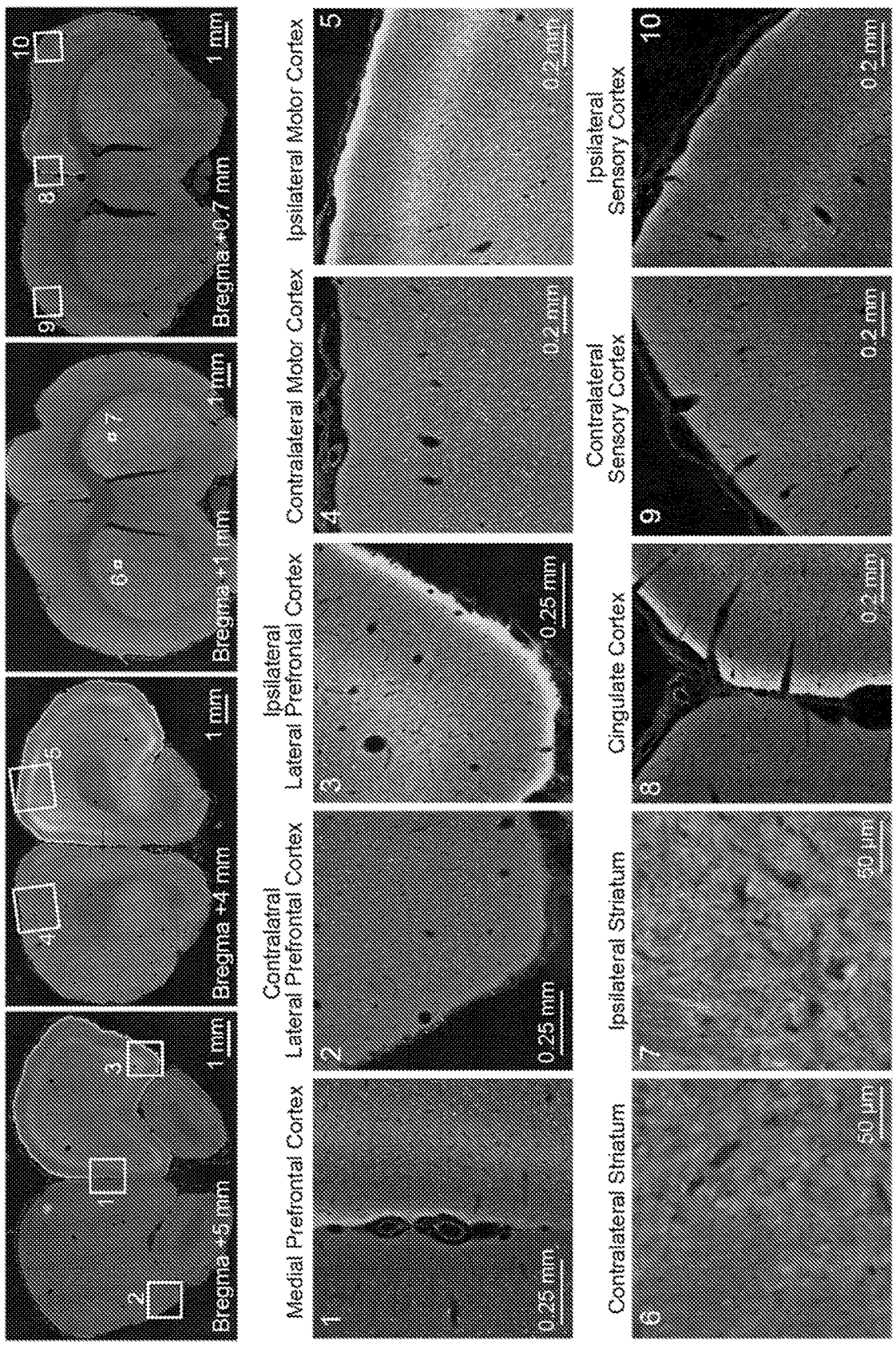
FIG. 8 is a collection of images showing representative fluorescence images of ChR2-EYFP at remote targets, illustrating the massive projections to forebrain from transfected relay neurons in the right central thalamus.

To explore the anatomical connectivity of transfected neurons in central thalamus, ex vivo fluorescence microscopy images of ChR2-EYFP expression were collected. Due to the spread of viral transfection (FIG. 1A), it is possible that the reported fluorescence reflects projections from adjacent thalamic nuclei as well. Nevertheless, in agreement with known projection systems of central thalamus, EYFP-expressing axons were observed throughout forebrain, including frontal cortex and striatum (FIG. 8). In particular, the medial prefrontal, lateral prefrontal, cingulate, motor, and sensory cortices all received strong projections. This input was highly convergent at the superficial layers, with moderate but weaker projections present in middle layers as well. Furthermore, projections were significantly restricted to the hemisphere ipsilateral to virus injection for both cortex and striatum. While these anatomical connections provide a strong foundation for understanding how central thalamus can influence brain state, they do little to explain the dynamic nature of these circuits—for example, how stimulation of central thalamus at different frequencies can lead to distinct behavioral responses. Therefore, to dissect the functional significance of these massive forebrain projections and visualize the large-scale spatial and temporal dynamics evoked by central thalamus stimulation, optical stimulation with simultaneous in vivo whole-brain functional imaging was combined.

FIG. 8. Representative fluorescence images of ChR2-EYFP at remote targets illustrate the massive projections to forebrain from transfected relay neurons in the right central thalamus. The bottom two rows provide magnified images of cortical and striatal regions used for quantitative ofMRI analysis. The top row provides the whole-brain slices from which these magnified images come. EYFP-expressing axonal projections are primarily localized to the ipsilateral hemisphere and to superficial layers in cortex.

Figure 1E:
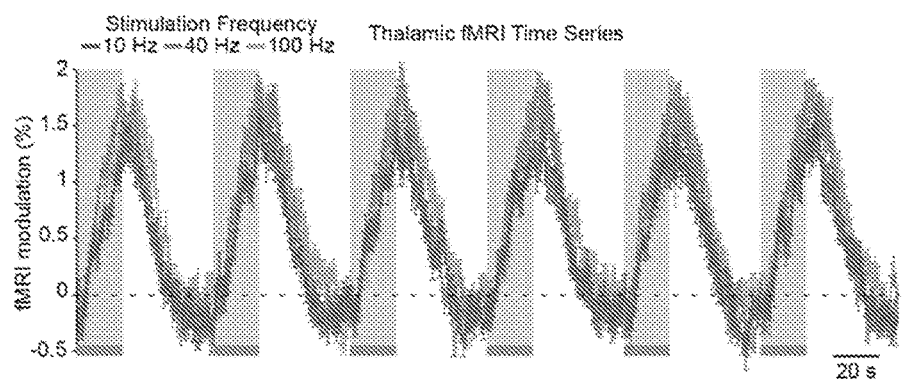
Figure 1F:
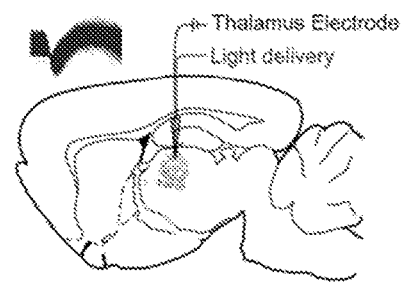
Figure 1G:
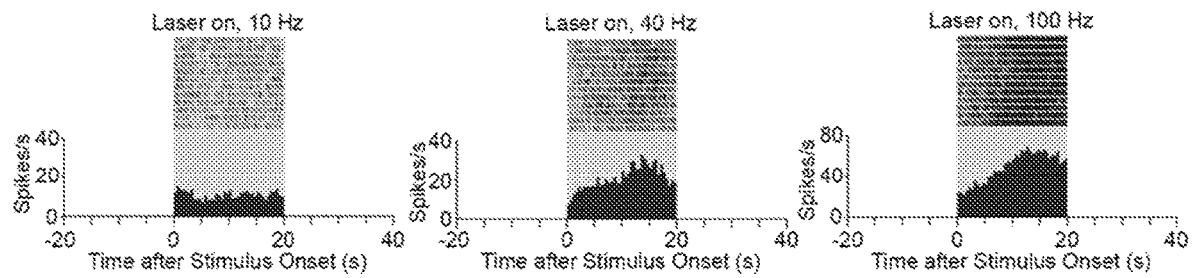

During optogenetic fMRI experiments, twenty-three coronal slices with 0.5×0.5 $mm^2$ in-plane resolution and 0.5 mm thickness were acquired at a frame rate of 750 ms using spiral k-space trajectories and a sliding window reconstruction algorithm to achieve high spatiotemporal resolutions with whole-brain coverage (bregma +5.2 to −5.3 mm; FIG. 1D). Novel inverse Gauss-Newton methods were also used to correct for possible motion artifacts and optimize the robustness of detecting optogenetically-evoked responses. For each experiment, 20 s periods of stimulation were delivered every minute for 6 minutes at 10, 40, or 100 Hz. This form of continuous steady-state stimulation mimics the approach used in clinical DBS and has been showed to evoke robust fMRI responses with optogenetic stimuli. Indeed, stimulation at all three frequencies resulted in a robust positive blood-oxygen-level-dependent (BOLD) signal at the site of stimulation that was highly synchronized to light delivery, increased upon optical activation, and gradually returned to baseline following the end of stimulation (FIG. 1E). To confirm that this BOLD signal reflected underlying neuronal firing patterns, simultaneous single-unit recordings was performed with stimulation using an optrode at the central thalamus (FIG. 1F). In agreement with the fMRI signal, stimulations at 10, 40, and 100 Hz all resulted in robust increases in the local neuronal firing rate (FIG. 1G; n=5 neurons, $P<0.05$, Wilcoxon signed-rank test between the 20 s pre-stimulation and stimulation periods, 12 trials for each neuron).

Figure 2A:
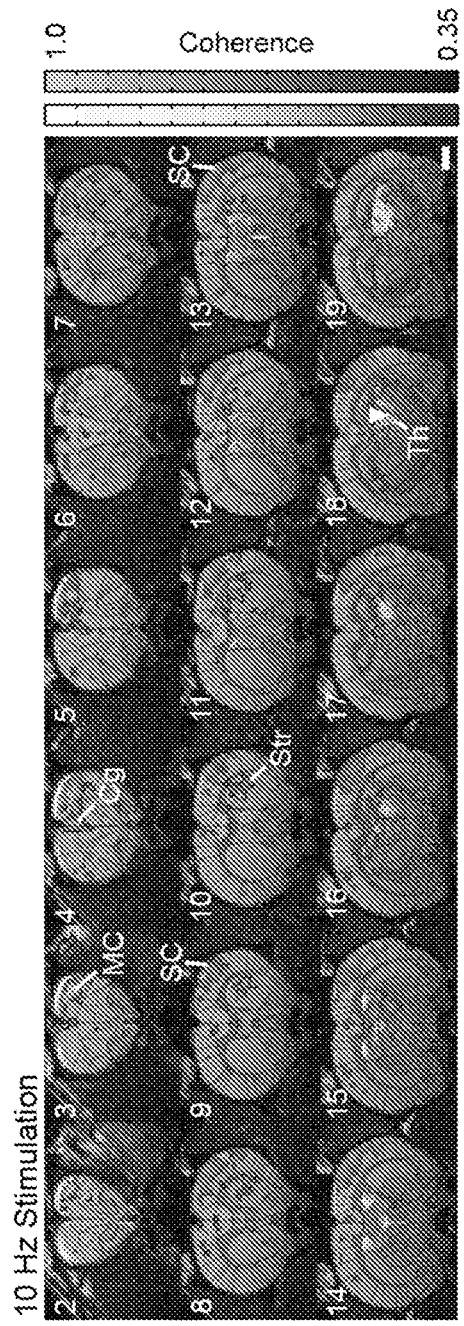
Figure 2B:
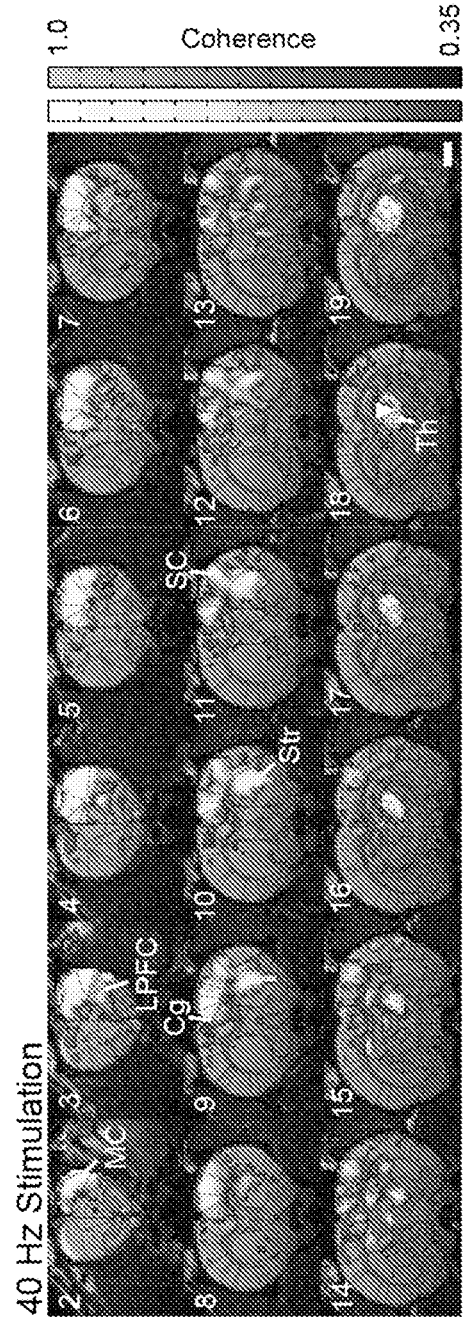
Figure 2C:
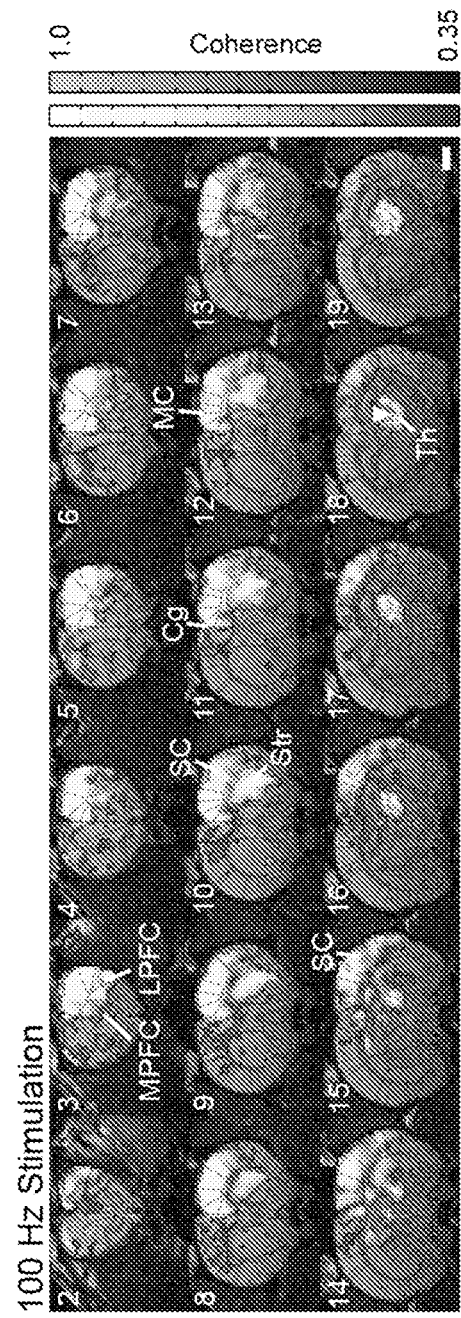
Figure 2D:
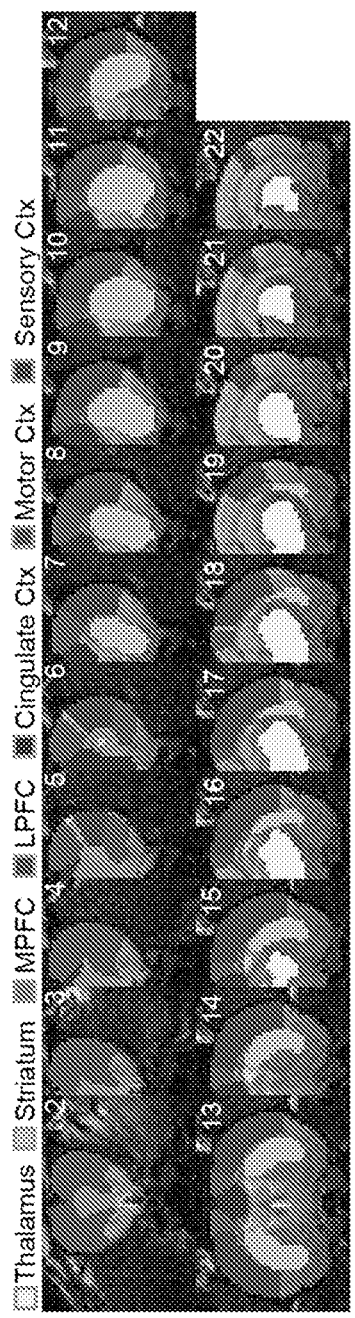

Both locally in the thalamus and at downstream, synaptically connected brain regions, the frequency of stimulation had an effect in determining the extent of ipsilateral and contralateral BOLD activation—defined here as positive BOLD signals significantly synchronized to the block stimulation paradigm (see Example 1). In general, a much larger volume of brain tissue was activated by stimulation at 40 and 100 Hz compared to 10 Hz, with frontocortical areas and striatum being strongly activated at high frequencies (FIG. 2A-2C). To quantify these spatial differences in recruitment patterns, the total volume of positive and statistically significant BOLD signals evoked by stimulation in select ROIs was calculated (FIG. 2D). This difference in activation volume between low (10 Hz) and high (40 or 100 Hz) stimulation frequencies was significant at the thalamus, striatum, and medial prefrontal, lateral prefrontal, cingulate, motor, and sensory cortices (FIG. 2E-G). Striatal activity was primarily localized to the dorsal sector, with negligible activity occurring in the ventral region (FIG. 2B,C). Furthermore, BOLD activation was generally restricted to the ipsilateral hemisphere, although activation volumes in the contralateral striatum, lateral prefrontal cortex, motor cortex, and sensory cortex were all significantly greater during 100 Hz stimulation compared to 10 Hz stimulation (FIG. 2F-H).

FIG. 2. Spatial characterization of evoked fMRI signals. (FIGS. 2A-2C) Average coherence maps of brain-wide activity during stimulation of excitatory central thalamus relay neurons at 10, 40, and 100 Hz. Warm colors indicate positive BOLD responses, while cool colors indicate negative BOLD responses (see Methods). (FIG. 2D) Regions of interest (ROIs) used for quantitative analysis of spatial ofMRI activation patterns. (FIG. 2E) The amount of active volume (positive signal with coherence >0.35) in the ipsilateral thalamus is significantly greater during 40 and 100 Hz stimulations than 10 Hz stimulation. Thalamic recruitment is relatively limited on the contralateral side. (FIG. 2F) Activation of the ipsilateral striatum is significantly greater during 40 and 100 Hz stimulations than 10 Hz stimulation. Activation of the contralateral striatum is limited across frequencies, although there is an increase from 10 to 100 Hz. (FIG. 2G) Medial and lateral prefrontal cortex exhibit a significantly greater volume of activation during 40 and/or 100 Hz stimulation than 10 Hz stimulation. Activity in the contralateral hemisphere is limited across all tested frequencies, although there is an increase from 10 to 100 Hz. (FIG.

2H) Activation of cingulate, motor, and somatosensory cortex is each greater during 40 and 100 Hz stimulations than 10 Hz stimulation. The contralateral motor and sensory cortices are also activated to a greater extent during 40 and/or 100 Hz stimulation. Scale bars in FIG. 2A through FIG. 2C represent 2 mm. Asterisks in FIG. 2E through FIG. 2H indicate significant differences for 10 versus 40 Hz and 10 versus 100 Hz stimulations. *$P<0.05$, $P<0.005$, *$P<0.001$, one-sided Wilcoxon signed-rank tests, corrected for multiple comparisons. Error bars represent mean±s.e.m. across animals. n=16, 10, and 16 animals for 10, 40, and 100 Hz, respectively. Abbreviations are as follows: i—(ipsilateral), c—(contralateral), Cg (cingulate cortex), MC (motor cortex), MPFC (medial prefrontal cortex), LPFC (lateral prefrontal cortex), SC (sensory cortex), Str (striatum), Th (thalamus). See also FIGS. 8, 9A-9B, and 10A-10C.

Figure 9A:
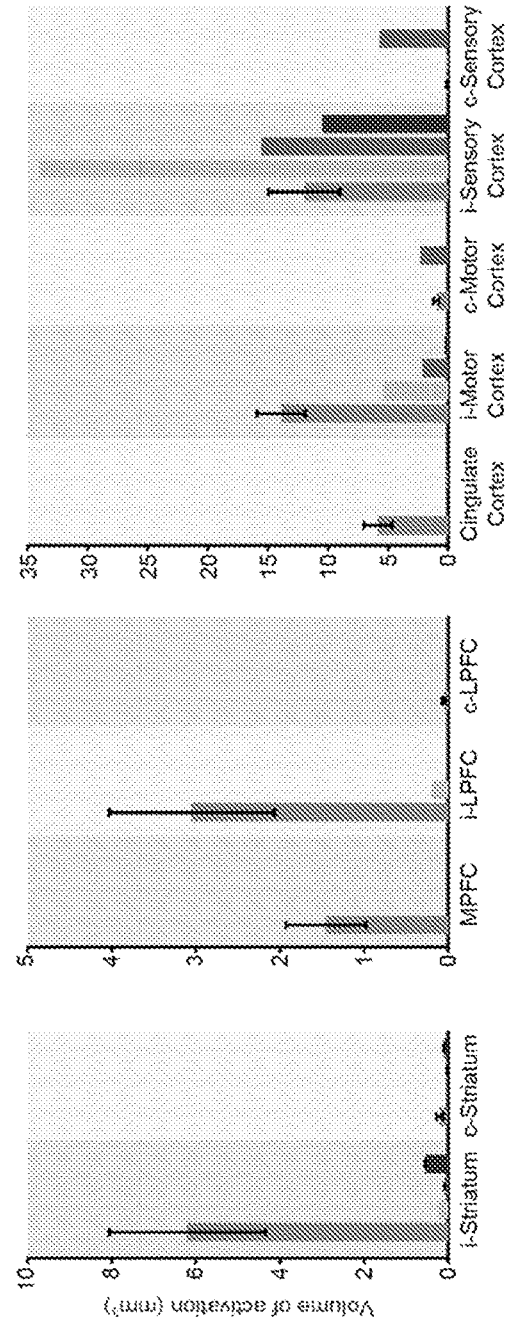
FIGS. 9A-9B are a collection of graphs showing that widespread and frequency-dependent recruitment of forebrain with optogenetics is distinct to stimulation of intralaminar nuclei of central thalamus, according to embodiments of the present disclosure.

These results provide a direct, region-specific visualization of the widespread driving effect that central thalamus has been shown to exert over forebrain, and link prior anatomical and physiological studies on arousal regulation to spatially precise and quantitative measures of cortical and striatal activation. For example, the evoked responses are consistent with the unilateral nature of thalamocortical projections (FIG. 8), but reveal that the contralateral cortex can still be modulated by unilateral stimulation of central thalamus, particularly at high frequencies. Importantly, stimulation of other thalamic nuclei failed to evoke similarly widespread activity in the striatum and cortex (FIG. 9A). Furthermore, large differences in forebrain activation between 10 and 40 Hz stimulations were not observed for other forms of subcortical stimulation (FIG. 9B), suggesting this is a distinct property of central thalamus.

Figure 9B:
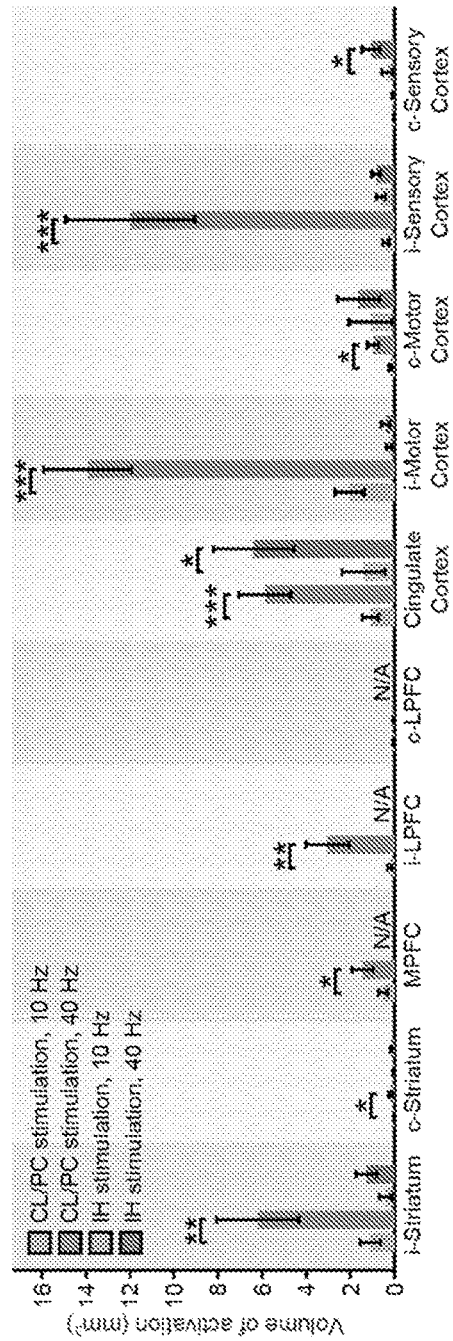

FIGS. 9A-9B. Widespread and frequency-dependent recruitment of forebrain with optogenetics is distinct to stimulation of intralaminar nuclei of central thalamus. (FIG. 9A) Volumes of striatal and cortical activation (i.e. positive BOLD signals with coherence greater than 0.35) during 40 Hz stimulation of central thalamus, presented with activation volumes during stimulation of other thalamic nuclei. Central thalamus is the only target to result in significant recruitment of striatum and prefrontal and frontal cortical regions. (FIG. 9B) Comparison of frequency dependent effects of central thalamus stimulation with those of intermediate hippocampus (IH) stimulation. Unlike central thalamus stimulation, which recruits significantly more volume in striatum, motor cortex, and sensory cortex at 40 Hz than at 10 Hz (*$P<0.05$, $P<0.005$, *$P<0.001$; one-sided Wilcoxon signed-rank test), recruitment of these regions during hippocampal stimulation does not exhibit a significant dependence on frequency. Note that activation data was not available (N/A) at MPFC or LPFC for hippocampus stimulation due to differences in field of view. Abbreviations are as follows: i—(ipsilateral), c—(contralateral), Cing. ctx (cingulate cortex), MPFC (medial prefrontal cortex), LPFC (lateral prefrontal cortex), Sens. ctx (sensory cortex).

Figure 10A:
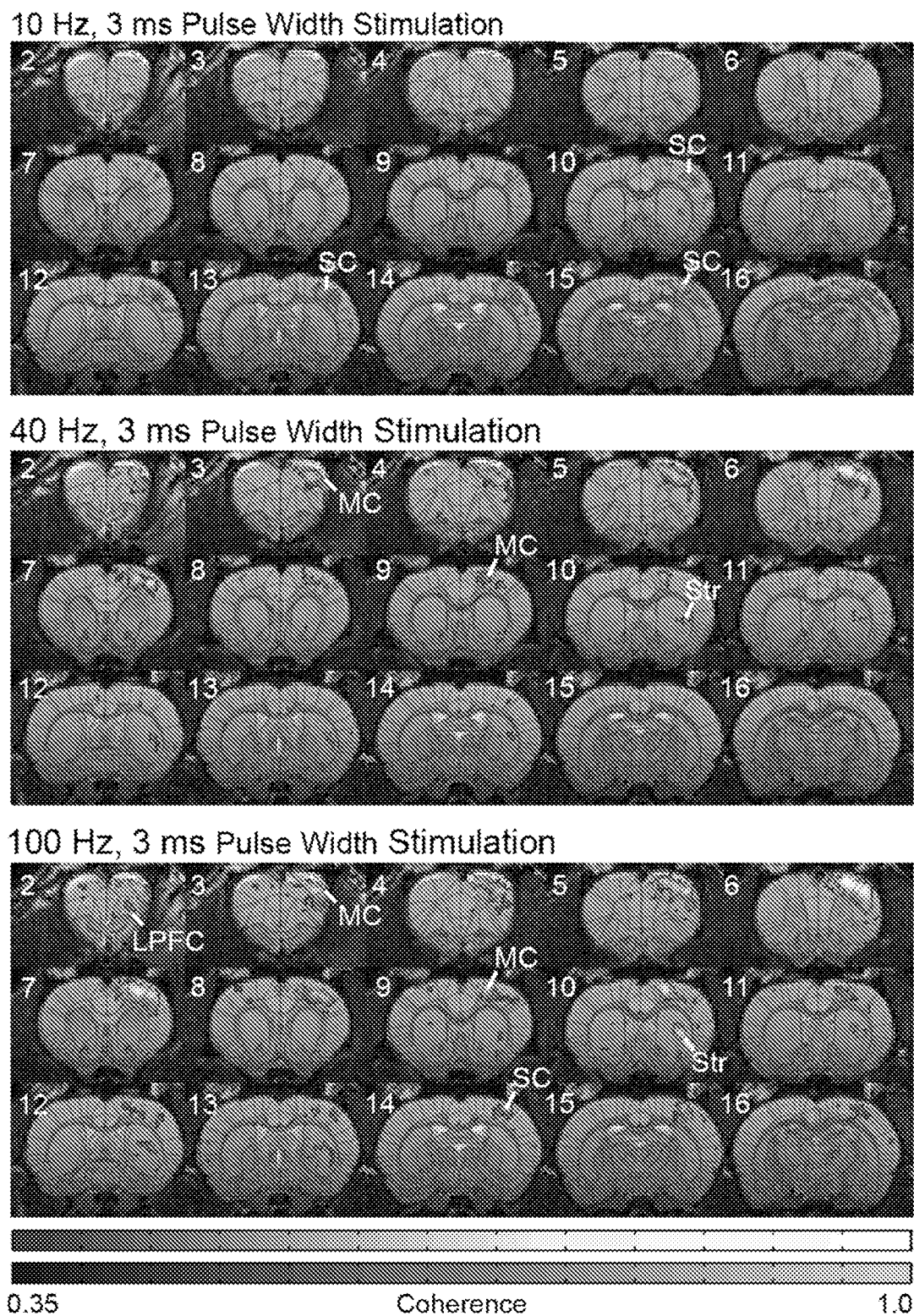
FIGS. 10A-10C are a collection of images and graphs showing that the frequency-dependent recruitment of forebrain by central thalamus and its control over cortical BOLD signal polarity are preserved when pulse width is held constant.
Figure 10B:
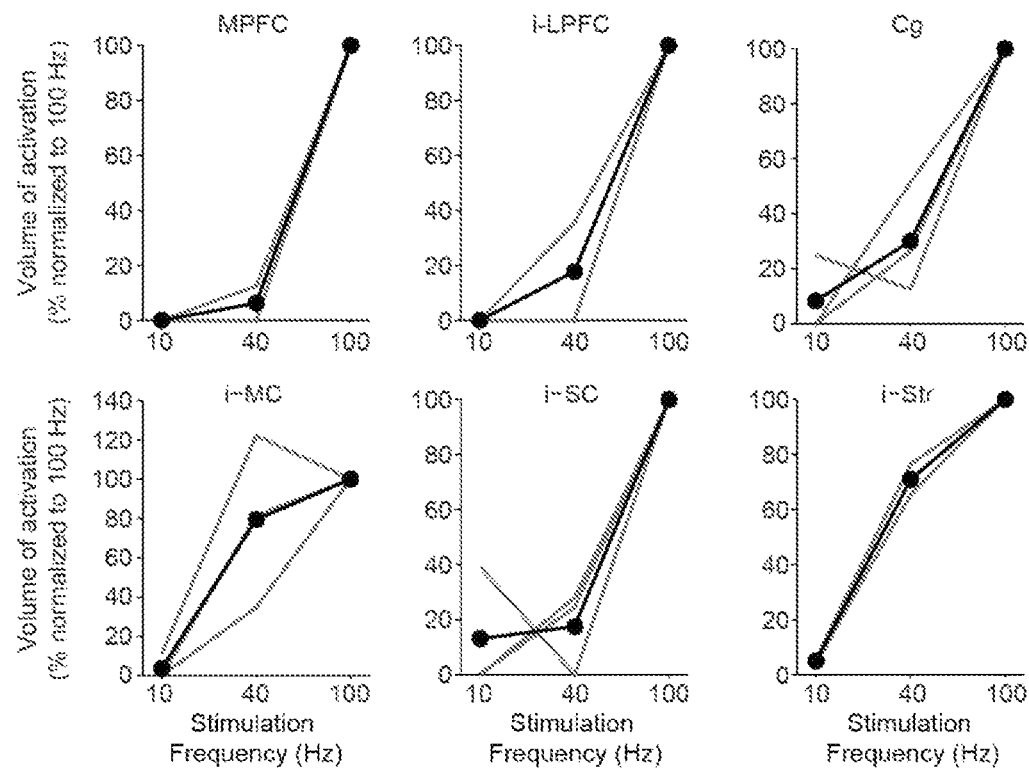

Throughout these experiments, a constant duty cycle of 30% was used to maintain the total amount of light delivery across frequencies and control for possible heating artifacts. Because 20 s pulse train was kept for all stimulation frequencies and avoid possible differences introduced by neuronal adaptation, maintaining a constant duty cycle required unique pulse widths for each frequency (i.e. 30, 7.5, and 3 ms for 10, 40, and 100 Hz, respectively). To rule out the possibility that these changes in pulse width were the primary cause of the above differences in forebrain recruitment, stimulations were repeated while maintaining a 3 ms pulse width. Visualization and quantification of evoked fMRI responses show that the increase in cortical and striatal activation with frequency was preserved (FIGS. 10A and 10B). These data suggest that stimulation frequency was the primary factor in modulating forebrain fMRI activation.\

Figure 10C:
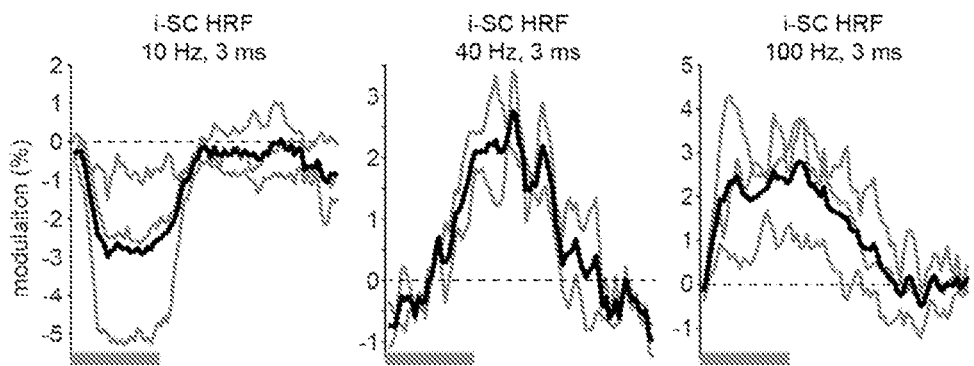

FIGS. 10A-10C. The frequency-dependent recruitment of forebrain by central thalamus and its control over cortical BOLD signal polarity are preserved when pulse width is held constant. (FIG. 10A) Representative coherence map of brain-wide activity during stimulation of excitatory central thalamus relay neurons at 10, 40, and 100 Hz using a constant pulse width of 3 ms. Warm colors indicate positive BOLD responses, while cool colors indicate negative BOLD responses (see Example 1). (FIG. 10B) Quantification of positive BOLD responses in cortex and striatum (n=3 animals). Gray lines indicate animal-specific results, normalized to 100 Hz stimulation. Black lines indicate the average across animals. All six regions exhibit an increase in recruitment with frequency, consistent with the study's main results when pulse width was varied to keep the duty cycle and total amount of light delivery constant. Regions of interest (ROIs) are the same as those used in FIG. 2. (FIG. 10C) Hemodynamic response functions evoked in somatosensory cortex during 10, 40, and 100 Hz stimulation of central thalamus using a constant pulse width of 3 ms. Consistent with the study's main results, a negative BOLD signal is evoked at 10 Hz, while slow and fast positive BOLD responses are evoked at 40 and 100 Hz, respectively.

Figure 3A:
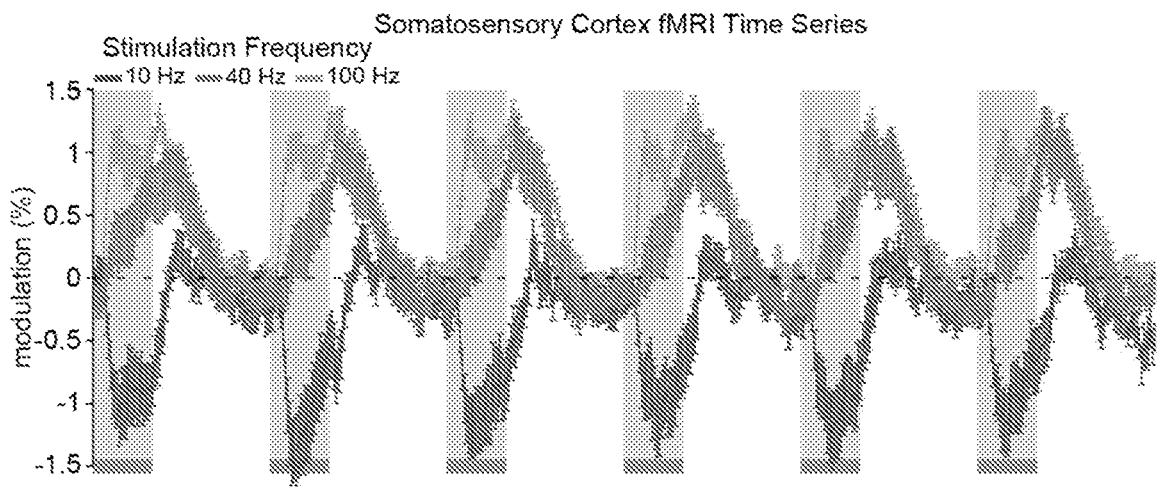
FIGS. 3A-3E are a collection of graphs and diagrams showing that the sign of evoked cortical activity depends on the frequency of central thalamic stimulation, according to embodiments of the present disclosure.
Figure 3B:
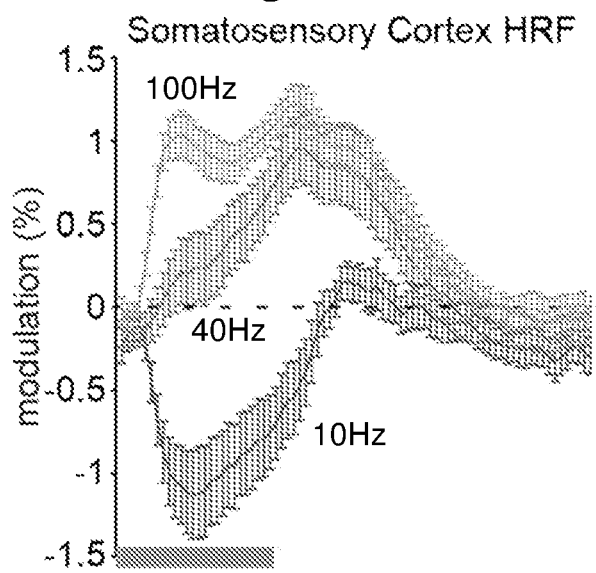

Example 3: Central Thalamus Stimulation Frequency Controls Cortical Excitation/Inhibition Balance The temporal dynamics of cortical responses evoked during low- and high-frequency central thalamus stimulation were next examined. Despite targeted activation of excitatory neurons, the somatosensory cortex exhibited a strong negative BOLD signal during 10 Hz stimulation, suggesting a suppression of baseline activity (FIGS. 2A and 3A, 3B). In stark contrast, central thalamus stimulations at 40 and 100 Hz led to positive changes in the BOLD signal at the somatosensory cortex (FIGS. 2B, 2C and 3A, 3B). Thus, stimulation of the same excitatory population at different frequencies resulted in completely opposite responses at a downstream target. Importantly, these responses were preserved when pulse width was held constant in control experiments, indicating that stimulation frequency was the primary factor controlling this effect (FIGS. 10A and 10C).

FIG. 3. The sign of evoked cortical activity depends on the frequency of central thalamic stimulation. (FIGS. 3A, 3B) 10 Hz stimulation of central thalamus evokes a strong negative BOLD signal throughout ipsilateral somatosensory cortex, while 40 and 100 Hz stimulations evoke positive responses. Time series come from the sensory cortex ROI defined in FIG. 2D. Hemodynamic response function (HRF) shows the average response to a single 20 s period of stimulation, indicated by blue bar. Error bars represent mean±s.e.m. across animals. n=16, 10, and 16 for 10, 40, and 100 Hz, respectively. (FIG. 3C) Diagram of in vivo recordings at somatosensory cortex during stimulation of excitatory central thalamus relay neurons. Inset shows spike waveforms of recorded neurons. (FIGS. 3D, 3E) Representative peri-event time histogram of a recorded neuron, and corresponding quantification of firing rate during the 20 s periods before, during, and after stimulation. Neural firing rate decreased within the somatosensory cortex during 10

Hz central thalamus stimulation, but increased during 40 and 100 Hz stimulations (n=17 trials each, *P<0.05, ***P<0.001 pre vs. ON, two-tailed Wilcoxon signed-rank test; see Table 1 for further analysis). Values are mean±s.e.m. See also FIG. 10.

Figure 3C:
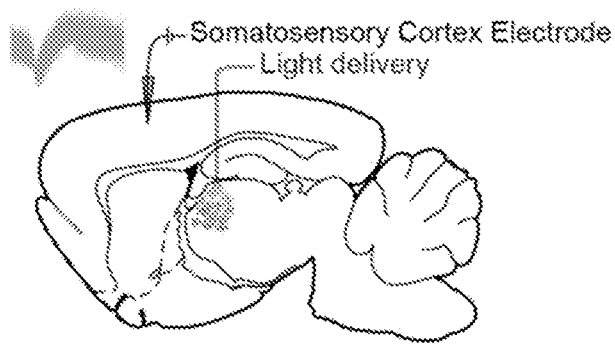
Figure 3D:
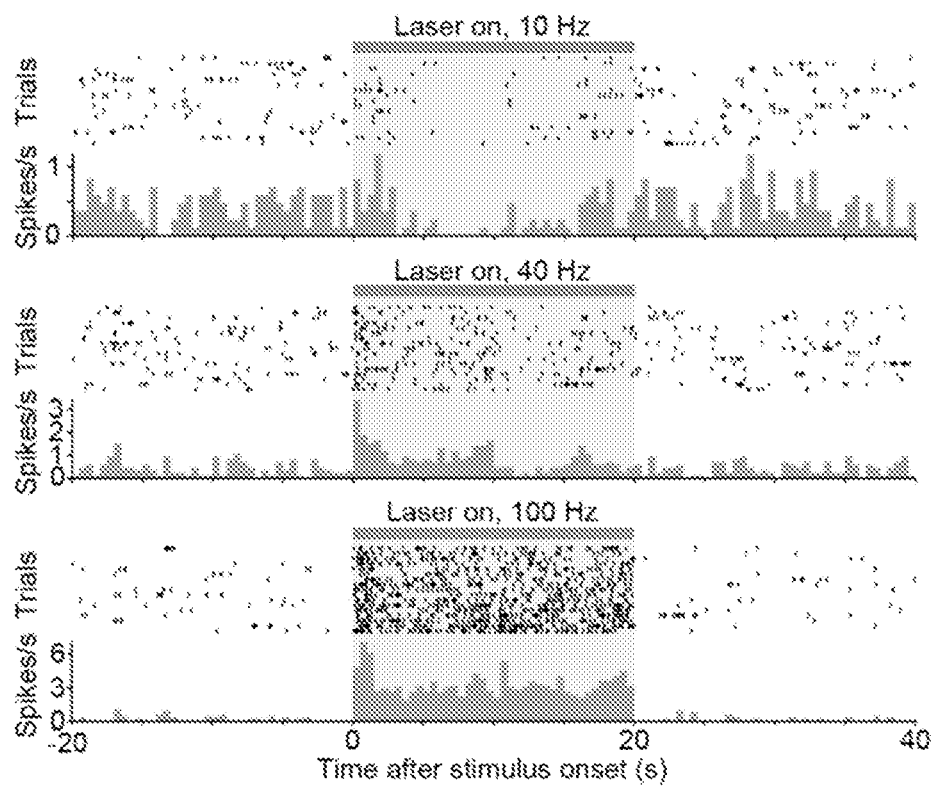
Figure 3E:
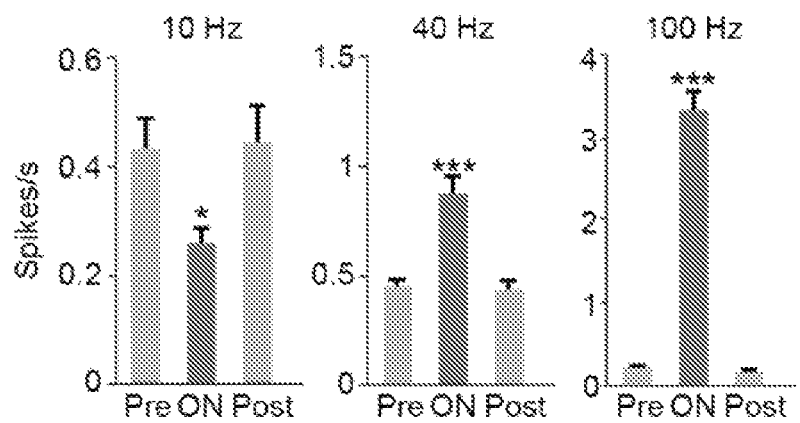
Figure 11:
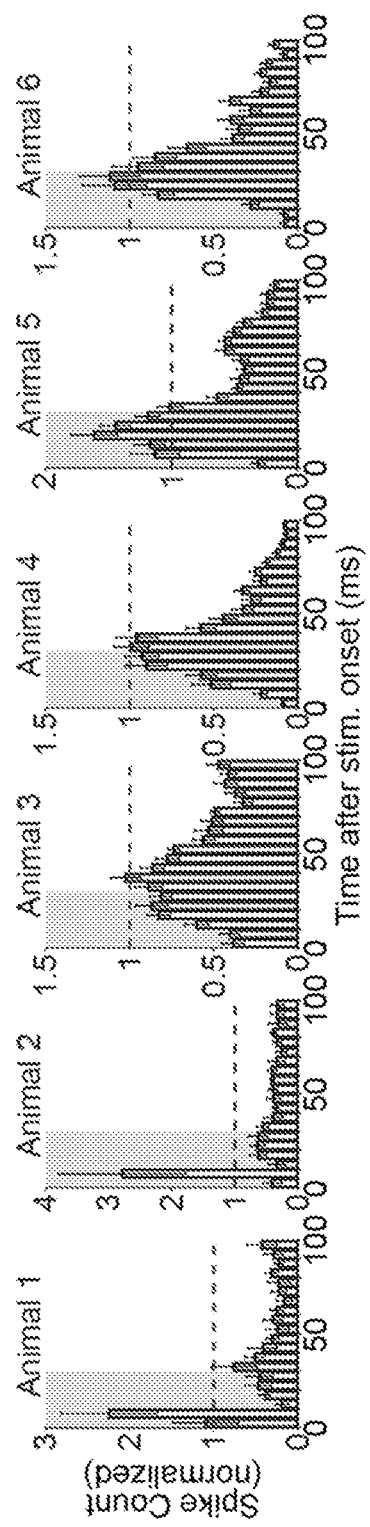
FIG. 11 is a collection of graphs and a table showing that cortical spikes that occur during periods of inhibition driven by 10 Hz central thalamus stimulation exhibit a non-uniform distribution over time, according to embodiments of the present disclosure.

While similar findings of frequency-dependent polarity changes have been hinted at in previous studies, downstream positive and negative BOLD signals that result from selective stimulation of excitatory neurons at distinct frequencies have not yet been visualized and validated with electrophysiology. To define the neuronal underpinnings of these signals, single-unit extracellular recordings were performed in the somatosensory cortex during central thalamus stimulation (FIG. 3C). In agreement with the BOLD activity observed during ofMRI experiments, 10 Hz stimulation resulted in a decrease in neuronal firing rate between pre-stimulation and stimulation periods (FIGS. 3D, 3E; n=10 of 11 recorded neurons). Conversely, stimulations at 40 and 100 Hz both led to increases in neuronal firing (FIGS. 3D, 3E; n=11 of 11 recorded neurons). Because the evoked firing rates appeared to change over the course of stimulation, the pre-stimulation firing rate to the average firing rates were specifically compared during consecutive 5 s periods of the 20 s stimulus (i.e. 0-5 s, 5-10 s, 10-15 s, and 15-20 s; uncorrected P<0.05, Wilcoxon signed rank test; 17 trials for each neuron). Interestingly, the decrease in firing rate during 10 Hz stimulation occurred primarily over the interval from 5 to 15 s after stimulation began, while the increase in firing rate during 40 Hz stimulation occurred primarily over the first 10 s (Table 1). On the other hand, the increase in neuronal firing rate during 100 Hz stimulation was generally maintained throughout the 20 s stimulation period (Table 1). Such differences may reflect short-term plasticity of the thalamocortical pathway, which has previously been shown to exhibit frequency-dependent properties. Peri-stimulus time histograms also revealed that spike events occurring during inhibition had a non-uniform distribution over time, which peaked between 6 and 34 ms after light onset (FIG. 11). These data suggest that the glutamatergic thalamocortical input at 10 Hz sometimes generated action potentials. Notably, however, not every light pulse resulted in an immediate action potential.

TABLE 1

Electrophysiology results from sensory cortex single-unit recordings.

| Stimulation Frequency | Effect on Sensory Cortex Firing Rate | Percentage of neurons with significant change in firing rate (n = 11) | | | |
|---|---|---|---|---|---|
| | | 0-5 s after stim. onset | 5-10 s after stim. onset | 10-15 s after stim. onset | 15-20 s after stim. onset |
| 10 Hz | Increase | 0% | 0% | 0% | 0% |
| | Decrease | 0% | 91% | 82% | 9% |
| 40 Hz | Increase | 100% | 91% | 36% | 55% |
| | Decrease | 0% | 0% | 0% | 0% |
| 100 Hz | Increase | 100% | 82% | 82% | 82% |
| | Decrease | 0% | 0% | 0% | 0% |

See also Table 1-source data 1.

FIG. 11. Cortical spikes that occur during periods of inhibition driven by 10 Hz central thalamus stimulation exhibit a non-uniform distribution over time. (Top panels) Average peristimulus time histograms (PSTHs) of spike events in somatosensory cortex during 10 Hz central thalamus stimulation for six animals. Analysis was restricted to the 5 s time bin with the greatest number of neurons inhibited for each animal. PSTHs were calculated by aligning spike counts to the onset of individual 30 ms light pulses, summing over the 50 pulses delivered during the 5 s stimulation period, averaging across trials, and binning at 5 ms intervals for each inhibited neuron. Histograms were normalized by the corresponding spike count value during the 20 s pre-stimulation baseline period (represented by the dashed line), and averaged across neurons for each animal. Shaded rectangles represent the 30 ms light pulse. Note that spike events are reduced relative to baseline for the majority of the 100 ms inter-stimulus period, but spike events that do occur have a non-uniform distribution that peaks 6-34 ms after stimulus onset. These patterns suggest that some thalamic stimuli induce spike events in cortex, despite the net suppression of activity relative to pre-stimulation levels. Animals presented include two used for ChR2-electrophysiology experiments in Table 1 and four used for combined ChR2-eNpHR electrophysiology experiments in FIG. 5. (Bottom table) Summary of PSTH peak latencies and spike fidelity for inhibited neurons in somatosensory cortex. Peak latency was defined as the 5 ms bin with highest spike count for each neuron's PSTH. Spike fidelity represents the percentage of light pulses in the given 5 s bin of inhibition that evoke at least one spike during the 30 ms pulse. Values represent mean +/−s.t.e. across cells in the figure and table.

Together, these ofMRI and electrophysiological data indicate that neuronal activity throughout somatosensory cortex is suppressed at low frequencies of central thalamus stimulation and increased at high frequencies of stimulation. Because the stimulations were restricted to excitatory neurons with cell bodies located in central thalamus, the causal relationship between stimulation frequency and cortical excitation/inhibition can be attributed to the neurons' initial firing pattern. These results add to a growing body of literature in systems neuroscience suggesting that a neuronal population's firing pattern can have vastly different—even opposite—effects on downstream regions depending on its specific temporal code.

Figure 4A:
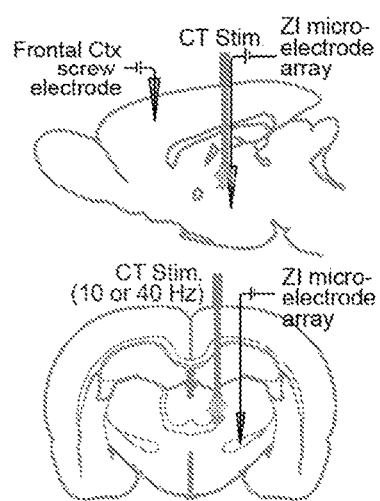
FIGS. 4A-4H are a collection of images, graphs and diagrams showing that Frequency-dependent spindle-like oscillations are evoked in zona incerta (ZI), according to embodiments of the present disclosure.
Figure 4B:
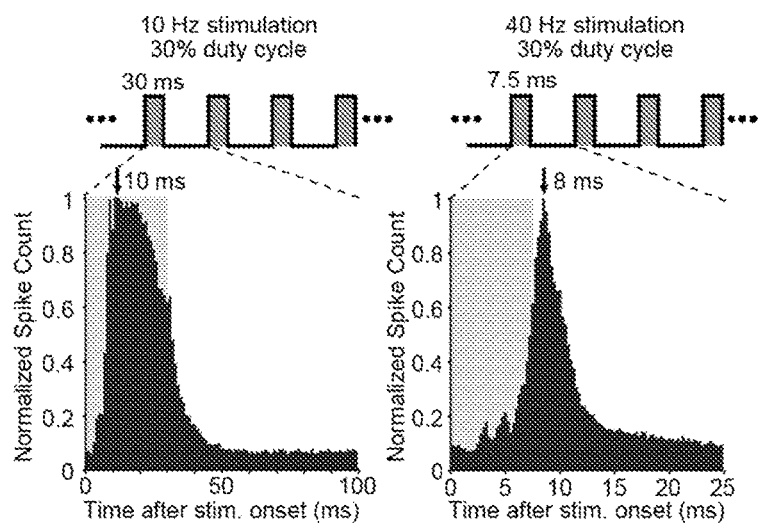

Example 4: Low-Frequency Central Thalamus Stimulation Drives Incertal Oscillations Given that stimulation was restricted to excitatory neurons, it was hypothesized that the suppression of cortex during 10 Hz stimulation might be related to the frequency-dependent modulation of a GABAergic population. The response properties of the zona incerta (ZI), which has been implicated in providing a powerful GABAergic modulation of 10 Hz spike-wave activity in spontaneous absence seizures in the rat, was investigated. Anatomically, ZI sends direct GABAergic projections to somatosensory thalamic nuclei and sensory cortex. Functionally, ZI has also been shown to selectively gate sensory information processing in higher-order thalamic nuclei through GABAergic inhibition. To investigate the involvement of zona incerta, single-unit and field potential electrophysiology recordings were performed in this region during simultaneous optogenetic stimulation of central thalamus at 10 or 40 Hz (FIG. 4A). EEG recordings were simultaneously collected in frontal cortex to directly evaluate the relationship between ZI activity and whole-brain arousal state, which is typically measured with forebrain EEG. The zona incerta was targeted using stereotactic localization and the well-defined somatotopic representation of this region. The electrode was targeted to −3.96 mm AP, +2.2-2.6 mm ML, +6.7-7.2 mm DV from dura. The zona incerta was identified according to a compatible depth reading, spike latencies consistent with a polysynaptic response (on the order of 10 ms; FIG. 4B), and a receptive field that responds to contralateral whisker stimulation, which zona incerta is known to possess (64). The electrode was initially lowered through the dorsal part of the VP thalamus (approximately 1.5 mm above zona incerta), which also responds to whisker stimulation, until the recorded neurons did not respond to such a stimulus. The electrode was then lowered for another ~1.5 mm until the recorded neurons fired in response to whisker stimulation, indicating the zona incerta had been reached.

FIG. 4. Frequency-dependent spindle-like oscillations are evoked in zona incerta (ZI). (FIG. 4A) Diagram of in vivo recordings at zona incerta and simultaneous EEG recordings in frontal cortex during optical stimulation of central thalamus in anesthetized animals. (FIG. 4B) Representative peri-event time histograms of spiking activity from recorded ZI neurons aligned to the onset of individual light pulses, summed over all pulses and trials. Peak spike latencies are approximately 10 and 8 ms for 10 Hz (left) and 40 Hz (right) stimulations, suggesting that recordings are performed at least one synapse away from the stimulated population in central thalamus. Schematics at top illustrate the 30% duty cycle pulse trains which lasted 20 s for each frequency. (FIG. 4C) Representative peri-event time histograms over the 20 s period of stimulation show increases in ZI firing during 10 and 40 Hz stimulations. Among the 28 isolated single-units in zona incerta (n=2 animals), most exhibited a significant increase in firing rate during stimulation (n=26 and 22 out of 28 neurons, respectively; $P<0.05$, one-tailed Wilcoxon signed-rank test with 20 trials for each cell). (FIG. 4D) Representative field potential recordings from the same channel and trial number during 10 Hz (top) and 40 Hz (bottom) stimulation of central thalamus. Four amplitude-modulated, spindle-like oscillations (SLOs) are evoked during 10 Hz stimulation (marked by black triangles), while none are evoked during 40 Hz stimulation. Inset shows a zoomed-in SLO. (FIG. 4E) The number of SLOs was greater during 10 Hz stimulation than 40 Hz stimulation across 11 of 12 available channels (n=2 animals, 20 trials each, $P<0.01$, one-tailed Wilcoxon rank sum test). (F) When more than one SLO was evoked within the same 20 s period of 10 Hz stimulation, the distribution of inter-event intervals was centered at 6.6±0.2 s (s.e.m.). (FIG. 4G) Representative EEG recordings collected in frontal cortex during central thalamus stimulation and simultaneous ZI recordings. 10 Hz stimulation evokes a spike-wave response, which is associated with loss of consciousness and perceptual awareness, while 40 Hz stimulation evokes a low-voltage fast response indicative of arousal. (FIG. 4H) ChR2-positive processes were observed in zona incerta, providing a basis for its recruitment during stimulation of central thalamus. i.c.: internal capsule.

Figure 4C:
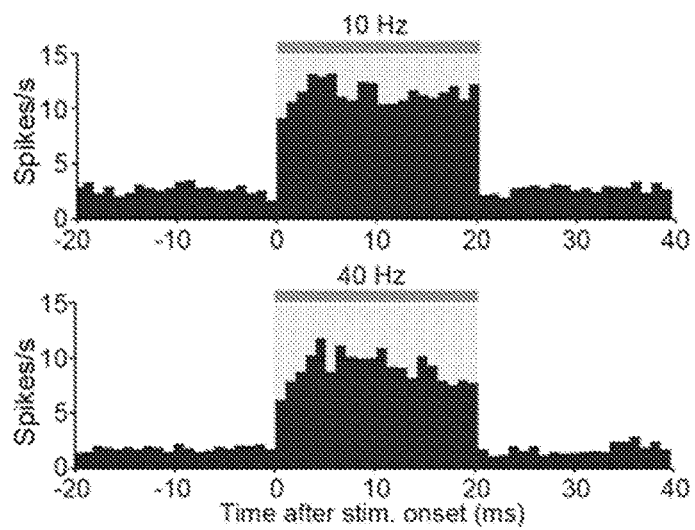
Figure 4D:
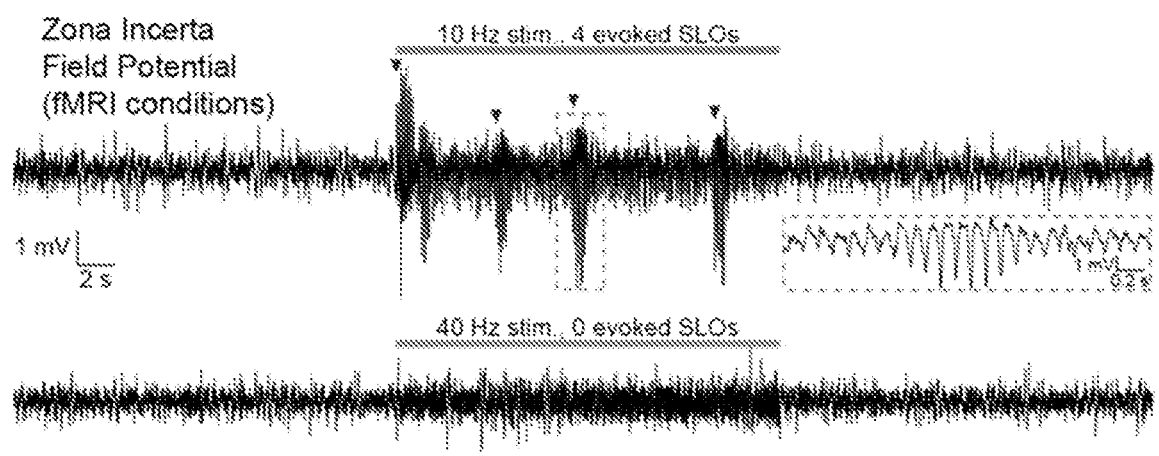
Figure 4F:
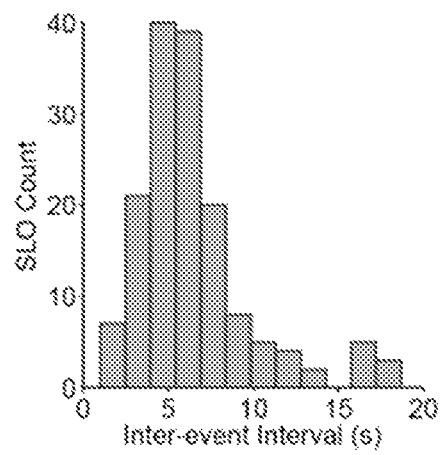
Figure 4G:
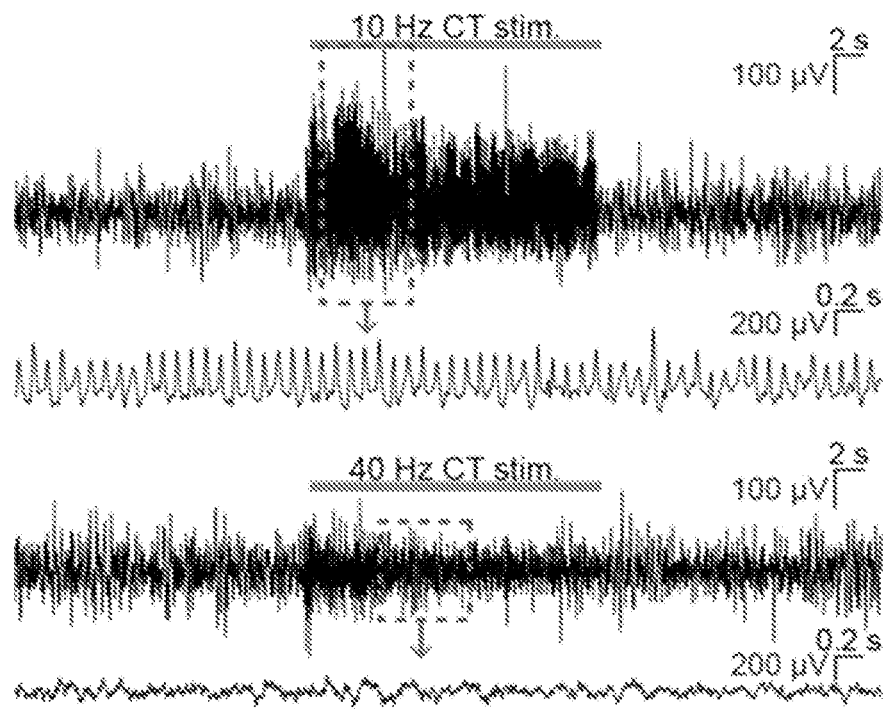
Figure 4H:
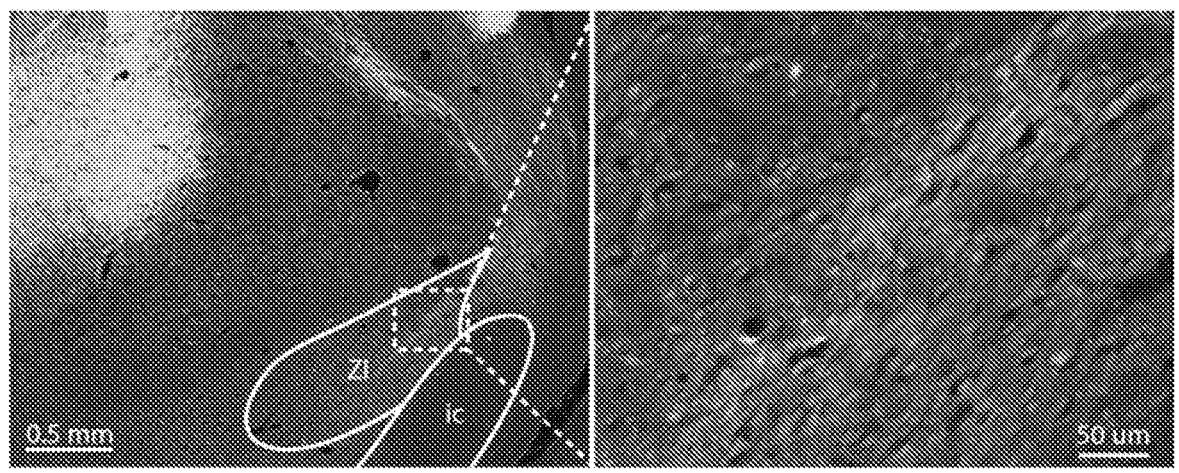
Figure 12:
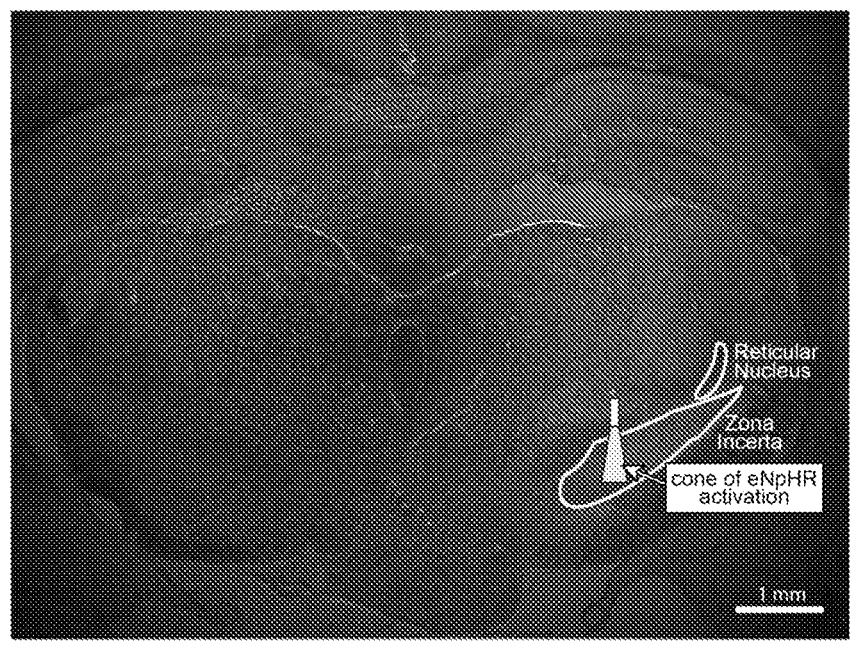
FIG. 12 is an image showing a wide-field fluorescence image of eNpHR expression in zona incerta, overlaid with the estimated cone of activated eNpHR (i.e. inhibited neurons) shown to scale, according to embodiments of the present disclosure.

Out of 28 isolated ZI neurons, the majority exhibited increases in their firing rate during central thalamus stimulation at both 10 and 40 Hz (FIG. 4C; n=26 and 22, respectively; $P<0.05$, Wilcoxon signed rank test between the 20 s pre-stimulation and stimulation periods, 20 trials for each neuron). However, a key difference was that large, amplitude-modulated spindle-like oscillations (SLOs) in the field potential occurred significantly more often during 10 Hz stimulation than 40 Hz stimulation (FIGS. 4D, 4E). These oscillations exhibited an inter-event interval centered around 6.6±0.2 s (s.e.m.), similar to those observed in thalamus during sleep onset (FIG. 4F). Consistent with this, simultaneous EEG recordings in frontal cortex revealed strong spike-wave modulation during 10 Hz stimulation and lower amplitude, fast oscillations during 40 Hz stimulation, which are associated with loss of consciousness and aroused brain states, respectively (FIG. 4G). EYFP-expressing axons were also observed in zona incerta (FIG. 4H), indicating that central thalamus relay neurons may have direct connections to zona incerta and providing a possible anatomical substrate for these responses Example 5: Cortical Inhibition Driven by Central Thalamus Stimulation Depends on Evoked Incertal Activity The observation of spindle-like oscillations in zona incerta during 10, but not 40, Hz central thalamus stimulation indicates that this region can be uniquely engaged by central thalamus-driven networks. However, it remains unknown whether the evoked activity in zona incerta plays a causal role in driving the frequency-dependent inhibition of somatosensory cortex. To address this question, the inhibitory opsin halorhodopsin (eNpHR) fused to the mCherry fluorescent marker and controlled by the pan-neuronal hSyn promoter was injected into zona incerta of four animals expressing ChR2-EYFP in central thalamus (FIGS. 5A and 5B, FIG. 12). Two new stimulation paradigms were explored: (1) 20 or 30 s continuous eNpHR activation, and (2) 20 s, 10 Hz central thalamus stimulation performed within a 30 s period of continuous eNpHR activation. Single-unit recordings were performed simultaneously at the zona incerta and sensory cortex during concurrent activation of these two opsins (FIG. 5C).

FIG. 5. Cortical inhibition driven by 10 Hz central thalamus stimulation depends on normal incertal processing. (FIG. 5A) Wide-field fluorescence image shows robust eNpHR-mCherry expression spatially localized to the right zona incerta. Scale bar, 1 mm. (FIG. 5B) Confocal images show eNpHR-mCherry localized to somatic membrane of neurons in zona incerta. Scale bar, 10 µm. 209 out of 882 DAPI-stained cells co-expressed mCherry in ZI (24%, n=2 animals). (FIG. 5C) Schematic of cortical electrophysiology recordings during 10 Hz stimulation of central thalamus and continuous (cont.) inhibition of zona incerta using ChR2 and eNpHR, respectively. (FIG. 5D) Peri-event time histogram of a representative neuron in zona incerta whose firing rate is suppressed during activation of eNpHR with 593 nm light. (FIG. 5E) Peri-event time histogram of a representative neuron in zona incerta whose firing rate remains suppressed throughout the period of 10 Hz central thalamus stimulation during eNpHR activation (compare to FIG. 4C). (FIG. 5F) Activation of eNpHR in zona incerta significantly reduces the change in incertal firing rate evoked by 10 Hz central thalamus stimulation in 60 of 70 neurons ($P<0.05$, one-sided Wilcoxon rank sum test). Changes in firing rate are normalized to pre-stimulation levels. (FIG. 5G) Peri-event time histograms from a representative cortical neuron show that the inhibitory response evoked by 10 Hz central thalamus stimulation is reversed by simultaneously suppressing activity in zona incerta. Firing rates are normalized to the average pre-stimulation values. (FIG. 5H) Quantification of evoked changes in cortical firing rate during 10 Hz central thalamus stimulation with and without concurrent eNpHR activation. 50 out of 76 cells exhibit reduced inhibition when central thalamus stimulation is paired with eNpHR activation ($P<0.05$, Wilcoxon rank sum test over 1 s bins). Changes in firing rate are normalized to pre-stimulation levels. (FIG. 5I) Confocal images show mCherry-positive axonal projections from zona incerta in somatosensory cortex. Scale bar, 20 µm.

FIG. 12. Wide-field fluorescence image of eNpHR expression in zona incerta, overlaid with the estimated cone of activated eNpHR (i.e. inhibited neurons) shown to scale. Penetration depth and volume were calculated to be 0.64 mm and 0.024 mm$^3$, respectively, using the methods described in and a threshold light intensity of 5 mW/mm$^2$. The optical fiber had a diameter of 105 μm, NA of 0.22, and half-angle of divergence of 9.3°. Penetration depth and activation volume correspond to an optical power of 3 mW exiting the fiber optic's tip. Stimulation coordinate corresponds to −3.96 mm AP, +2.4 mm ML, and −6.7 mm DV. The thalamic reticular nucleus, another region of dense GABAergic neurons, is shown for reference.

Among the 70 neurons recorded in zona incerta, delivery of 593 nm light resulted in a decrease in firing for 62 cells ($P<0.05$, Wilcoxon signed rank test between 20 s pre-stimulation period and 20 or 30 s stimulation period, 15-20 trials for each neuron), indicating that illumination of halorhodopsin was successful in suppressing incertal activity. The evoked decrease in neuronal firing rate typically lasted throughout the duration of 593 nm light delivery (FIG. 5D). When halorhodopsin activation in ZI was paired with 10 Hz stimulation of central thalamus, the previously described increase in incertal firing (FIG. 4C) was disrupted. In 60 out of 70 neurons, the difference in incertal firing rate between the 20 s 10 Hz central thalamus stimulation period and the pre-stimulation period was significantly reduced with concurrent eNpHR activation (FIG. 5F; $P<0.05$, one-sided Wilcoxon rank sum test, n=10-20 trials). FIG. 5E illustrates the suppression of zona incerta activity throughout the 20 s period of 10 Hz central thalamus stimulation in a representative neuron. These data indicate that activation of halorhodopsin significantly suppressed the incertal firing evoked by 10 Hz central thalamus stimulation, and successfully disrupted incertal processing.

To determine whether this suppression of zona incerta affected the cortical activity driven by central thalamus stimulation, the changes in somatosensory cortex firing rate evoked by ChR2 activation with and without illumination of eNpHR was quantified. 76 somatosensory cortex neurons were recorded, and the 20 s period of central thalamus stimulation was divided into four 5 s bins as before. Consistent with the data presented in FIG. 3, 68 cells (89%) exhibited a decrease in firing during 10 Hz stimulation of central thalamus (uncorrected $P<0.05$, Wilcoxon signed rank test; 10-15 trials for each neuron). Strikingly, however, suppression of zona incerta activity with eNpHR reversed this effect. Across animals, 50 out of 76 neurons (66%) exhibited reduced inhibition when central thalamus stimulation was paired with eNpHR activation (FIG. 5H; $P<0.05$, Wilcoxon rank sum test over 1 s bins; 10-20 trials for each neuron). Indeed, a fraction of cells switched from inhibitory responses to excitatory ones. FIG. 5G illustrates the firing patterns of one cell that exhibited an inhibitory response during 10 Hz central thalamus stimulation that was eliminated when zona incerta was simultaneously suppressed with eNpHR. Collectively, these data suggest that incertal activity during 10 Hz central thalamus stimulation has a net inhibitory effect on somatosensory cortex. In support of this influence being through direct anatomical connections, mCherry-positive axons were observed in the sensory cortex (FIG. 5I), consistent with previous reports of incerto-cortical projections. These findings present a conceptually novel role of zona incerta in central thalamus arousal circuits.

Figure 6A:
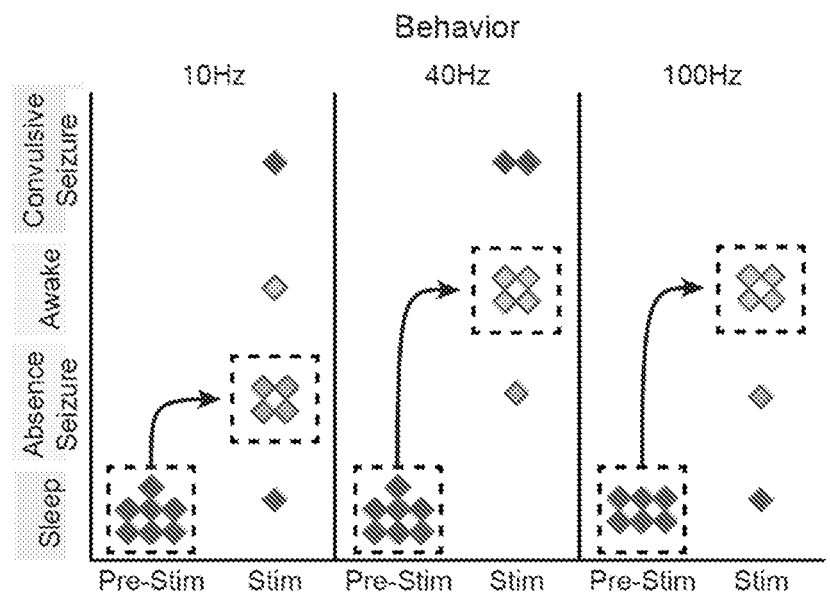
FIGS. 6A-6D are a collection of graphs showing that optogenetic stimulation of central thalamus in asleep animals modulates brain state in a frequency-dependent manner, according to embodiments of the present disclosure.
Figure 6B:
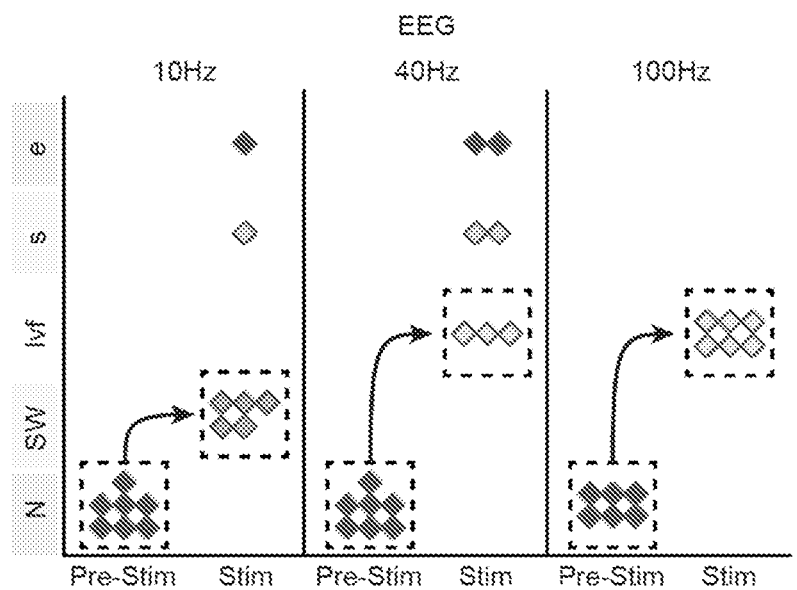
Figure 6C:
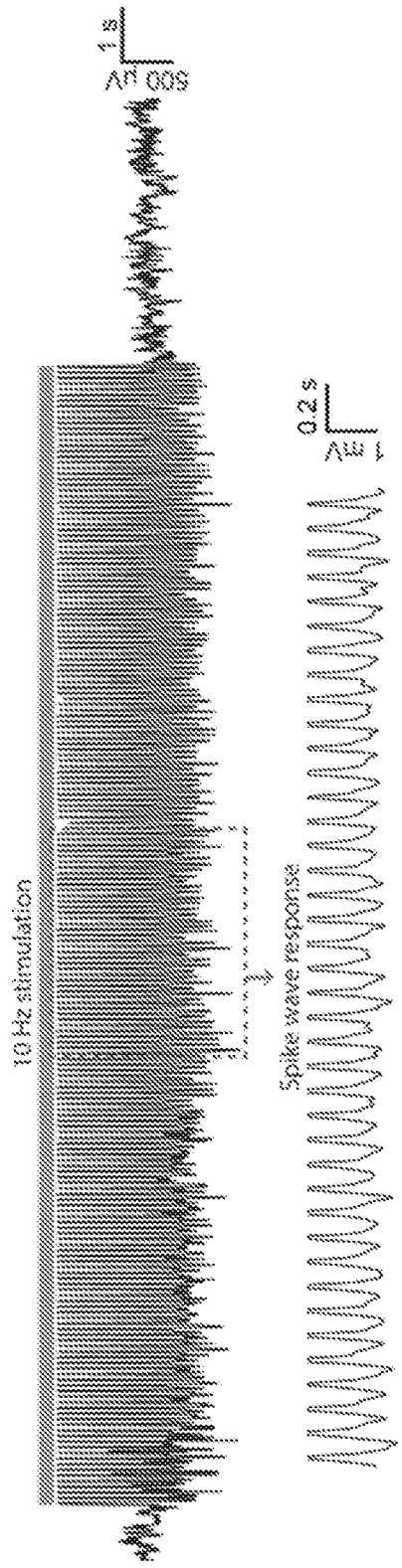
Figure 6D:
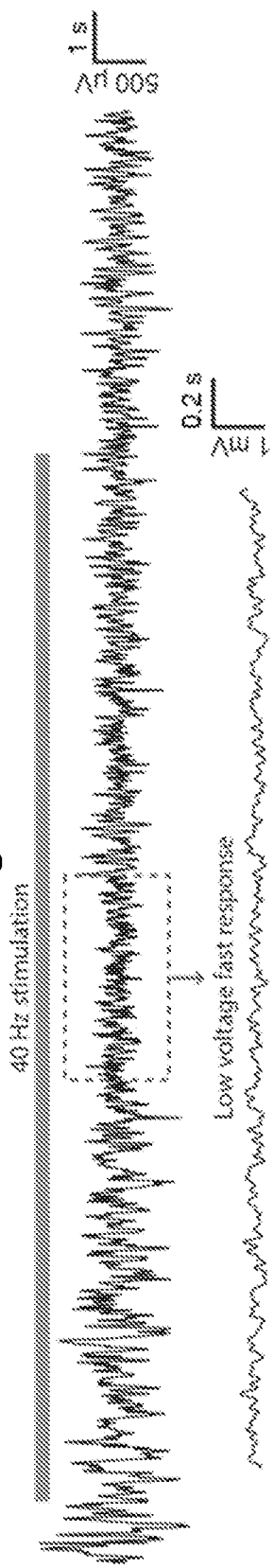
Figure 13:
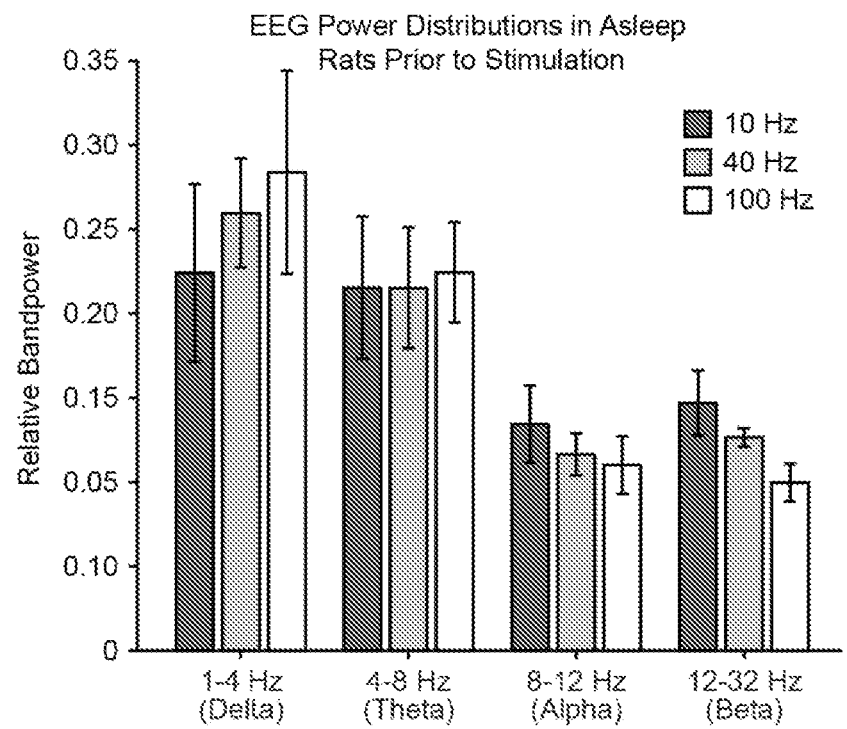
FIG. 13 is a graph showing that pre-stimulus activity is consistent across frequencies of stimulation in asleep rats, as quantified with EEG bandpower in delta, theta, alpha, and beta bands, according to embodiments of the present disclosure.

Example 6: Central Thalamus Stimulation Modulates Brain State in a Frequency-Dependent Manner Finally, to relate these findings more directly to behavior associated with central thalamus arousal circuits and previous electrical stimulation studies, 10, 40, and 100 Hz stimulations in asleep, unanaesthetized animals were performed with simultaneous video and EEG recordings (see Example 1). Control (pre-stimulus) activity was consistent across frequencies of stimulation, as quantified with EEG band power in delta, theta, alpha, and beta bands (FIG. 13). During 10 Hz stimulation, the majority of animals exhibited behavior indicative of an absence seizure, including freezing and behavioral arrest throughout stimulation followed by a return to sleep (FIG. 6A; n=4/7). In addition, the most common EEG response was a transition to slow spike-wave discharges (FIG. 6B,C; n=5/7), which are typically associated with loss of consciousness. In stark contrast, stimulations at 40 and 100 Hz resulted in behavioral transitions to an awake state, reflected by exploration and goal-directed movement (FIG. 6A; n=4/7 and 4/6, respectively). Similarly, the most common EEG pattern evoked by these high-frequency stimulations was a low-voltage-fast response (FIG. 6B; n=3/7 and 6/6, respectively), indicative of cortical activation and desynchronization. Collectively, these phenomena are consistent with the patterns of cortical and striatal recruitment observed with ofMRI. Moreover, the slow spike-wave and low-voltage-fast EEG responses evoked during behavioral experiments (FIG. 6C,D) match those recorded under anesthetized conditions (FIG. 4G), further linking the network activation patterns revealed by ofMRI to the arousal responses reported here, as well as those reported in early stimulation studies.

FIG. 6. Optogenetic stimulation of central thalamus in asleep animals modulates brain state in a frequency-dependent manner. (FIG. 6A) Low-frequency stimulation (10 Hz) in a majority of animals (n=4/7) evokes behavioral absence seizures, while high-frequency stimulations (40 and 100 Hz) cause a majority of animals to awaken (n=4/7 and 4/6, respectively). Dashed boxes indicate the most common response for each frequency, with arrows indicating the corresponding transition from sleep. (FIG. 6B) Low-frequency stimulation typically evokes spike-wave responses in EEG (n=5/7), consistent with the behavioral reading of absence seizures. The most frequent EEG response during high-frequency stimulations is low voltage fast (n=3/7 and 6/6), indicative of arousal. N, normal. SW, spike-wave. lvf, low voltage fast. s, spiking. e, evolving seizure. (FIGS. 6C, 6D) Representative traces of EEG responses classified as spike-wave and low voltage fast. Insets show 4 s magnification. Importantly, these EEG patterns match those recorded under anesthetized conditions (FIG. 4G), further linking the responses visualized with ofMRI to the reported behavioral responses. See also FIG. 13.

FIG. 13. Pre-stimulus activity is consistent across frequencies of stimulation in asleep rats, as quantified with EEG bandpower in delta, theta, alpha, and beta bands.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for in vivo circuit analysis of a brain of an individual, comprising:

i) illuminating a first region of a brain with:
- a first set of light pulses; and
- a second set of light pulses, wherein the first set has a different temporal pattern of light pulses from the second set, wherein the first region comprises neurons that generate action potentials upon activation, using light pulses of the first and second sets, of a first light-activated polypeptide expressed by the neurons of the first region, wherein the action potentials are generated at a frequency that scales with the temporal pattern of the light pulses of the first and second sets;

ii) measuring, in a second region of the brain, different from the first region, using functional magnetic resonance imaging (fMRI) scanning of a plurality of brain regions:
- a first change in neural activity induced by the first set of light pulses; and
- a second change in neural activity induced by the second set of light pulses;

iii) identifying a dynamic functional connection from the neurons of the first region to neurons of the second region based on a first difference between the first measured change and the second measured change;

iv) illuminating the first region by the first set of light pulses, with and without illumination of a third region, different from the first and second regions, with a third set of light pulses, wherein modulation of the activity of neurons of the third region is disrupted by activation, upon illumination of the third region, of a second light-activated polypeptide expressed by the neurons of the third region, wherein the third region comprises neurons whose activity is modulated by activity of the neurons of the first region;

v) measuring, in the second region:
- a third change in neural activity induced by the first set of light pulses without illumination of the third region; and a fourth change in neural activity induced by the first set of light pulses with illumination of the third region by the third set of light pulses; and vi) identifying, based on a second difference between the third measured change and the fourth measured change, a modulatory node of the dynamic functional connection, the modulatory node comprising neurons of the third region, wherein the neurons of the third region have a functional connection between neurons of the first region and the second region.

2. The method of claim 1, wherein the first difference is a change in sign.

3. The method of claim 1, wherein the different temporal pattern comprises at least one of different frequency or pulse width of the light pulses.

4. The method of claim 1, wherein the first and second regions are anatomically distinct regions of the brain.

5. The method of claim 1, wherein the neurons of the first region are excitatory neurons.

6. The method of claim 1, wherein the measuring (v) comprises measuring changes in neural activity using electrophysiology.

7. The method of claim 1, wherein the third region is illuminated with one or more optical fibers configured to transmit the third set of light pulses.

8. The method of claim 1, wherein the first and second regions are anatomically distinct regions of the brain.

9. The method of claim 1, wherein the first light-activated polypeptide is a light-activated ion channel.

10. The method of claim 1, wherein the second light-activated polypeptide is a light-activated ion pump.

11. The method of claim 1, wherein the individual is a mammal.

12. The method of claim 1, wherein the individual is anesthetized.

13. The method of claim 1, wherein the iii) identifying the dynamic functional connection from the neurons of the first region to neurons of the second region comprises
calculating the first difference between the first measured change and the second measured change;
determining that a first functional connection from the neurons of the first region to the neurons of the second region is a dynamic functional connection when the first measured change and the second measured change are different.

14. The method of claim 13, wherein the first difference is non-linear relative to the difference in the temporal pattern of the first set and second set of light pulses.

15. The method of claim 1, wherein the first region is a first internal region of the brain.

16. The method of claim 15, wherein the first internal region of the brain comprises at least a part of a region selected from the group consisting of thalamus, sensory cortex, zona incerta (ZI), ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyms, entorhinal cortex, olfactory cortex, primary motor cortex, and cerebellum.

17. The method of claim 1, wherein the first region is illuminated with one or more optical fibers configured to transmit the first set and second set of light pulses.

18. The method of claim 17, wherein a volume of the first region illuminated by the light pulses is 100 mm$^3$ or less.

19. The method of claim 1, wherein the vi) identifying the modulatory node of the dynamic functional connection comprises
calculating the second difference between the third measured change and the fourth measured change; and
determining whether the neurons of the third region mediate the first measured change.

20. The method of claim 19, wherein the second difference is smaller in magnitude than the first difference.

21. The method of claim 1, wherein the third region is a second internal region of the brain.

22. The method of claim 21, wherein the second internal region of the brain comprises at least a part of a region selected from the group consisting of thalamus, sensory cortex, zona incerta (ZI), ventral tegmental area (VTA), prefontal cortex (PFC), nucleus accumbens (NAc), amygdala (BLA), substantia nigra, ventral *pallidum*, globus pallidus, dorsal striatum, ventral striatum, subthalamic nucleus, hippocampus, dentate gyrus, cingulate gyrus, entorhinal cortex, olfactory cortex, primary motor cortex, and cerebellum.

* * * * *